(12) United States Patent
Taylor et al.

(10) Patent No.: US 7,579,432 B2
(45) Date of Patent: Aug. 25, 2009

(54) CYCLIC PEPTIDES AS G-PROTEIN-COUPLED RECEPTOR ANTAGONISTS

(75) Inventors: Stephen Maxwell Taylor, Bellbird Park (AU); Ian Alexander Shiels, Muirlea (AU); David Fairlie, Springwood (AU); Darren March, Banks (AU); Michael Whitehouse, Holland Park W. (AU)

(73) Assignee: Promics Pty Limited, Macquarie Park, New South Wales (AU)

( * ) Notice: Subject to any disclaimer, the term of this patent is extended or adjusted under 35 U.S.C. 154(b) by 306 days.

(21) Appl. No.: 10/493,117

(22) PCT Filed: Oct. 17, 2002

(86) PCT No.: PCT/AU02/01427

§ 371 (c)(1),
(2), (4) Date: Oct. 24, 2005

(87) PCT Pub. No.: WO03/033528

PCT Pub. Date: Apr. 24, 2003

(65) Prior Publication Data

US 2006/0217530 A1 Sep. 28, 2006

(30) Foreign Application Priority Data

Oct. 17, 2001 (AU) .................................... PR8334

(51) Int. Cl.
C07K 5/12 (2006.01)
A61K 38/12 (2006.01)

(52) U.S. Cl. .......................................... 530/317; 514/9
(58) Field of Classification Search ....................... None
See application file for complete search history.

(56) References Cited

U.S. PATENT DOCUMENTS 5,807,824 A * 9/1998 van Oostrum et al. ......... 514/12

FOREIGN PATENT DOCUMENTS

WO WO 99/00406 * 1/1999
WO WO 9900406 * 1/1999

OTHER PUBLICATIONS

Finch et al., J. Med. Chem., 1999, vol. 42, pp. 1965-1974.*
Paczkowski et al., "Pharmacological Characterization of Antagonists of the C5a Receptor," Brit. J. Pharmacol., 128:1461-1466, 1999.
Strachan et al., "A New Small Molecule C5a Receptor Antagonist Inhibits the Reverse-Passive Arthus Reaction and Endotoxic Shock in Rats," J. Immunol., 164:6560-6565, 2000.
International Search Report for PCT/AU02/01427, mailed Dec. 20, 2002.
Finch et al., "Low-Molecular-Weight Peptidic and Cyclic Antagonists of the Receptor for the Complement Factor C5a," J. Med. Chem., 42:1965-1974, 1999.
European Search Report; EP 02771873; Nov. 9, 2005.

* cited by examiner

Primary Examiner—Christopher R. Tate
Assistant Examiner—Roy Teller
(74) Attorney, Agent, or Firm—Mark D. Moore; Haynes and Boone, LLP

(57) ABSTRACT

The invention relates to novel cyclic compounds which have the ability to modulate the activity of G protein-coupled receptors. The compounds preferably act as antagonists. In preferred embodiments, the invention provides cyclic peptidic and peptidomimetic antagonists of C5a receptors, which are active against C5a receptors on polymorphonuclear leukocytes and macrophages. The compounds of the invention are both potent and selective, and are useful in the treatment of a variety of inflammatory conditions.

7 Claims, 14 Drawing Sheets

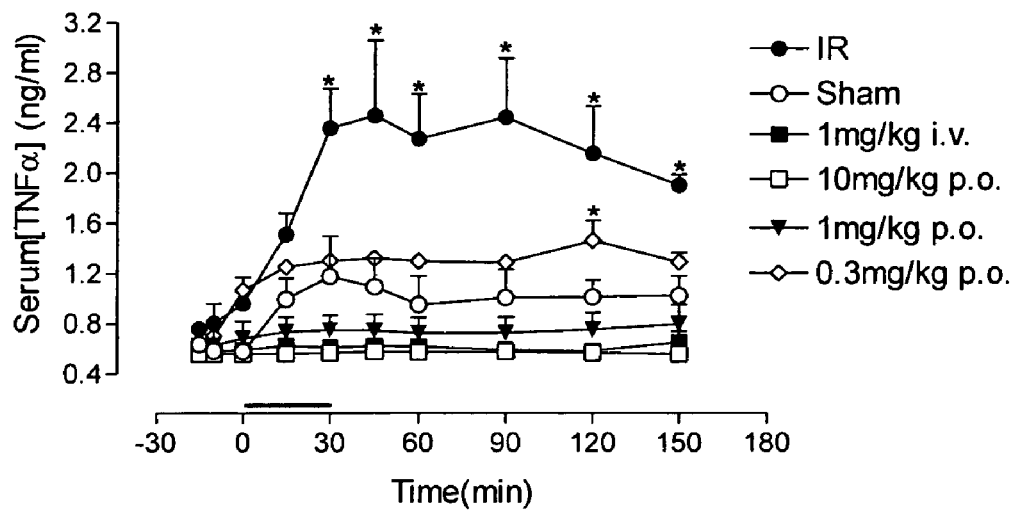
FIGURE 6
FIGURE 7
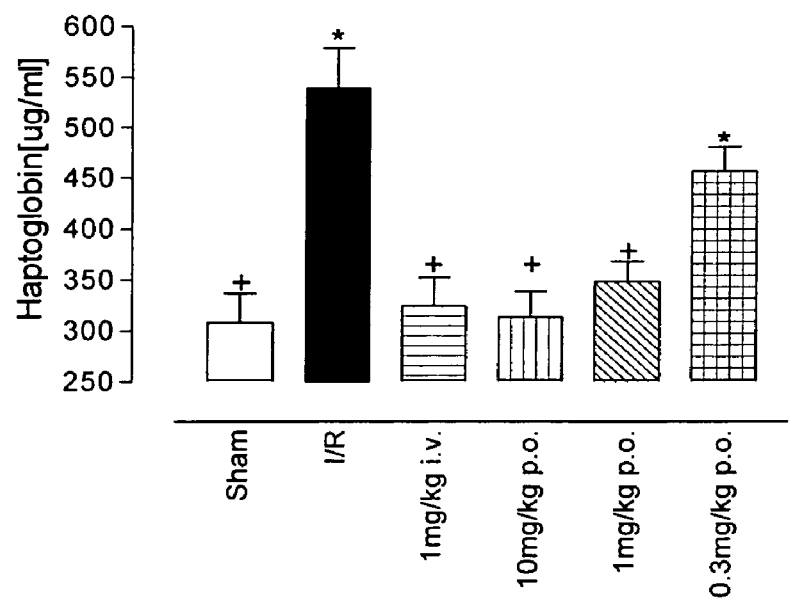

CYCLIC PEPTIDES AS G-PROTEIN-COUPLED RECEPTOR ANTAGONISTS

The present application is a nationalization of PCT Application Serial No. PCT/AU02/01427, filed Oct. 17, 2002, which claims priority to Australian Provisional Application No. PR 8334, filed Oct. 17, 2001.

FIELD OF THE INVENTION

This invention relates to novel cyclic compounds which have the ability to modulate the activity of G protein-coupled receptors. The compounds preferably act as antagonists. In preferred embodiments, the invention provides cyclic peptidic and peptidomimetic antagonists of C5a receptors, which are active against C5a receptors on polymorphonuclear leukocytes and macrophages. The compounds of the invention are both potent and selective, and are useful in the treatment of a variety of inflammatory conditions.

BACKGROUND OF THE INVENTION

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

G protein-coupled receptors are prevalent throughout the human body, comprising approximately 60% of known cellular receptor types, and mediate signal transduction across the cell membrane for a very wide range of endogenous ligands. They participate in a diverse array of physiological and pathophysiological processes, including, but not limited to those associated with cardiovascular, central and peripheral nervous system, reproductive, metabolic, digestive, immunoinflammatory, and growth disorders, as well as other cell-regulatory and proliferative disorders. Agents which selectively modulate functions of G protein-coupled receptors have important therapeutic applications. These receptors are becoming increasingly recognised as important drug targets, due to their crucial roles in signal transduction (G protein-coupled Receptors, IBC Biomedical Library Series, 1996).

One of the most intensively studied G protein-coupled receptors is the receptor for C5a. C5a is one of the most potent chemotactic agents known, and recruits neutrophils and macrophages to sites of injury, alters their morphology; induces degranulation; increases calcium mobilisation, vascular permeability (oedema) and neutrophil adhesiveness; contracts smooth muscle; stimulates release of inflammatory mediators, including histamine, TNF-α, IL-1, IL-6, IL-8, prostaglandins, and leukotrienes, and of lysosomal enzymes; promotes formation of oxygen radicals; and enhances antibody production (Gerard and Gerard, 1994).

Overexpression or underregulation of C5a is implicated in the pathogenesis of immune system-mediated inflammatory conditions, such as rheumatoid arthritis, adult respiratory distress syndrome (ARDS), systemic lupus erythematosus, tissue graft rejection, ischaemic heart disease, reperfusion injury, septic shock, psoriasis, gingivitis, atherosclerosis, Alzheimer's disease, lung injury and extracorporeal post-dialysis syndrome, and in a variety of other conditions (Whaley 1987; Sim 1993).

Agents which limit the pro-inflammatory actions of C5a have potential for inhibiting chronic inflammation, and its accompanying pain and tissue damage. For these reasons, molecules which prevent C5a from binding to its receptors are useful for treating chronic inflammatory disorders driven by complement activation. Such compounds also provide valuable new insights into the mechanisms of complement-mediated immunity.

In our previous application No. PCT/AU98/00490, the entire disclosure of which is incorporated herein by this reference, we described the three-dimensional structure of some analogues of the C-terminus of human C5a, and used this information to design novel compounds which bind to the human C5a receptor (C5aR), behaving as either agonists or antagonists of C5a. It had previously been thought that a putative antagonist might require both a C-terminal arginine and a C-terminal carboxylate for receptor binding and antagonist activity (Konteatis et al, 1994). In PCT/AU98/00490 we showed that in fact a terminal carboxylate group is not generally required either for high affinity binding to C5aR or for antagonist activity. Instead we found that a hitherto unrecognised structural feature, a turn conformation, was the key recognition feature for high affinity binding to the human C5a receptor on neutrophils. We used these findings to design constrained structural templates which enable hydrophobic groups to be assembled into a hydrophobic array for interaction with a C5a receptor.

By investigating the effect of varying the structure at each amino acid residue in the most potent compound identified in our previous application, we have now developed further examples of cyclic antagonists of the C5a receptor on human neutrophils and have identified potent C5aR antagonist activity for a range of compounds. These compounds each comprise a cyclic scaffold which satisfies the general three-dimensional structural requirements set out in the earlier application No. PCT/AU98/00490, but we have now found that certain substituents attached to the cycle surprisingly lead to most unexpected results, producing both high and low antagonist potencies which were not accurately predicted in the previous application No. PCT/AU98/00490. These surprising new findings allow us to refine and better define the required pharmacophore for antagonism of C5a receptors. The unexpected structure-activity relationships described herein help to define a refined structural pharmacophore for active antagonism of C5a receptors on human polymorphonuclear leukocytes (neutrophil granulocytes). This pharmacophore is expected to be appropriate also for C5a receptors on other human and mammalian cells,

SUMMARY OF THE INVENTION

According to a first aspect, the invention provides a compound which is an antagonist of a G protein-coupled receptor, which has substantially no agonist activity, and which is a cyclic peptide or peptidomimetic of formula I:

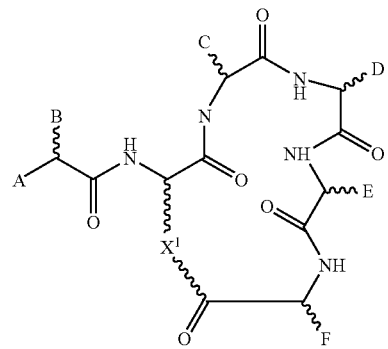

where A is H, alkyl, aryl, $NH_2$, NH-alkyl, $N(alkyl)_2$, NH-aryl, NH-acyl, NH-benzoyl, $NHSO_3$, $NHSO_2$-alkyl, $NHSO_2$-aryl, OH, O-alkyl, or O-aryl;

B is an alkyl, aryl, phenyl, benzyl, naphthyl or indole group, or the side chain of a D- or L-amino acid such as L-phenylalanine or L-phenylglycine, but is not the side chain of glycine, D-phenylalanine, L-homophenylalanine, L-tryptophan, L-homotryptophan, L-tyrosine, or L-homotyrosine;

C is a small substituent, such as the side chain of a D-, L- or homo-amino acid such as glycine, alanine, leucine, valine, proline, hydroxyproline, or thioproline, but is preferably not a bulky substituent such as isoleucine, phenylalanine, or cyclohexylalanine;

D is the side chain of a neutral D-amino acid such as D-Leucine, D-homoleucine, D-cyclohexylalanine, D-homocyclohexylalanine, D-valine, D-norleucine, D-homo-norleucine, D-phenylalanine, D-tetrahydroisoquinoline, D-glutamine, D-glutamate, or D-tyrosine, but is preferably not a small substituent such as the side chain of glycine or D-alanine, a bulky planar side chain such as D-tryptophan, or a bulky charged side chain such as D-arginine or D-Lysine;

E is a bulky substituent, such as the side chain of an amino acid selected from the group consisting of L-phenylalanine, L-tryptophan and L-homotryptophan, or is L-1-napthyl or L-3-benzothienyl alanine, but is not the side chain of D-tryptophan, L-N-methyltryptophan, L-homophenylalanine, L-2-naphthyl L-tetrahydroisoquinoline, L-cyclohexylalanine, D-leucine, L-fluorenylalanine, or L-histidine;

F is the side chain of L-arginine, L-homoarginine, L-citrulline, or L-canavanine, or a bioisostere thereof, ie. a side chain in which the terminal guanidine or urea group is restrained, but the carbon backbone is replaced by a group which has different structure, but is such that the side chain as a whole reacts with the target protein in the same way as the parent group;

X is —$(CH_2)_n$NH— or $(CH_2)_n$—S—, where n is an integer of from 1 to 4, preferably 2 or 3; —$(CH_2)_2$O—; —$(CH_2)_3$O—; —$(CH_2)_3$—; —$(CH_2)_4$—; —$CH_2$COCHRNH—; or —$CH_2$—CHCOCHRNH—, and where R is the side chain of any common or uncommon amino acid, with the proviso that the compound is not compound 1 referred to below.

In C, both the cis and trans forms of hydroxyproline and thioproline may be used.

Preferably A is an acetamide group, an aminomethyl group, or a substituted or unsubstituted sulphonamide group.

Preferably where A is a substituted sulphonamide, the substituent is an alkyl chain of 1 to 6, preferably 1 to 4 carbon atoms, or a phenyl or toluyl group.

Preferably the G protein-coupled receptor is a C5a receptor. However, we have found that the leading compound of our earlier application also has significant binding affinity at vasopressin and neurokinin receptors, and therefore these receptors are also within the scope of the invention.

In a particularly preferred embodiment, the compound has antagonist activity against C5aR, and has no C5a agonist activity.

The cyclic compounds of the invention are preferably antagonists of C5a receptors on human, mammalian cells including, but not limited to, human polymorphonuclear leukocytes and human macrophages. The compounds of the invention preferably bind potently and selectively to C5a receptors, and more preferably have potent antagonist activity at sub-micromolar concentrations. Even more preferably the compound has a receptor affinity IC50<25 μM, and an antagonist potency IC50<1 μM.

Still more preferably the compound is selected from the group consisting of compounds 2 to 6, 10 to 15, 17, 19, 20, 22, 25, 26, 28, 30, 31, 33 to 37, 39 to 45, 47 to 50, 52 to 58 and 60 to 70 described herein. Most preferably the compound is compound 33, compound 60 or compound 45.

For the purposes of this specification, the term "alkyl" is to be taken to mean a straight, branched, or cyclic, substituted or unsubstituted alkyl chain of 1 to 6, preferably 1 to 4 carbons. Most preferably the alkyl group is a methyl group. The term "acyl" is to be taken to mean a substituted or unsubstituted acyl of 1 to 6, preferably 1 to 4 carbon atoms. Most preferably the acyl group is acetyl. The term "aryl" is to be understood to mean a substituted or unsubstituted homocyclic or heterocyclic aryl group, in which the ring preferably has 5 or 6 members.

A "common" amino acid is a L-amino acid selected from the group consisting of glycine, leucine, isoleucine, valine, alanine, phenylalanine, tyrosine, tryptophan, aspartate, asparagine, glutamate, glutamine, cysteine, methionine, arginine, lysine, proline, serine, threonine and histidine.

An "uncommon" amino acid includes, but is not restricted to, D-amino acids, homo-amino acids, N-alkyl amino acids, dehydroamino acids, aromatic amino acids other than phenylalanine, tyrosine and tryptophan, ortho-, meta- or para-aminobenzoic acid, ornithine, citrulline, canavanine, norleucine, δ-glutamic acid, aminobutyric acid, L-fluorenylalanine, L-3-benzothienylalanine, and α,α-disubstituted amino acids.

According to a second aspect, the invention provides a composition comprising a compound according to the invention, together with a pharmaceutically-acceptable carrier or excipient.

The compositions of the invention may be formulated for use in oral, parenteral, inhalational, intranasal, transdermal or other topical applications, but oral or topical formulations are preferred For topical administration, vehicles such as dimethylsulphonate or propylene glycol may be used. Other vehicles may be preferred depending on the tissue surface to be treated.

It is expected that most if not all compounds of the invention will be stable in the presence of metabolic enzymes such as those of the gut, blood, lung or intracellular enzymes. Such stability can readily be tested by routine methods known to those skilled in the art.

Suitable formulations for administration by any desired route may be prepared by standard methods, for example by reference to well-known textbooks such as Remington: The Science and Practice of Pharmacy, Vol. II, 2000 (20th edition), A-R. Gennaro (ed), Williams & Wilkins, Pennsylvania.

In a third aspect, the invention provides a method of treatment of a pathological condition mediated by a G protein-coupled receptor, comprising the step of administering an effective amount of a compound of the invention to a mammal or vertebrate in need of such treatment.

Preferably the condition mediated by a G protein-coupled receptor is a condition mediated by a C5a receptor, and more preferably involves overexpression or underregulation of C5a. Such conditions include but are not limited to rheumatoid arthritis, adult respiratory distress syndrome (ARDS), systemic lupus erythematosus, tissue graft rejection, ischaemic heart disease, reperfusion injury, septic shock, gingivitis, fibrosis, atherosclerosis, multiple sclerosis, Alzheimer's disease, asthma, dementias, central nervous system disorders, lung injury, extracorporeal post-dialysis syndrome, and dermal inflammatory disorders such as psoriasis, eczema and contact dermatitis.

In one preferred embodiment the condition is rheumatoid arthritis.

In a second preferred embodiment the condition is reperfusion injury. In this second embodiment it will be clearly understood that the proviso to formula I does not apply.

While the invention is not in any way restricted to the treatment of any particular animal or species, it is particularly contemplated that the compounds of the invention will be useful in medical treatment of humans, and will also be useful in veterinary treatment, particularly of companion animals such as cats and dogs, livestock such as cattle, horses and sheep, and zoo animals, including non-human primates, large bovids, felids, ungulates and canids. Other species which may be amenable to treatment include reptiles, fishes or amphibians.

The compounds may be administered at any suitable dose and by any suitable route. Oral, topical, transdermal or intranasal administration is preferred, because of the greater convenience and acceptability of these routes. Topical applications could also include the use of formulations such as pessaries or suppositories for vaginal or rectal administration or the use of aqueous drops for topical administation to ears or eyes. The effective dose will depend on the nature of the condition to be treated, and the age, weight, and underlying state of health of the individual treatment. This will be at the discretion of the attending physician or veterinarian. Suitable dosage levels may readily be determined by trial and error experimentation, using methods which are well known in the art.

For the purposes of this specification it will be clearly understood that the word "comprising" means "including but not limited to", and that the word "comprises" has a corresponding meaning.

BRIEF DESCRIPTION OF THE FIGURES

FIG. 6 shows the effect of a C5a antagonist on gut Ischemia-reperfusion induced serum TNFα elevation.

FIG. 7 shows the effect of a C5a antagonist on gut ischemia-reperfusion induced serum haptoglobin elevation.

(a) 3D53 (compound 1); (b) compound 45; (c) compound 17.

Figure 15A:
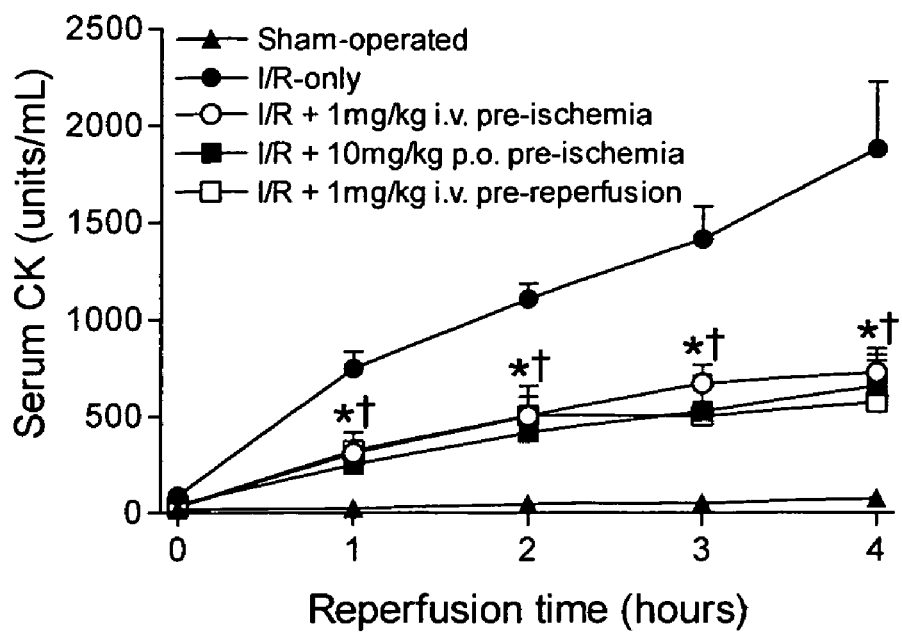
Figure 15B:
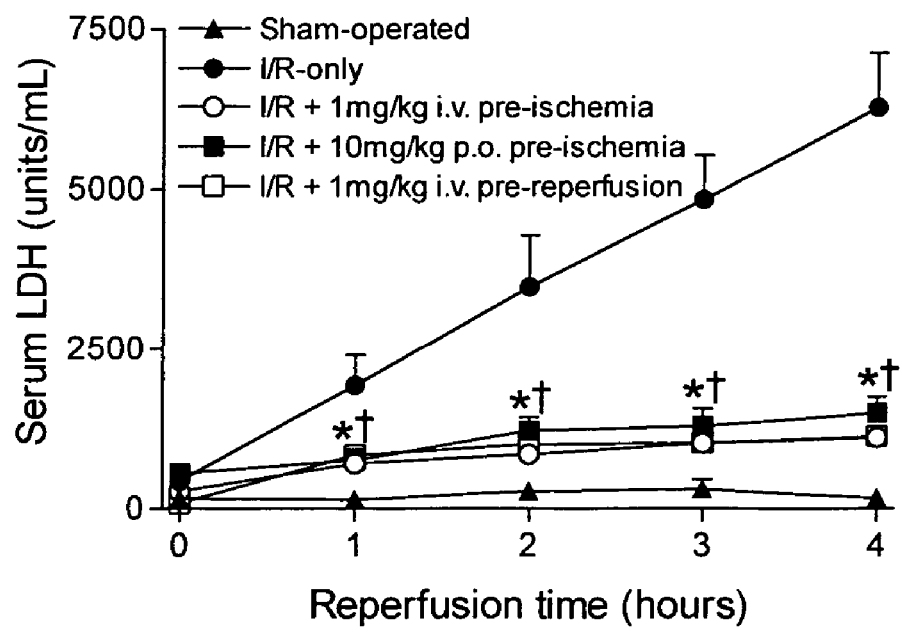

FIG. 15 shows the effects of the C5a antagonist AcF-[OPdChaWR] on increases in serum levels of (A) creatine kinase (CK) and (B) lactate dehydrogenase (LDH) during reperfusion in rats. Data represent the mean±SEM (n=6-10). *$P<0.05$ all drug-treated groups vs. ischemia/reperfusion (I/R)-only; †$P<0.05$ all drug-treated groups vs. sham-operated.

FIG. 16 shows the effects of the C5a antagonist, AcF-[OPdChaWR], on increases in serum levels of (A) alanine aminotransferase (ALT) and (B) aspartate aminotransferase (AST) following 2, 3 and 4 hours reperfusion in rats. Data represent the mean±SEM (n=6-10). *$P<0.05$ all drug-treated groups vs. ischemia/reperfusion (I/R)-only; †$P<0.05$ all drug-treated groups vs. sham-operated.

FIG. 17 shows the levels of (A) circulating PMNs, (B) muscle myeloperoxidase (MPO), (C) lung MPO and (D) liver MPO in rats. Levels were measured in rats at the completion of the experiment. Data represent the mean±SEM (n=4-10). *$P<0.05$ vs. ischemia/reperfusion (I/R)-only; †$P<0.05$ vs. sham-operated.

Figure 18:
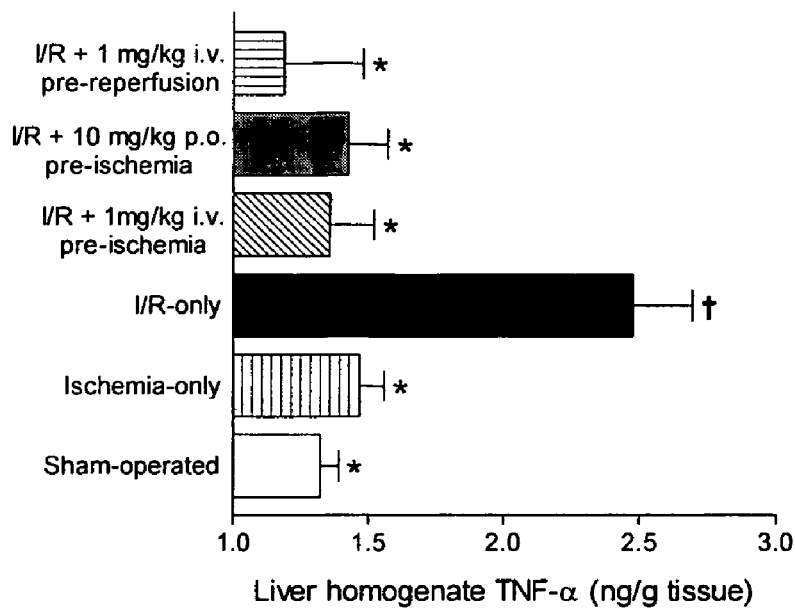

FIG. 18 shows the levels of tumour necrosis factor-α (TNF-α) in rat liver homogenate samples taken at the completion of the experiment. Data represent the mean±SEM (n=4-10). *$P<0.05$ vs. ischemia/reperfusion (I/R)-only; †$P<0.05$ vs. sham-operated.

Figure 19:
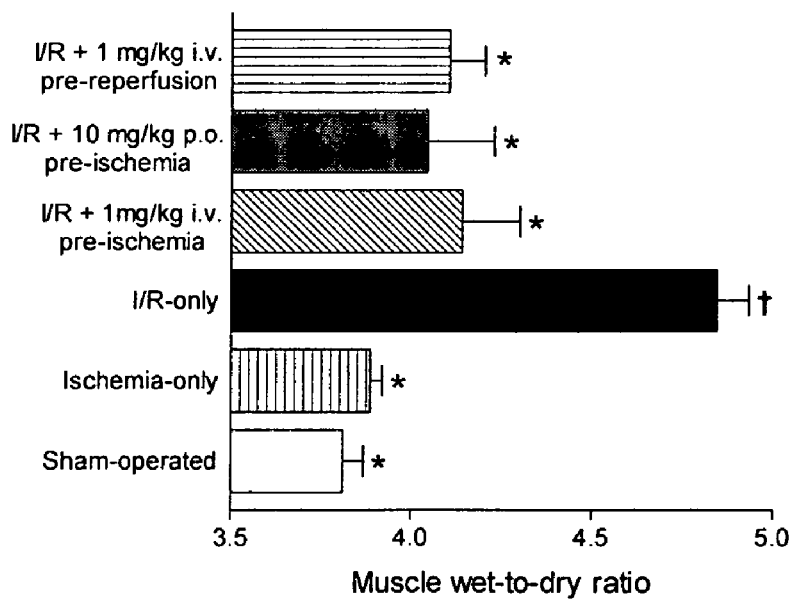

FIG. 19 shows the amount of edema (wet-to-dry ratio) in the hindlimb muscle of rats at the completion of the experiment. Data represent the mean±SEM (n=4-10). *$P<0.05$ vs. ischemia/reperfusion (I/R)-only; †$P<0.05$ vs. sham-operated.

DETAILED DESCRIPTION OF THE INVENTION

Generally, the terms "treating", "treatment" and the like are used herein to mean affecting a subject, tissue or cell to obtain a desired pharmacological and/or physiological effect. The effect may be prophylactic in terms of completely or partially preventing a disease or sign or symptom thereof, and/or may be therapeutic in terms of a partial or complete cure of a disease. "Treating" as used herein covers any treatment of, or prevention of disease in a vertebrate, a mammal, particularly a human, and includes: preventing the disease from occurring in a subject who may be predisposed to the disease, but has not yet been diagnosed as having it; inhibiting the disease, ie., arresting its development; or relieving or ameliorating the effects of the disease, ie., cause regression of the effects of the disease.

The invention includes various pharmaceutical compositions useful for ameliorating disease. The pharmaceutical compositions according to one embodiment of the invention are prepared by bringing a compound of formula I, analogues, derivatives or salts thereof and one or more pharmaceutically-active agents or combinations of compound of formula I and one or more pharmaceutically-active agents into a form suitable for administration to a subject using carriers, excipients and additives or auxiliaries.

Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 20th ed. Williams & Wilkins (2000) and The British National Formulary 43rd ed. (British Medical Association and Royal pharmaceutical Society of Great Britain, 2002; http://bnf.rhn.net), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dosage units. Solid dosage units include tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or by administration of several smaller dose units, and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, eg., in Langer, Science, 249: 1527, (1990). Formulations for oral use may be in the form of hard gelatin capsules, in which the active ingredient is mixed with an inert solid diluent, for example, calcium carbonate, calcium phosphate or kaolin. They may also be in the form of soft gelatin capsules, in which the active ingredient is mixed with water or an oil medium, such as peanut oil, liquid paraffin or olive oil.

Aqueous suspensions normally contain the active materials in admixture with excipients suitable for the manufacture of aqueous suspensions. Such excipients may be suspending agents such as sodium carboxymethyl cellulose, methyl cellulose, hydroxypropylmethylcellulose, sodium alginate, polyvinylpyrrolidone, gum tragacanth and gum acacia; dispersing or wetting agents, which may be (a) a naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethyleneoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleaginous suspension. This suspension may be formulated according to known methods using suitable dispersing or wetting agents and suspending agents such as those mentioned above. The sterile injectable preparation may also be a sterile injectable solution or suspension in a non-toxic parenterally-acceptable diluent or solvent, for example, as a solution in 1,3-butanediol. Among the acceptable vehicles and solvents which may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid may be used in the preparation of injectables.

Compounds of formula I may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Dosage levels of the compound of formula I of the present invention will usually be of the order of about 0.5 mg to about 20 mg per kilogram body weight, with a preferred dosage range between about 0.5 mg to about 10 mg per kilogram body weight per day (from about 0.5 g to about 3 g per patient per day). The amount of active ingredient which may be combined with the carrier materials to produce a single dosage will vary, depending upon the host to be treated and the particular mode of administration. For example, a formulation intended for oral administration to humans may contain about 5 mg to 1 g of an active compound with an appropriate and convenient amount of carrier material, which may vary from about 5 to 95 percent of the total composition. Dosage unit forms will generally contain between from about 5 mg to 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In addition, some of the compounds of the invention may form solvates with water or common organic solvents. Such solvates are encompassed within the scope of the invention.

The compounds of the invention nay additionally be combined with other compounds to provide an operative combination. It is intended to include any chemically compatible combination of pharmaceutically-active agents, of the compound of formula I of this invention.

It will be clearly understood that the foregoing comments regarding pharmaceutical formulations, routes of administration, dosage levels and the like are equally applicable to compound 1.

Abbreviations used herein are as follows:

BOP benzotriazole-1-yl-oxy-tris-(dimethylamino)-phosphonium hexafluorophosphate
C5cR C5a receptor
$dH_2O$ distilled water
D-Cha D-cyclohexylamine
DIPEA diisopropylethylamine
DMF N,N-dimethylformamide
DMSO dimethylsulphoxide HBTU O-benzotriazole N',N',N',N'-tetramethyluronium hexafluorophosphate;
HEPES N-[2-hydroxyethyl]piperazine-N'-[2-ethane sulfonic acid]
HPLC high performance liquid chromatography
RP-HPLC reverse phase high performance liquid chromatography
i.v. intravenous
LPS lipopolysaccharide
PMN polymorphonuclear granulocyte
po oral
RMSD root mean square deviation
rp-HPLC reverse phase-high performance liquid chromatography
TFA trifluoroacetic acid;

Throughout the specification conventional single-letter and three-letter codes are used to represent amino acids.

The terms "3D53" and "PMX53" are synonymous, and represent the compound Ac-Phe-[Orn-Pro-dCha-Trp-Arg];

The terms "LP-10" and "PMX-201" are synonymous, and represent the compound Ac-Phe-[Orn-Pro-dCha-Trp-Cit]; and The terms "LP-16" and "PMX-205" are synonymous, and represent the compound HC-[Orn-Pro-dCha-Trp-Arg], in which "HC" indicates hydrocinnamate.

The invention will now be described by way of reference only to the following general methods and experimental examples.

We have found that all of the compounds of formula I which have so far been tested have broadly similar pharmacological activities, which are similar to those of compound 1 (also referred to herein as 3D53 or PMX53), although the physicochemical properties, potency, and bioavailability of the individual compounds varies somewhat depending on the specific substituents. Thus we expect that results obtained in vitro or in vivo with compound 1 will be reasonably predictive of activity of the compounds of formula I in corresponding assays.

General Methods

Protected amino acids and resins were obtined from Novabiochem. TEA, DIPEA and DMF (peptide synthesis grade) were purchased from Auspep. All other materials were reagent grade unless otherwise stated. Preparative scale reverse-phase HPLC separations were performed on a Vydac C18 reverse-phase column (2.2×25 cm), and analytical reverse-phase HPLC separations were performed on a Waters Delta-Pak PrepPak C18 reverse-phase column (0.8×10 cm), using gradient mixtures of solvent A=water/0.1% TFA and solvent B=water 10%/acetonitrile 90%, 0.09% TFA. The molecular weight of the peptides was determined by electrospray mass spectrometry, recorded on a triple quadrupole mass spectrometer (Pt SCIEX API III), as described elsewhere (Haviland et al, 1995). $^1$H-NMR spectra were recorded on either a Bruker ARX 500 MHz or a Varian Unity 400 spectrometer. Proton assignments were determined by 2D NMR experiments (DFCOSY, TOCSY, NOESY).

Compounds were analysed by mass spectrometry and by reversed phase analytical HPLC.

Compound Synthesis

Linear peptide sequences were assembled by manual stepwise standard solid-phase peptide synthesis (SPPS) techniques well known to those skilled in the art. The amino acids or peptide termini were activated with HBTU with DIEA in situ neutralisation, Couplings were monitored by the standard quantitative ninhydrin test. Boc chemistry was employed for temporary $N^\alpha$-protection of amino acids with two 1 minute treatments with TFA for Boc group removal. Peptides were synthesised on a Novabiochem Boc-D-Arg(Tos)-PAM or Boc-L-Arg(Tos)-PAM resin with a substitution value of approx. 0.2-0.5 mmol/g. The peptides were fully deprotected and cleaved by treatment with liquid HF (10 mL), p-cresol (1 ml) at −5° C. for 1-2 hrs. Peptides were purified by reversed phase HPLC (e.g. gradient: 0% B to 75% B over 60 min) and analysed by electrospray mass spectrometry.

Alternatively, the linear peptides can be synthesised by Fmoc chemistry, using HBTU/DIEA activation on an Fmoc-D-Arg(Mtr)-Wang resin. Fmoc group removal was effected using two 1 min treatments with 50% piperidine/DMF. Cleavage and deprotection using 95% TFA/2.5% TIPS/2.5% $H_2O$ gives the Mtr-protected peptide, which can be purified by RP-HPLC.

A general procedure for cyclisation of linear peptides involves dissolving the peptide (1 equiv.) and BOP (5 equiv.) in DMF (10 mM peptide concentration) and stirring vigorously, followed by the addition of DIEA (15 equiv.). Solutions are generally allowed to stir at room temperature overnight, although in most cases the reaction was complete within 2 hrs. DMF is removed under high vacuum at 30° C. on a rotary evaporator and then purified by RP-HPLC. For cyclic peptides containing a free N-terminus, an Fmoc group was used as the temporary N-terminal protecting group during the cyclisation step. DMF was removed under high vacuum at 30° C. on a rotary evaporator, and then the peptide was treated with 30% piperidine/DMF for 1 hr at room temperature to remove the Fmoc group. This was followed by solvent removal under high vacuum, and purification by RP-HPLC. Representative examples of the synthesis of the cycles are described below.

NMR Structure Determination $^1$H-NMR spectra were recorded for test compounds (3 mg in 750 µl $d_6$-DMSO, δ 2.50) referenced to solvent on a Varian Unity 400 spectrometer at 24° C. Two-dimensional $^1$H-NMR NOESY (relaxation delay 2.0 s, mix time 50-300 ms), DFQ-COSY and TOCSY (mixing time 75 ms) experiments were acquired and recorded in phase sensitive mode. Acquisition times=0.186 s, spectral width=5500 Hz, number of complex points ($t_1$ dimension)=1024 for all experiments. Data was zero-filled and Fourier transformed to 1024 real points in both dimensions.

NMR data for compound 1 was processed using TRIAD software (Tripos Assoc.) on a Silicon Graphics Indy work station. 2D NOE cross peaks were integrated and characterised into strong (1.8-2.5 Å), medium (2.3-3.5 Å) and weak (3.3-5.0 Å). Preliminary three-dimensional structures were calculated from upper and lower distance limit files using Diana 2.8 (69 distance constraints, including 27 for adjacent residues and 6 further away) with the redundant dihedral angle constraints (REDAC) strategy. Upper and lower distance constraints were accurately calculated using MARDI-GRAS. At this stage the peptide was examined for possible hydrogen bonds, and these were added as distance constraints. The 50 lowest energy Diana structures were subjected to restrained molecular dynamics (RMD) and energy minimisation (R). Initially, REM consisted of a 50 step steepest descent followed by 100 step conjugate gradient minimisation. RMD was performed by simulated heating of the structures to 300K for 1 ps, followed by 500K for 1 ps. The temperature was gradually lowered to 300K over 2 ps and finally for 2 ps at 200K. REM was performed again with a 50 step steepest descent, 200 step conjugate gradient followed by a 300 step Powell minimisation. The final structures were examined to obtain a mean pairwise rms difference over the backbone heavy atoms (N, Cα and C). Twenty of the 50 structures had a mean rmsd<0.5 Å for all backbone atoms (O, N, C).

Receptor-Binding Assay

Assays were performed with fresh human PMNs, isolated as previously described (Sanderson et al, 1995), using a buffer of 50 mM HEPES, 1 mM $CaCl_2$, 5 mM $MgCl_2$, 0.5% bovine serum albumin, 0.1% bacitracin and 100 µM phenylmethylsulfonyl fluoride (PMSF). In assays performed at 4° C., buffer, unlabelled human recombinant C5a (Sigma) or peptide, Hunter/Bolton labelled $^{125}$T-C5a (~20 pM) (New England Nuclear, MA) and PMNs ($0.2 \times 10^6$) were added sequentially to a Millipore Multiscreen assay plate (HV 0.45) having a final volume of 200 µL/well. After incubation for 60 min at 4° C., the samples were filtered and the plate washed once with buffer. Filters were dried, punched and counted in an LKB gamma counter. Non-specific binding was assessed by the inclusion of 1 mM peptide or 100 nM C5a, which typically resulted in 10-15% total binding.

Data was analysed using non-linear regression and statistics with Dunnett post-test.

Myeloperoxidase Release Assay for Antagonist Activity

Cells were isolated as previously described (Sanderson et al, 1995) and incubated with cytochalasin B (5 µg/mL, 15 min, 37° C.). Hank's Balanced Salt solution containing 0.15% gelatin and peptide was added on to a 96 well plate (total volume 100 µL/well), followed by 25 µL cells ($4 \times 10^6$/mL). To assess the capacity of each peptide to antagonise C5a, cells were incubated for 5 min at 37° C. with each peptide, followed by addition of C5a (100 nM) and further incubation for 5 min. Then 50 µL of sodium phosphate (0.1M, pH 6.8) was added to each well, the plate was cooled to room temperature, and 25 µL of a fresh mixture of equal volumes of dimethoxybenzidine (5.7 mg/mL) and $H_2O_2$ (0.51%) was added to each well. The reaction was stopped at 10 min by addition of 2% sodium azide. Absorbances were measured at 450 nm in a Bioscan 450 plate reader, corrected for control values (no peptide), and analysed by non-linear regression.

In Vivo Assays of Anti-Inflammatory Activity

The following well-known in vivo assay systems are used to assess the anti-inflammatory activity of compounds of the invention. All assay data are analysed using non-linear regression analysis and Student's t-test, analysis of variance, with p<0.05 as the threshold level of significance.

(a) Carrageenan Paw Oedema

Anaesthetised (i.p. ketamine & xylazine) Wistar rats (150-200 g) or mice are injected with sterilised air (20 ml day 1, 10 ml day 4) into the subcutaneous tissue of the back. The cavity can be used after 6 days, whereupon carrageenan (2 ml, 1% w/w in 0.9% saline) is injected into the air pouch, and exudate is collected after 10 hr. Test compounds are administered daily after Day 6, and their anti-inflammatory effects assayed by differential counting of cells in the air-pouch exudate. Animals are killed at appropriate times after injection, and 2 ml 0.9% saline is used to lavage the cavity; lavage fluids are transferred to heparinised tube and cells are counted with a haemocytometer and Diff-Quik stained cytocentrifuged preparation.

Alternatively, a routine carrageenan paw oedema developed in Wistar rats by administering a pedal injection of carrageenan may be used to elicit oedema which is visible in 2 h and maximised in 4 h. Test compounds are given 40 min before inflammagen and evaluated by microcaliper measurements of paws after 2 & 4 hr. See Fairlie, D. P. et al (1987). Also see Walker and Whitehouse (1978).

(b) Adjuvant Arthritis.

Adjuvant arthritis is induced in rats (3 strains) either immunologically (injection of heat-killed *Mycobacterium tuberculosis*) or chemically (with avridine) by inoculation with the arthritogenic adjuvant co-administered with oily vehicles, such as Freund's adjuvants in the tail base (See Whitehouse, M. W., Handbook of Animal Models for the Rheumatic Diseases, Eds Greenwald, R. A.; Diamond, H. S.; Vol. 1, pp. 3-16, CRC Press).

Within 13 days the adjuvant arthritis is manifested by local inflammation and ulceration in the tail, gross swelling of all four paws, inflammatory lesions in paws and ears, weight loss and fever. These symptoms, which are similar to those of inflammatory disease in humans (Winter and Nuss, 1966), can be alleviated by agents such as indomethacin or cyclosporin, which also show beneficial effects in man (eg. Ward and Cloud, 1966). Without drug treatment at Day 14, arthritic rats had hypertrophy of the paws, reduced albumin but raised acute phase reaction proteins in serum, and depressed hepatic metabolism of xenobiotics as indicated by prolonged barbiturate-induced sleeping times.

To assess activity, compounds are administered for 4 days orally ($\leq 10$ mg/kg/day) or intraperitoneally (i.p.) from Days 10-13 following inoculation with arthritogen (Day 0). If the compound is active, the inflammation is either not visible, or is very significantly reduced in rear or front paws, as assessed by microcaliper measurements of paw thickness and tail volume, as well as by gross inspection of inflammatory lesions. Animals are sacrificed by cervical dislocation on Day 18 unless arthritis signs are absent, whereupon duration of observations is continued with special permission from the Ethics Committees. Experiments are staggered to maximise throughput and allow early comparisons between compounds. This routine assay is well-accepted as identifying anti-inflammatory agents for use in humans.

Pharmacokinetics

Female and male Wistar rats (200-250 g) were anaesthetized with 1 mL of zoletil (50 mg/kg) and xylazine (10 mg/kg; Lyppard, Australia), which was injected intraperitoneally. An area of $5 \times 10$ cm was shaved and marked on the lower abdominal area of the rat, on to which the dose of drug was applied. A stock solution containing 10 mg/ml of C5a antagonist was dissolved in solvents propylene glycol or dimethylsulfoxide at varying concentrations with water and smeared evenly on the shaved abdominal area of the rat with a spatula. A heating pad was used to maintain the body temperature of the rats and blood samoles were taken at 15 min intervals for the first hour, and after that at 1 hr intervals for a total period or 3 hours.

Blood samples were immediately added to tubes containing heparin (500 Units/µL) and centrifuged (11000×g). The plasma layer of each sample was removed and stored at −20° C. A deuterated internal standard, $^2H_3CO$—F-[OPdChaWR] 50 µL, 5 µg/mL in 50% acetonitrile/water), was added and vortexed. The samples were further diluted 1:3 with high performance liquid chromatography (HPLC) grade acetonitrile and rapidly vortexed (20 sec), then centrifuged (11000× g). This process resulted in precipitation of large plasma proteins in the samples, and allowed the complete extraction of the drug from the plasma. The fluid portions of the samples were placed in 1 mL Eppendorf tubes and stored until analysed.

These samples were transferred to 96 well plates and evaporated to dryness using a GeneVac centrifugal evaporator, then reconstituted in the wells with mobile phase (20 µL) Analysis of samples was performed by liquid chromatography (LCMS) using an Agilent 1100 series HPLC equipped with a well plate autosampler coupled with a PE Sciex Qstar Pulsar ESI-TOF mass spectrometer. Concentrations were determined from a standard curve of drug:internal standard peak area ratios. Standards were prepared by adding an appropriate amount of the drug and internal standard to plasma from an untreated rat, and were extracted and prepared by the sane method as the experimental samples.

EXAMPLE 1

Synthesis of Cyclic Compounds

Synthesis of cycle AcF-[OPdChaWR] (1). The linear peptide Ac-Phe-Orn-Pro-dCha-Trp-Arg was synthesised by Boc chemistry on a 0.20 mmole scale using HBTU/DIEA activation and in situ neutralisation on a Boc-L-Arg(Tos)-PAM resin (338 mg, SV=0.591 mmol/g). Cleavage and deprotection of the resin (457 mg) was achieved by treating the resin with HF (10 ml) and p-cresol (1 ml) at −5 to 0° C. for 1-2 hrs, to give crude peptide (160 mg, 90%). Cyclisation involved stirring the crude peptide (41 mg, 45 μmol), BOP (126 mg, 0.28 mmol) and DIEA (158 μL, 0.9 mmol) in DMF (57 mL) for 15 hrs. The solvent was removed in vacuo and the cyclic peptide purified by rpHPLC (18.8 mg, 47%) Rt=10.8 min (gradient 70% A/30% B to 0% A/100% B over 30 min). MS: [M+H]+ (calc.)=896.5, [M+H]+ (exper.)=896.5.

Synthesis of cycle AcF-[OPdPheWR] (33). The linear peptide Ac-Phe-Orn-Pro-dPhe-Trp-Arg was synthesised by Boc chemistry using HBTU/DIEA activation and in situ neutralisation on a Boc-L-Arg(Tos)-PAM resin. Cleavage and deprotection of the resin was achieved by treating the resin with HF (10 ml) and p-cresol (1 ml) at −5 to 0° C. for 1-2 hrs, to give crude peptide. Cyclisation involved stirring the crude peptide (85 mg), BOP (200 mg) and DIEA (222 μL) in DMF (10 mL) for 15 hrs. The solvent was removed in vacuo and the cyclic peptide purified by rpHPLC (31 mg) Rt=16.7 min (gradient: 70% A/30% B to 0% A/100% B over 30 min). MS: [M+H]+ (calc.)=890.5, [M+H]+ (exper.)=890.5.

Synthesis of cycle AcF-[OPdChaFR] (60). The linear peptide Ac-Phe-Orn-Pro-dCha-Phe-Arg was synthesised by Boc chemistry using HBTU/DIEA activation and in situ neutralisation on a Boc-L-Arg(Tos)-PAM resin. Cleavage and deprotection of the resin was achieved by treating the resin with HF (10 ml) and p-cresol (1 ml) at −5 to 0° C. for 1-2 hrs, to give crude peptide. Cyclisation involved stirring the crude peptide (104 mg), BOP (57 mg) and DIEA (103 μL) in DMF (1 mL) for 15 hrs. The solvent was removed in vacuo and the cyclic peptide purified by rpHPLC (52 mg). Rt=11.37 min (gradient: 70% A/30% B to 0% A/100% SB over 15 min). MS: [M+H]+ (calc.)=857.5, [M+H]+ (exper.)=857.4.

Synthesis of cycle AcF-[OPdCha(N-Me-Phe)R] (64). The linear peptide Ac-Phe-Orn-Pro-dCha-(N-Me-Phe)-Arg-OH was synthesised by Fmoc chemistry using HBTU/DIEA activation and in situ neutralisation on a Fmoc-L-Arg(pbf)-Wang resin (0.35 mmol/g) from Novabiochem using methyl-L-Phe (281 mg, 2 equiv), Fmoc-dCha (275 mg, 2 equiv), Fmoc-Pro (472 mg, 4 equiv), Fmoc-Orn(Boc) (477 mg, 3 equiv), Fmoc-Phe (542 mg, 4 equiv) and Ac2O (4 equiv). Cleavage and deprotection of the resin was achieved by treating the resin with 95% TFA (15 mL) for 1 h to give crude peptide (150 mg) after precipitation with diethyl ether Cyclisation involved stirring the rpHPLC purified peptide (100 mg), BOP (20 mg) and DIEA (222 μL) in DMF (2 mL) for 4 hrs. The solvent was removed in vacuo and the cyclic peptide purified by rpHPLC (50 mg) Rt=33 min (gradient: 70% A/30% B to 0% A/100% B over 30 min). MS: [M+H]+ (calc.)=871.5, [M+H]+ (exper.)=871.5.

Synthesis of cycle AcF-[{Orn-(δN-Me)}PdChaWR] (66). Boc-(δN-Me-Orn)-OH was synthesized as reported (Pol. J. Chem. 1988, 62, 257-261). The linear peptide Ac-Phe-[Orn-(δN-MeCbz)]-Pro-dCha-Trp-Arg-OH was synthesised by Boc chemistry using HBTU/DIEA activation and in situ neutralisation on Boc-L-Arg(tosyl)Pam resin (0.41 mmol/g) from Novabiochem. Cleavage and deprotection of the resin was achieved by treating the resin with HF/pCresol for 2 h to give crude peptide after precipitation with diethyl ether. Cyclisation involved stirring the RP-HPLC purified peptide (100 mg), BOP (200 mg) and DIEA (222 μL) in DMF (2 mL) for 4 hrs. The solvent was removed in vacuo and the cyclic peptide purified by rpHPLC. Rt=11.5 min (35% B). MS: [M+H]+ (calc.)=910.5, [M+H]+ (exper.)=910.5.

Purification and Characterisation.

Crude peptides were purified using preparative rp-HPLC using a Vydac C18 reverse-phase column (2.2×25 cm). Gradients of 1 mL/min of solvent A to solvent B were employed and monitored at 214 nm. Fractions were collected and tested by ion spray mass spectrometry (ISMS) for the correct molecular weight, and purity was checked by analytical rp-HPLC on a Waters Delta-Pak PrepPak CIS reverse-phase column (0.8×10 cm) (varying gradients such as: 0 to 75% B over 60 min). The acetonitrile was HPLC grade (BDH Laboratories) and TFA was synthesis grade (Auspep).

Table 1 shows examples of reactions used to prepare cyclic compounds 1-70, and their characterisation by electrospray mass specrometry (Mass Spec Found) and reversed phase HPLC (rp-HPLC) retention times (Rt mins) under specified elution conditions.

Table 2 depicts the structures of the respective compounds, and lists their respective receptor binding affinities and antagonist potencies for the C5a receptor on human polymorphonuclear leukocytes (neutrophils), as measured by myeloperoxidase assay.

TABLE 1

Summary Of Synthesis and Characterisation Of Cyclic Compounds listed in Table 2

| Compound | Amount Linear Peptide | Amount BOP | Amount DIPEA | Amount DMF | Yield Cycle | Mass Spec Calcd | Mass Spec Found | rpHPLC conditions | rpHPLC Rt (min) |
|---|---|---|---|---|---|---|---|---|---|
| 1 | 41 mg | 126 mg | 158 μL | 57 mL | 19 mg | 895.5 | 896.5 | 30→100% B 30 m | 10.8 |
| 2 | | | | | | 957.5 | 958.5 | 30→100% B 30 m | 14.8 |
| 3 | 78 mg | 36 mg | 71 μL | 1 mL | 29 mg | 937.6 | 938.5 | 30→100% B 30 m | 13.1 |
| 4 | 65 mg | 29 mg | 57 μL | 1 mL | | 966.6 | 967.5 | 15→100% B 60 m | 18.5-20.5 |
| 5 | 81 mg | 36 mg | 71 μL | 1 mL | | 967.5 | 968.5 | 30→100% B 90 m | 23.2 |
| 6 | 25 mg | — | 0.25 mL 2M NaOH | 0.5 mL MeOH | Quantitative | | | As above | 19.3 |
| 7 | 92 mg | 200 mg | 222 μL | 10 mL | 29 mg | 910.5 | 910.3 | 30→100% B 30 m | 23.0-23.8 |
| 8 | 87 mg | 200 mg | 222 μL | 10 mL | 18 mg | 896.5 | 898.4 | 30→100% B 30 m | 13.1-14.2 |
| 9 | 55 mg | 200 mg | 222 μL | 10 mL | 5 mg | 912.5 | 912.5 | 30→100% B 30 m | 3.2-4.2 |

TABLE 1-continued

Summary Of Synthesis and Characterisation Of Cyclic Compounds listed in Table 2

| Compound | Amount Linear Peptide | Amount BOP | Amount DIPEA | Amount DMF | Yield Cycle | Mass Spec Calcd | Mass Spec Found | rpHPLC conditions | rpHPLC Rt (min) |
|---|---|---|---|---|---|---|---|---|---|
| 10 | 105 mg | 200 mg | 222 µL | 10 mL | 51 mg | 932.5 | 932.7 | 30→100% B 30 m | 6.0-8.2 |
| 11 | 88 mg | 200 mg | 222 µL | 10 mL | 27 mg | 1008.5 | 1008.7 | 30→100% B 30 m | 10.4-11.7 |
| 12 | 72 mg | 200 mg | 222 µL | 10 mL | 15 mg | 882.5 | 882.5 | 30→100% B 30 m | 7.0-8.0 |
| 13 | 53 mg | 28 mg | 56 µL | 1 mL | 21 mg | 805.5 | 806.5 | 30→100% B 60 m | 7.6 |
| 14 | 51 mg | 200 mg | 222 µL | 10 mL | 12 mg | 914.5 | 914.5 | 30→100% B 30 m | 8.6-9.4 |
| 15 | 90 mg | 200 mg | 222 µL | 10 mL | 33 mg | 914.5 | 914.5 | 30→100% B 30 m | 7.3-8.5 |
| 16 | 81 mg | 200 mg | 222 µL | 10 mL | 22 mg | 935.5 | 935.5 | 30→100% B 30 m | 21.8-22.2 |
| 17 | 90 mg | 46 mg | 91 µL | 1 mL | 46 mg | 838.5 | 839.4 | 30→100% B 60 m | 13.4-17 |
| 18 | 60 mg | 31 mg | 61 µL | 1 mL | 25 mg | 836.5 | 837.4 | 30→100% B 60 m | 15.1-18 |
| 19 | 53 mg | 33 mg | 65 µL | 1 mL |  | 691.4 | 692.4 | 30→100% B 60 m | 9-10.5 |
| 20 | 66 mg | 200 mg | 222 µL | 10 mL | 15 mg | 898.5 | 898.5 | 30→100% B 30 m | 14.2-14.7 |
| 21 | 81 mg | 200 mg | 222 µL | 10 mL | 22 mg | 912.5 | 912.5 | 30→100% B 30 m | 17.2-18.0 |
| 22 | 59 mg | 200 mg | 222 µL | 10 mL | 20 mg | 945.5 | 946.7 | 30→100% B 30 m |  |
| 24 | 110 mg | 200 mg | 222 µL | 10 mL | 37 mg | 952.6 | 952.4 | 30→100% B 30 m | 16.7-17.2 |
| 25 | 82 mg | 200 mg | 222 µL | 10 mL | 20 mg | 912.5 | 912.5 | 30→100% B 30 m | 7.2-8.3 |
| 26 | 71 mg | 200 mg | 222 µL | 10 mL | 16 mg | 928.5 | 928.5 | 30→100% B 30 m | 6.7-7.6 |
| 27 | 75 mg | 200 mg | 222 µL | 10 mL | 21 mg | 896.5 | 896.7 | 30→100% B 30 m | 25.9-26.3 |
| 28 | 130 mg | 62 mg | 122 µL | 2 mL | 90 mg | 909.5 | 910.4 | 30→100% B 60 m | 14.6-17.6 |
| 29 | 143 mg | 73 mg | 144 µL | 2 mL | 60 mg | 841.4 | 842.5 | 30→100% B 60 m | 7.4-8.9 |
| 30 | 135 mg | 72 mg | 142 µL | 2 mL |  | 813.4 | 814.4 | 10→100% B 60 m | 16.8-18.6 |
| 31 | 102 mg | 52 mg | 101 µL | 1 mL |  | 855.5 | 856.6 | 30→100% B 60 m | 8.2-9.7 |
| 32 | 49 mg | 200 mg | 222 µL | 10 mL | 8 mg | 928.5 | 929.6 | 30→100% B 30 m | 12.7-13.7 |
| 33 | 85 mg | 200 mg | 222 µL | 10 mL | 31 mg | 889.5 | 890.5 | 30→100% B 30 m | 16.5-16.9 |
| 34 | 122 mg | 57 mg | 113 µL | 2 mL |  | 901.5 | 902.2 | 30→100% B 15 m | 6.0 |
| 35 | 106 mg | 49 mg | 95 µL | 2 mL |  | 901.5 | 902.2 | 30→100% B 15 m | 10.7 |
| 36 | 120 mg | 61 mg | 122 µL | 2 mL |  | 855.5 | 856.4 | 30→100% B 60 m | 9.2-10.7 |
| 39 | 70 mg | 200 mg | 222 µL | 10 mL | 28 mg | 906.5 | 906.7 | 30→100% B 60 m |  |
| 40 | 62 mg | 34 mg | 66 µL | 1 mL |  | 799.4 | 800.6 | 20→100% B 60 m | 9-9.7 |
| 44 | 100 mg | 48 mg | 93 µL | 1 mL |  | 909.5 | 910.6 | 30→100% B 60 m | 13.4-16.3 |
| 45 | 94 mg | 45 mg | 89 µL | 1 mL |  | 896.5 | 897.8 | 30→100% B 60 m | 14.0-15.2 |
| 49 | 55 mg | 29 mg | 58 µL | 1 mL |  | 796.4 | 797.4 | 30→100% B 60 m | 17.2-18.6 |
| 50 | 75 mg | 30 mg | 0.06 mL | 1 mL | 35 mg | 862.5 | 863.7 | 30→100% B 90 m | 21-23 |
| 51 | 64 mg | 27 mg | 0.05 mL | 1 mL | 25 mg | 822.5 | 823.7 | 30→100% B 90 m | 14.5-17 |
| 52 | 196 mg | 94 mg | 184 µL | 2 mL | 67 mg | 906.5 | 907.5 | 30→100% B 60 m | 17-18.4 |
| 53 | 177 mg | 84 mg | 166 µL | 2 mL |  | 906.5 | 907.6 | 30→100% B 60 m | 16.1-20.4 |
| 54 | 79 mg | 200 mg | 222 µL | 10 mL | 22 mg | 944.5 | 945.5 | 30→100% B 30 m |  |
| 56 | 161 mg | 79 mg | 156 µL | 2 mL |  | 868.5 | 869.2 | 30→100% B 60 m |  |
| 57 | 70 mg | 39 mg | 70 µL | 1 mL |  | 846.5 | 847.4 | 10→100% B 60 m | 15.3-17.6 |
| 58 | 160 mg | 76 mg | 150 µL | 2 mL |  | 912.5 | 913.3 | 30→100% B 60 m | 15.4-19.6 |
| 59 | 150 mg | 73 mg | 143 µL | 2 mL |  | 895.5 | 896.6 | 30→100% B 15 m | 10.4 |
| 60 |  |  |  |  |  | 856.5 | 857.4 | 30→100% B 15 m | 11.4 |
| 61 | 160 mg | 80 mg | 156 µL | 2 mL |  | 870.5 | 871.4 | 30→100% B 60 m | 13.9-17.4 |
| 62 | 180 mg | 91 mg | 180 µL | 2 mL | 84 mg | 850.4 | 851.4 | 30→100% B 60 m | 8.9-11.3 |
| 63 | 174 mg | 83 mg | 164 µL | 2 mL | 75 mg | 900.5 | 901.4 | 30→100% B 60 m | 13.4-15.3 |
| 64 | 100 mg | 200 mg | 222 µL | 2 mL | 50 mg | 870.5 | 871.5 | 30→100% B 60 m | 33.0 |
| 65 | 100 mg | 200 mg | 222 µL | 2 mL |  | 903.5 | 904.5 | 35% B | 8.2 |
| 66 | 100 mg | 200 mg | 222 µL | 2 mL |  | 909.5 | 910.5 | 35% B | 11.5 |
| 67 | 50 mg | 50 mg | 100 µL | 5 mL | 22 mg | 861.6 | 862.6 | 30→100% B 30 m | 20.5 |
| 68 | 50 mg | 50 mg | 100 µL | 5 mL | 18 mg | 881.5 | 882.4 | 30→100% B 30 m | 29.5 |
| 69 | 50 mg | 50 mg | 100 µL | 5 mL | 19 mg | 863.0 | 864.0 | 30→100% B 30 m | 23.2 |
| 70 | 50 mg | 50 mg | 100 µL | 5 mL | 4 mg* | 884.0 | 885.0 | 30→100% B 30 m | 29.5 |

*Tyr-O-Benzyl was the amino acid used, but the product involved a rearrangement to a meta-C-substituted tyrosine with a benzyl substituent (see structure of compound 70).

EXAMPLE 2

Antagonist Activity of Cyclic Compounds

Table 2 shows the structures of the compounds synthesised in Example 1, as well as their respective receptor binding affinities and antagonist potencies for the C5a receptor on human polymorphonuclear leukocytes (neutrophils), as measured by the myeloperoxidase assay.

Compounds 1-9, 16-18, 20, 21, 23, 24, 27-32, 36, 38, 44, 51, and 59 are within the broad scope of the general structure set out in our earlier patent application No. PCT/AU98/00490. However, Table 2 demonstrates that in fact, of these compounds, only 1-6, 17, 20, 28, 30, 31, 36 and 44 have appreciable antagonist potency (IC50<1 µM) against the C5a receptor on human neutrophils. The other compounds, 7-9, 16, 18, 21, 23, 24, 27, 29, 32, 38, 51, and 59, do not show appreciable antagonist potency and/or receptor affinity, with IC50>1 µM in all cases.

On the other hand, compounds 10-15, 19, 22, 25, 26, 33-35, 37, 39-43, 45, 47-50, 52-58, and 60-70 are not included within the scope of PCT/AU98/00490, although they do involve the same or similar cyclic scaffolds to those disclosed therein. Table 2 shows that of these new compounds, 10-12, 14, 15, 25, 33, 35, 40, 45, 48, 52, 58, 60, 66, and 68-70 have appreciable antagonist potency (IC50<1 µM). However, the other compounds (13, 19, 22, 26, 34, 37, 39, 41-43, 47, 49, 50, 53-57, 61-65, and 67) do not show appreciable antagonist potency and/or receptor affinity, with IC50>1 µM in all these cases.

The results shown in Table 2 enable us to define further and to refine the limitations on the active pharmacophore for C5a receptor antagonist activity, in order to obtain or predict sub-micromolar antagonist potency.

TABLE 2

Structures and Activities of 70 Examples Of Cyclic Antagonists of C5a Receptors on Human Polymorphonuclear Leukocytes. Examples of C5aR Antagonists

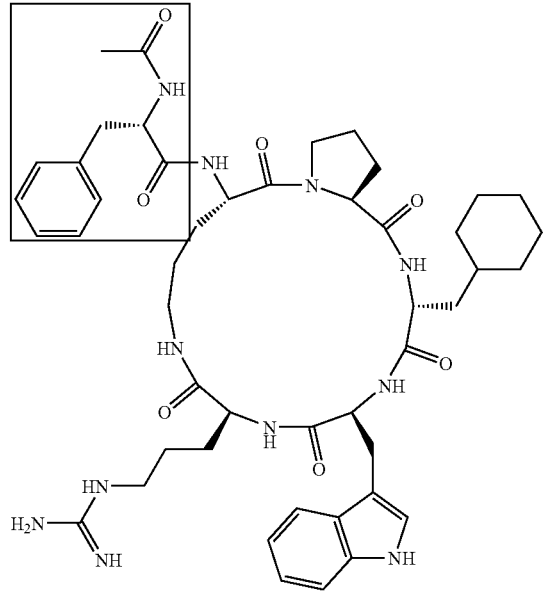

1
C5aR Binding IC50: 0.45 µM
C5aR Antagonist IC50: 28 nM

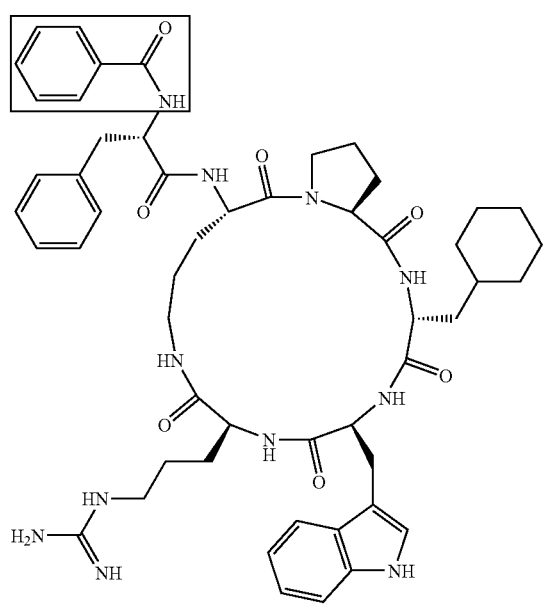

2
C5aR Binding IC50: 1.1 µM
C5aR Antagonist IC50: 110 nM

TABLE 2-continued

Structures and Activities of 70 Examples Of Cyclic Antagonists of C5a Receptors on Human Polymorphonuclear Leukocytes. Examples of C5aR Antagonists

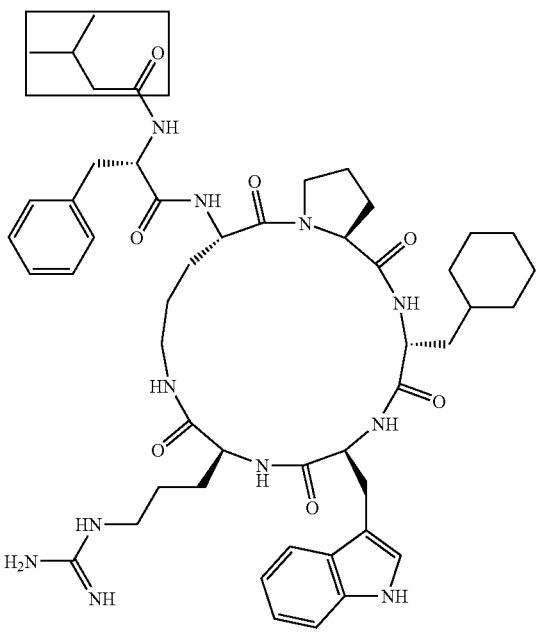

3
C5aR Binding IC50: 0.84 µM
C5aR Antagonist IC50: 30 nM

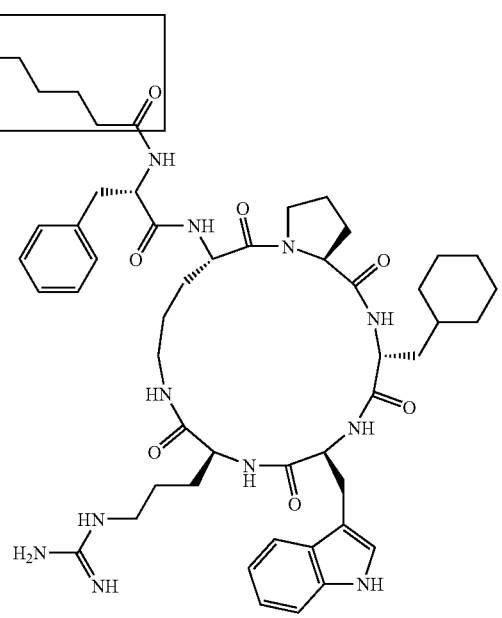

4
C5aR Binding IC50: 0.25 µM
C5aR Antagonist IC50: 62 nM

TABLE 2-continued

Structures and Activities of 70 Examples Of
Cyclic Antagonists of C5a Receptors on Human
Polymorphonuclear Leukocytes.
Examples of C5aR Antagonists

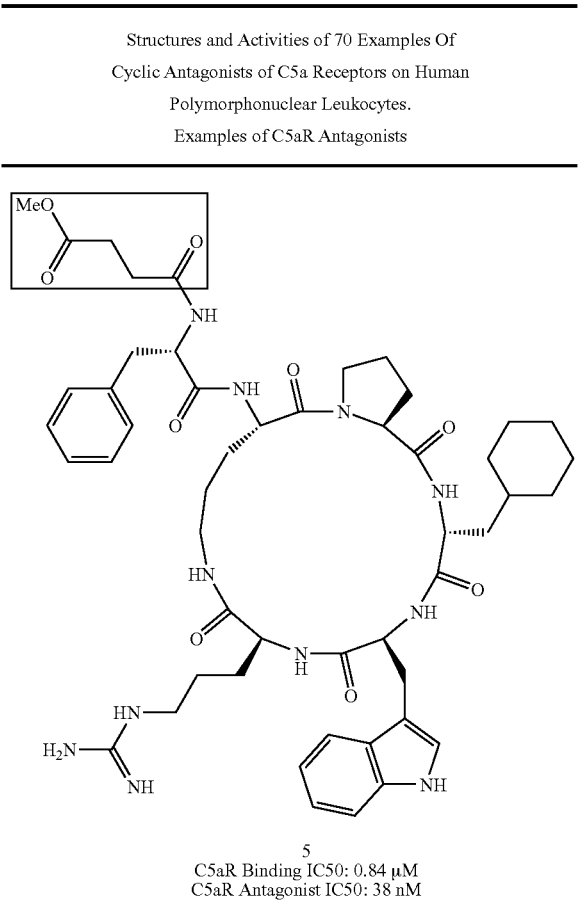

5
C5aR Binding IC50: 0.84 µM
C5aR Antagonist IC50: 38 nM

6
C5aR Binding IC50: 0.4 µM
C5aR Antagonist IC50: 23 nM

TABLE 2-continued

Structures and Activities of 70 Examples Of
Cyclic Antagonists of C5a Receptors on Human
Polymorphonuclear Leukocytes.
Examples of C5aR Antagonists

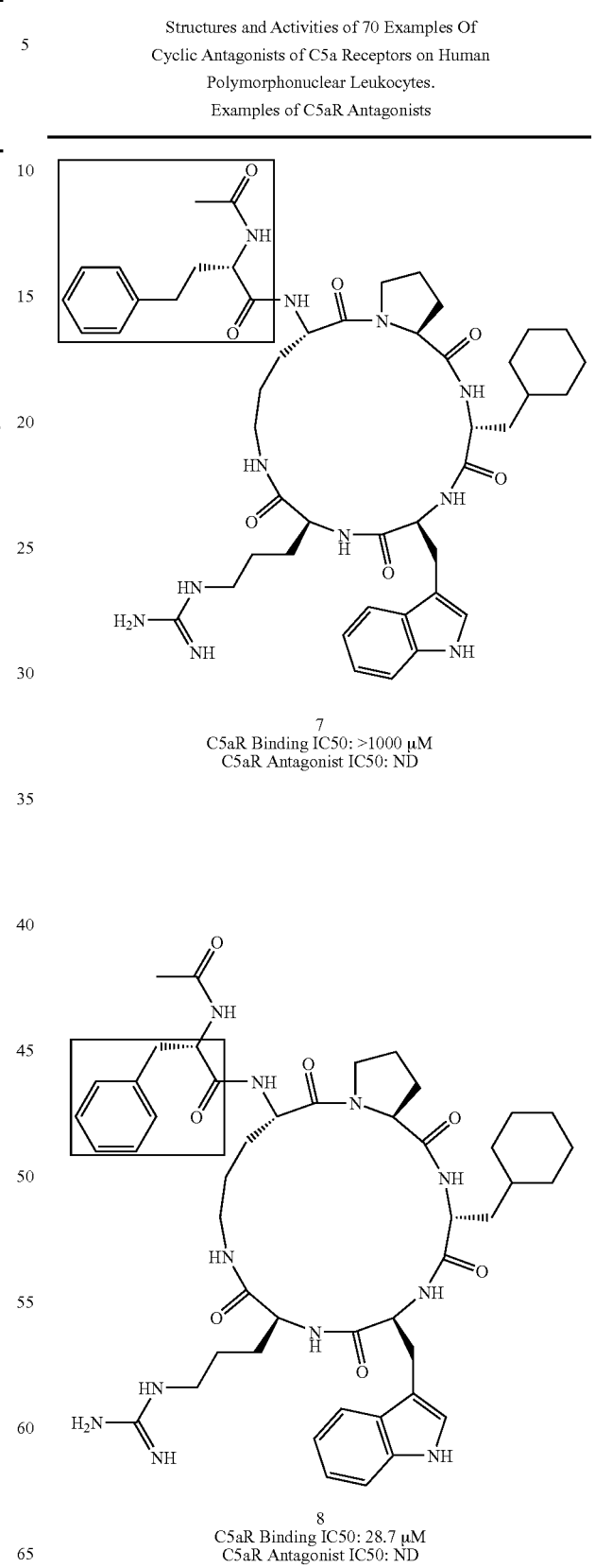

7
C5aR Binding IC50: >1000 µM
C5aR Antagonist IC50: ND

8
C5aR Binding IC50: 28.7 µM
C5aR Antagonist IC50: ND

TABLE 2-continued
Structures and Activities of 70 Examples Of
Cyclic Antagonists of C5a Receptors on Human
Polymorphonuclear Leukocytes.
Examples of C5aR Antagonists
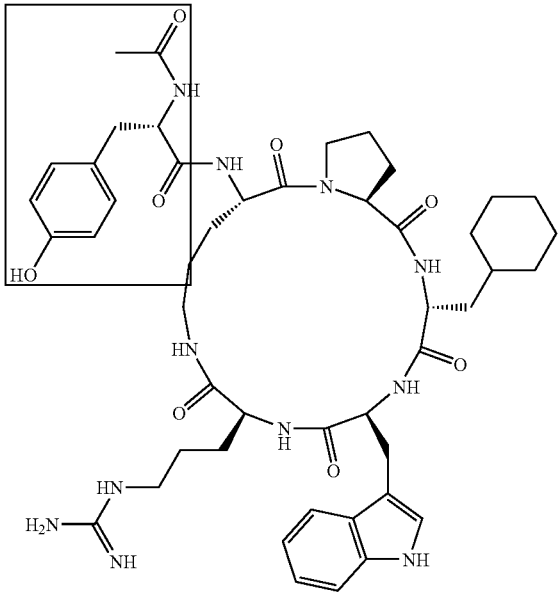
9
C5aR Binding IC50: 30 µM
C5aR Antagonist IC50: ND
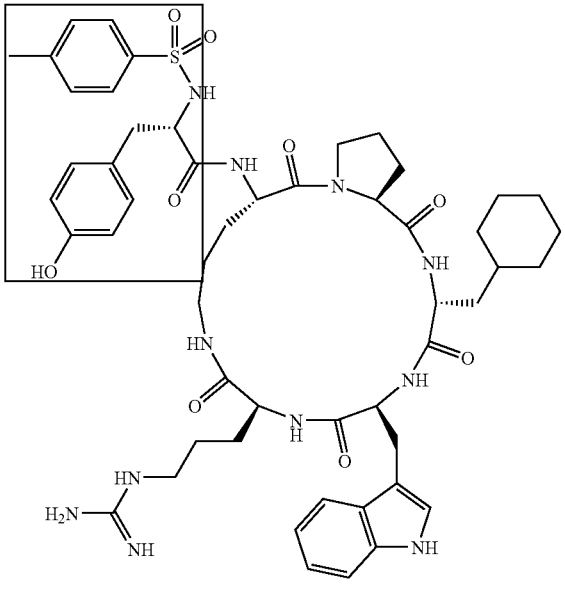
11
C5aR Binding IC50: 0.96 µM
C5aR Antagonist IC50: 291 nM
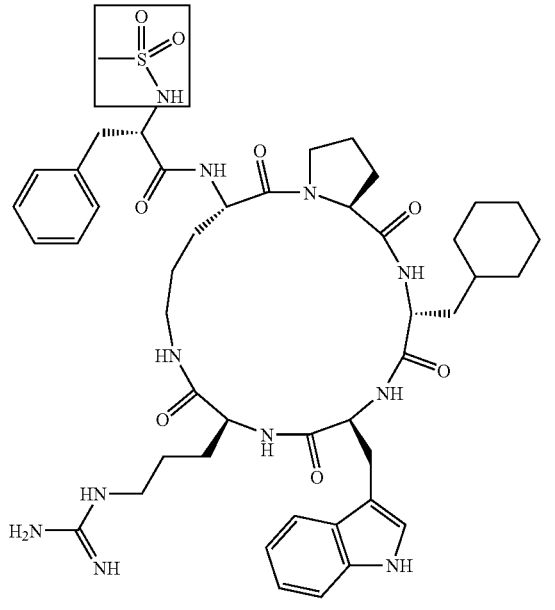
10
C5aR Binding IC50: 0.47 µM
C5aR Antagonist IC50: 34 nM
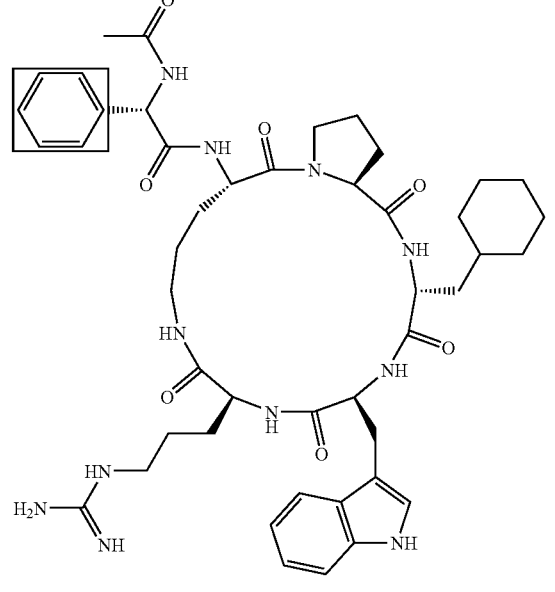
12
C5aR Binding IC50: 0.76 µM
C5aR Antagonist IC50: 151 nM

TABLE 2-continued
Structures and Activities of 70 Examples Of
Cyclic Antagonists of C5a Receptors on Human
Polymorphonuclear Leukocytes.
Examples of C5aR Antagonists
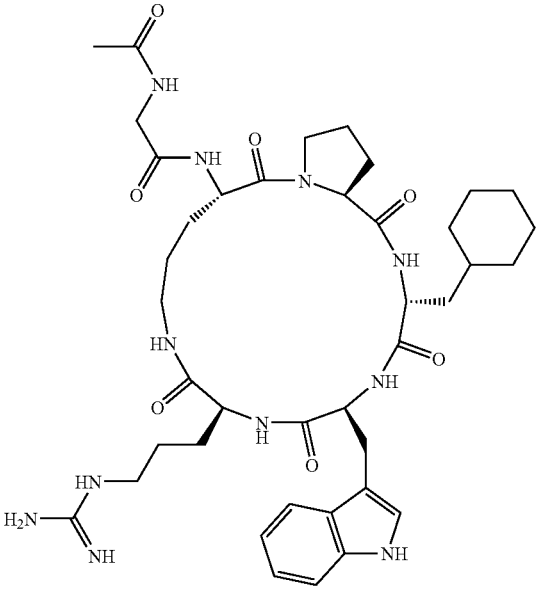
13
C5aR Binding IC50: 37 µM
C5aR Antagonist IC50: ND
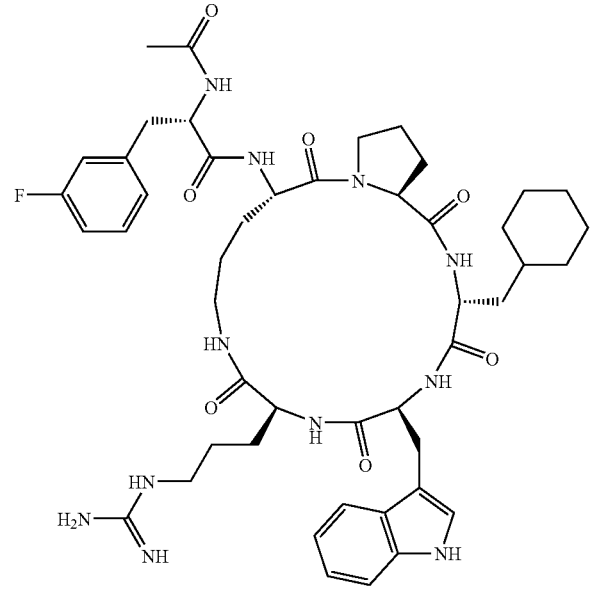
15
C5aR Binding IC50: 0.39 µM
C5aR Antagonist IC50: ND
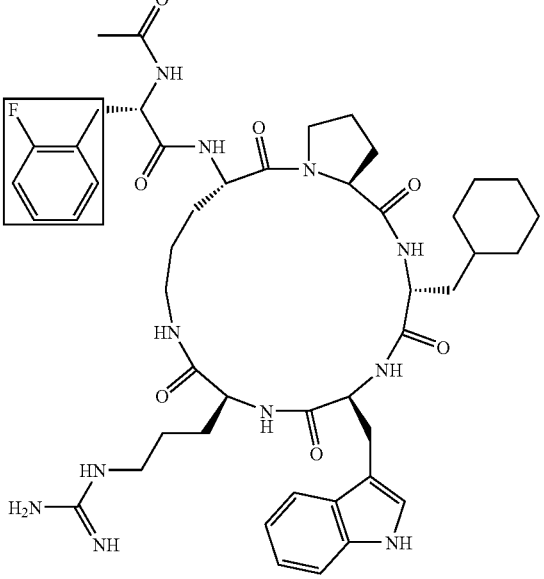
14
C5aR Binding IC50: 0.52 µM
C5aR Antagonist IC50: 38 nM
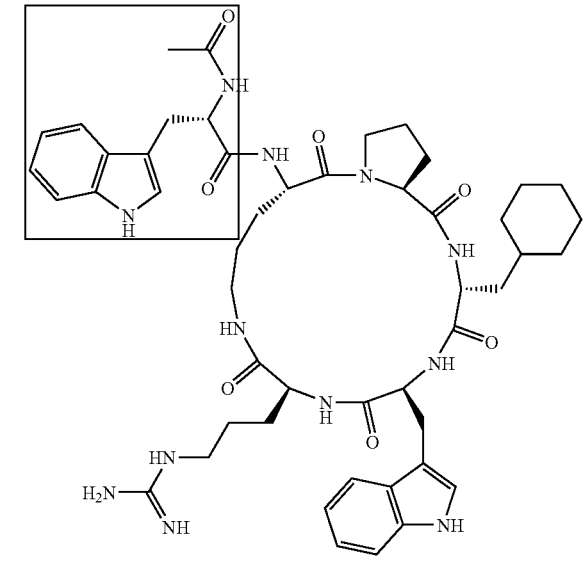
16
C5aR Binding IC50: 19.2 µM
C5aR Antagonist IC50: ND TABLE 2-continued Structures and Activities of 70 Examples Of
Cyclic Antagonists of C5a Receptors on Human
Polymorphonuclear Leukocytes.
Examples of C5aR Antagonists

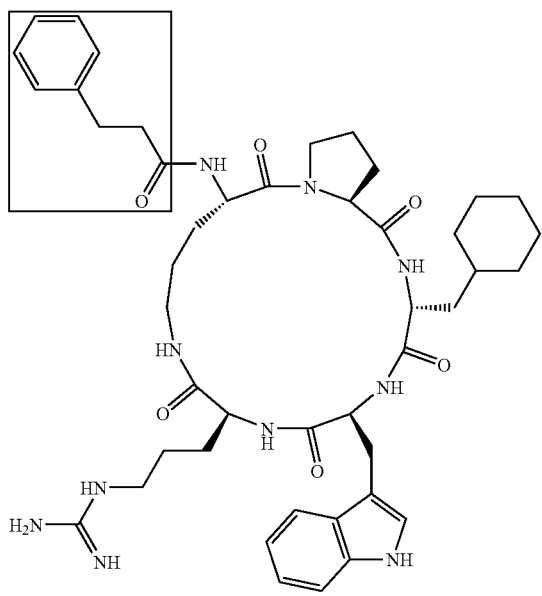

17
C5aR Binding IC50: 0.22 μM
C5aR Antagonist IC50: 31 nM

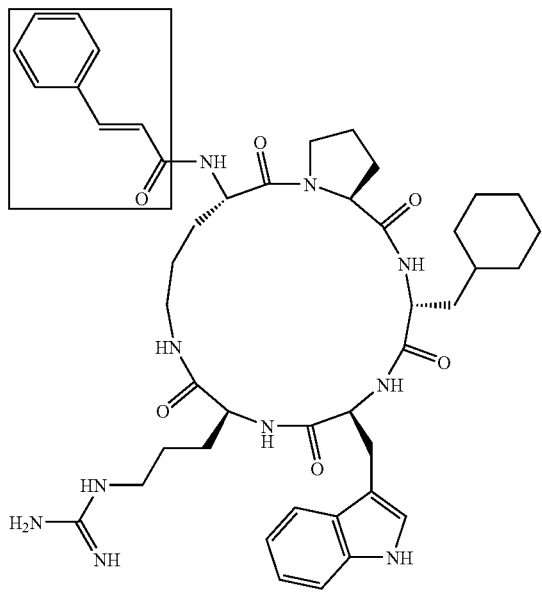

18
C5aR Binding IC50: 9.9 μM
C5aR Antagonist IC50: ND

TABLE 2-continued

Structures and Activities of 70 Examples Of
Cyclic Antagonists of C5a Receptors on Human
Polymorphonuclear Leukocytes.
Examples of C5aR Antagonists

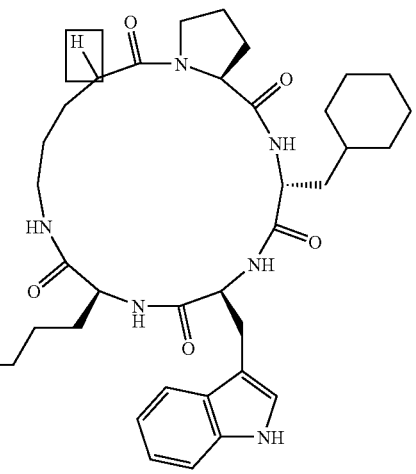

19
C5aR Binding IC50: 16.1 μM
C5aR Antagonist IC50: ND

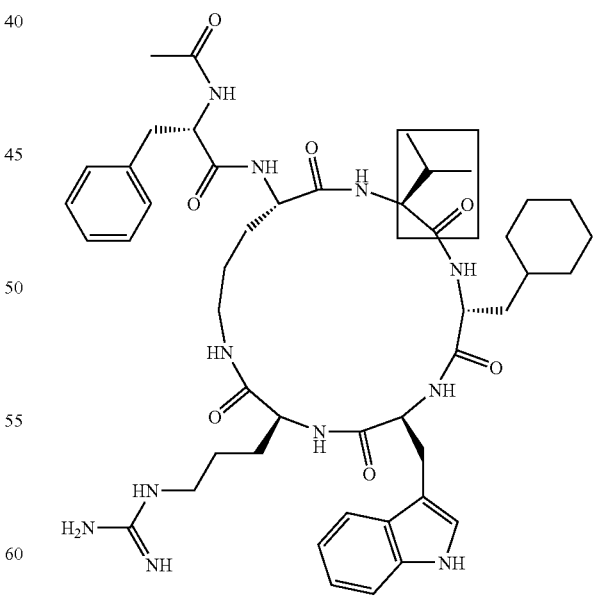

20
C5aR Binding IC50: 0.68 μM
C5aR Antagonist IC50: ND

TABLE 2-continued

Structures and Activities of 70 Examples Of
Cyclic Antagonists of C5a Receptors on Human
Polymorphonuclear Leukocytes.
Examples of C5aR Antagonists

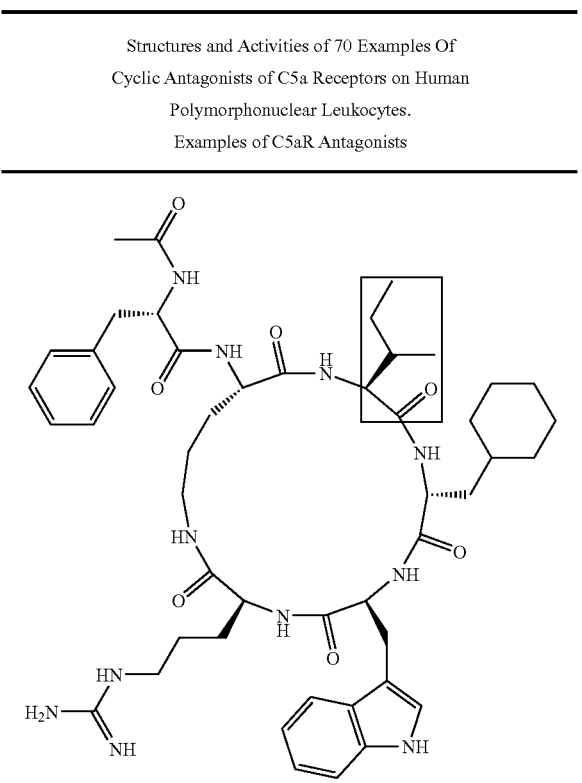

21
C5aR Binding IC50: 2.9 μM
C5aR Antagonist IC50: ND

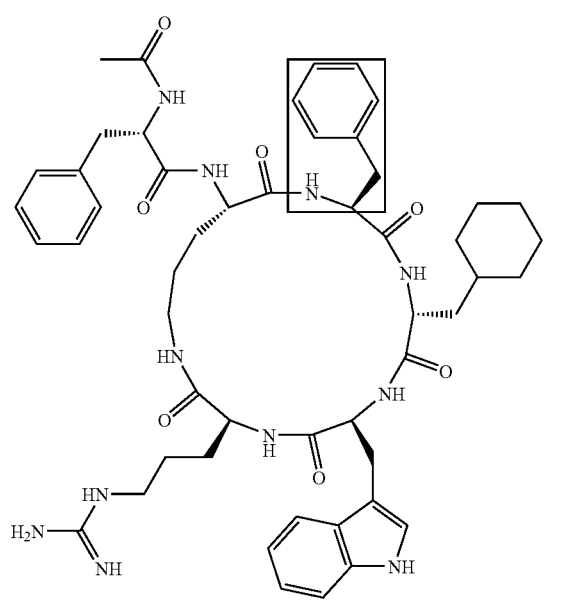

22
C5aR Binding IC50: 2.4 μM
C5aR Antagonist IC50: ND

TABLE 2-continued

Structures and Activities of 70 Examples Of
Cyclic Antagonists of C5a Receptors on Human
Polymorphonuclear Leukocytes.
Examples of C5aR Antagonists

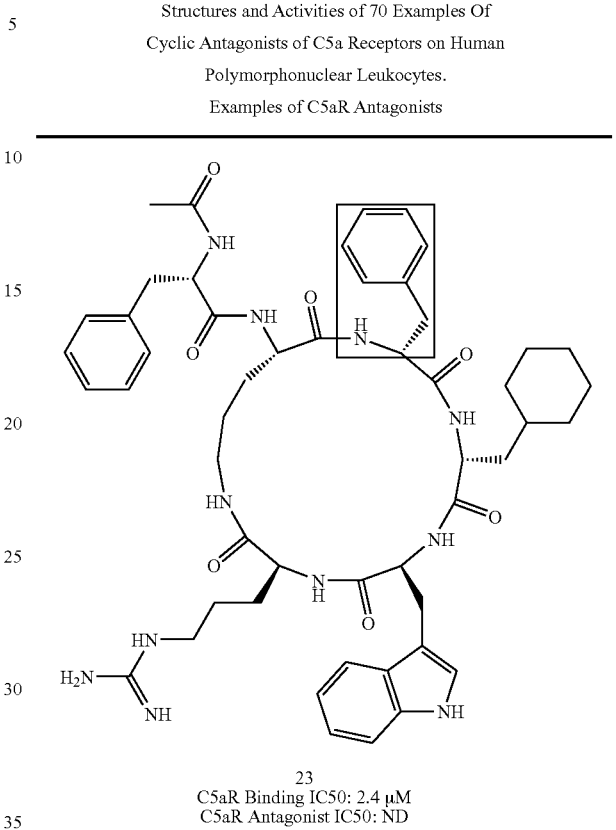

23
C5aR Binding IC50: 2.4 μM
C5aR Antagonist IC50: ND

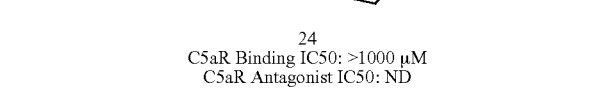

24
C5aR Binding IC50: >1000 μM
C5aR Antagonist IC50: ND

TABLE 2-continued

Structures and Activities of 70 Examples Of
Cyclic Antagonists of C5a Receptors on Human
Polymorphonuclear Leukocytes.
Examples of C5aR Antagonists

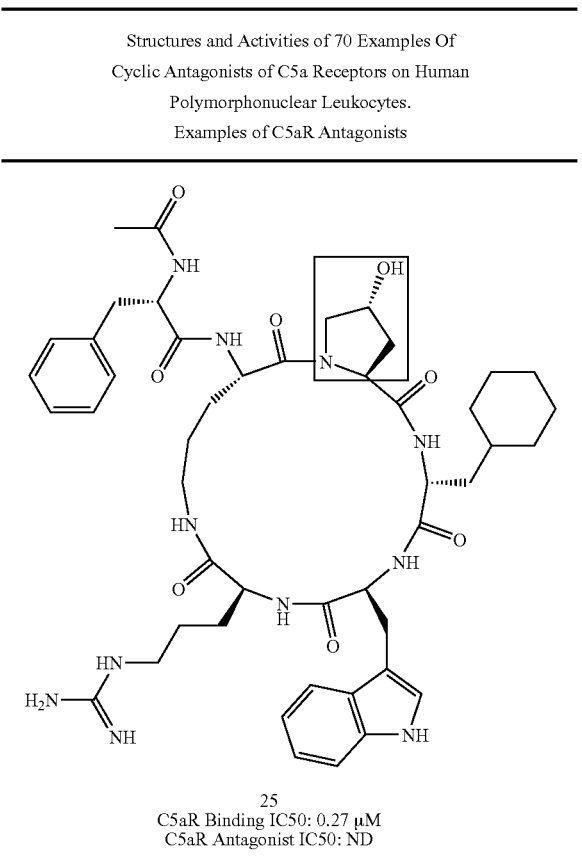

25
C5aR Binding IC50: 0.27 µM
C5aR Antagonist IC50: ND

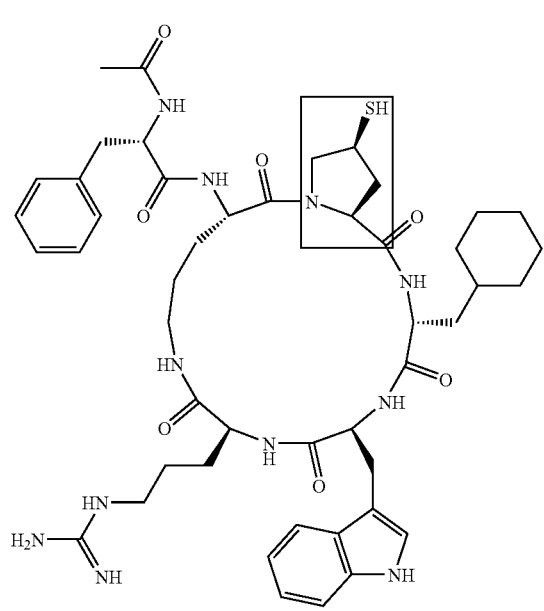

26
C5aR Binding IC50: 75.5 µM
C5aR Antagonist IC50: ND

TABLE 2-continued

Structures and Activities of 70 Examples Of
Cyclic Antagonists of C5a Receptors on Human
Polymorphonuclear Leukocytes.
Examples of C5aR Antagonists

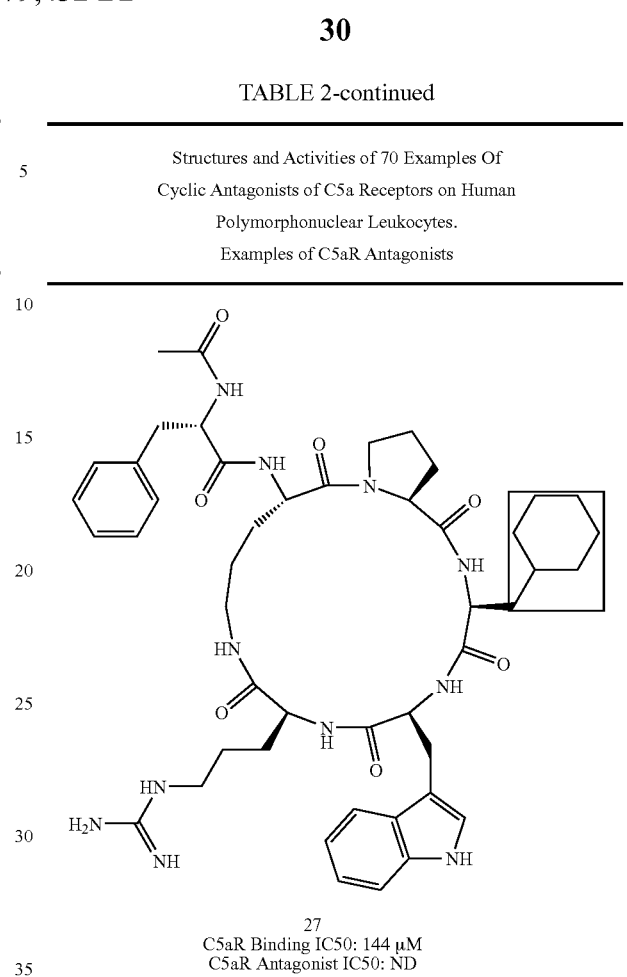

27
C5aR Binding IC50: 144 µM
C5aR Antagonist IC50: ND

28
C5aR Binding IC50: 0.30 µM
C5aR Antagonist IC50: 40 nM

TABLE 2-continued

Structures and Activities of 70 Examples Of
Cyclic Antagonists of C5a Receptors on Human
Polymorphonuclear Leukocytes.
Examples of C5aR Antagonists

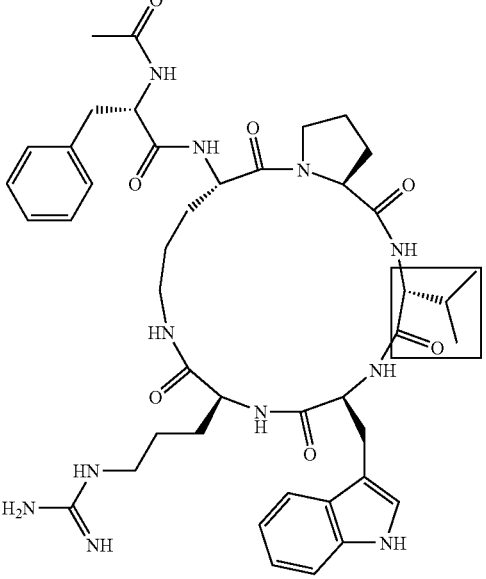

29
C5aR Binding IC50: 13 μM
C5aR Antagonist IC50: ND

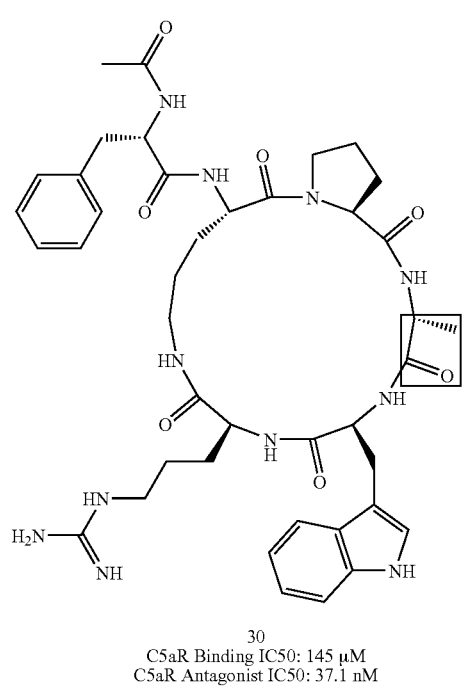

30
C5aR Binding IC50: 145 μM
C5aR Antagonist IC50: 37.1 nM

TABLE 2-continued

Structures and Activities of 70 Examples Of
Cyclic Antagonists of C5a Receptors on Human
Polymorphonuclear Leukocytes.
Examples of C5aR Antagonists

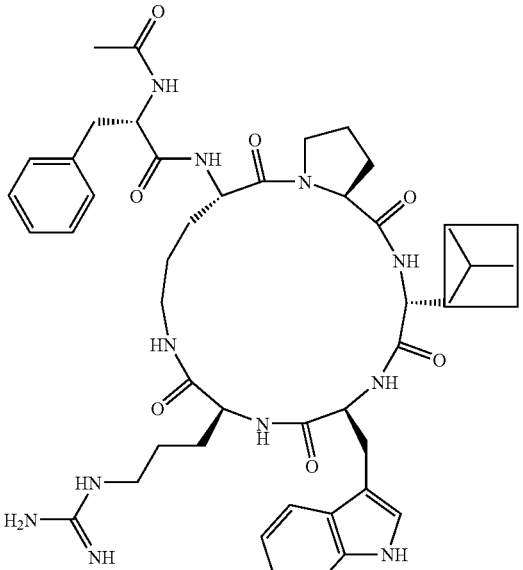

31
C5aR Binding IC50: 1.1 μM
C5aR Antagonist IC50: 35 nM

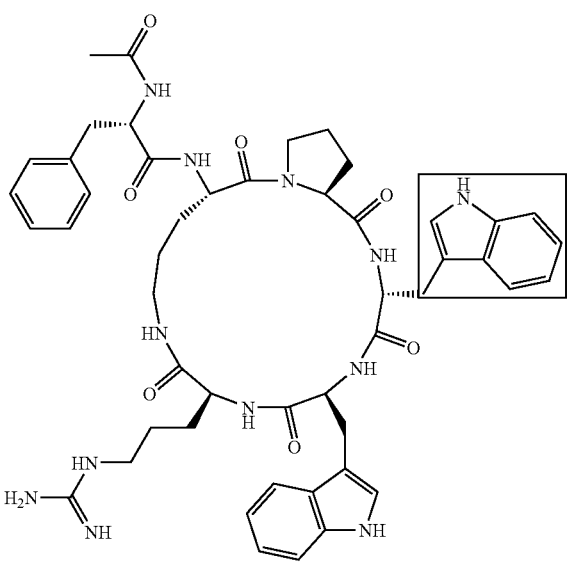

32
C5aR Binding IC50: 30.1 μM
C5aR Antagonist IC50: ND

TABLE 2-continued
Structures and Activities of 70 Examples Of Cyclic Antagonists of C5a Receptors on Human Polymorphonuclear Leukocytes.
Examples of C5aR Antagonists
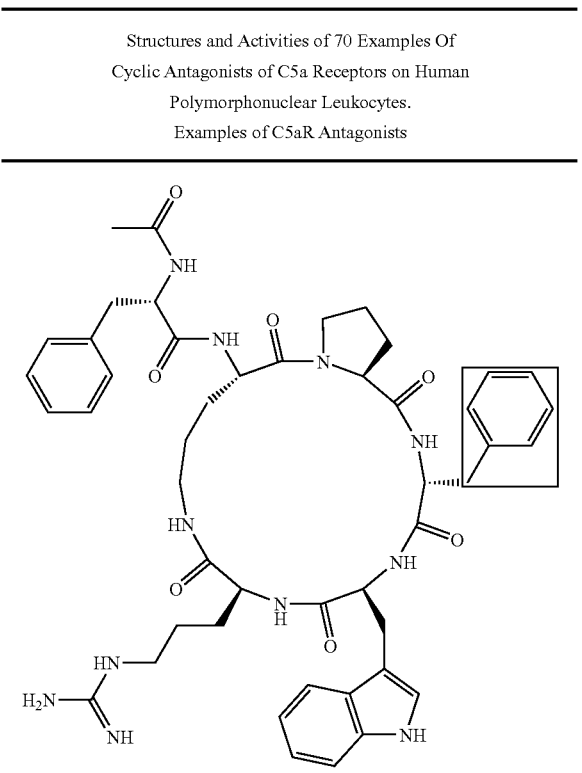
33
C5aR Binding IC50: 0.26 µM
C5aR Antagonist IC50: 22 nM
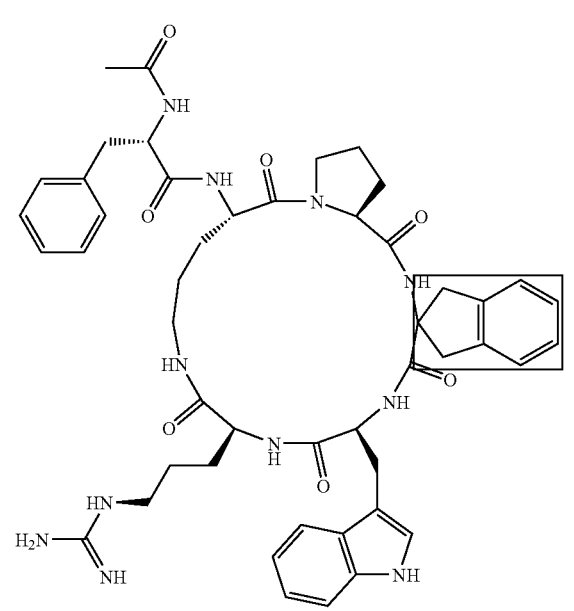
34
C5aR Binding IC50: 22.7 µM
C5aR Antagonist IC50: ND
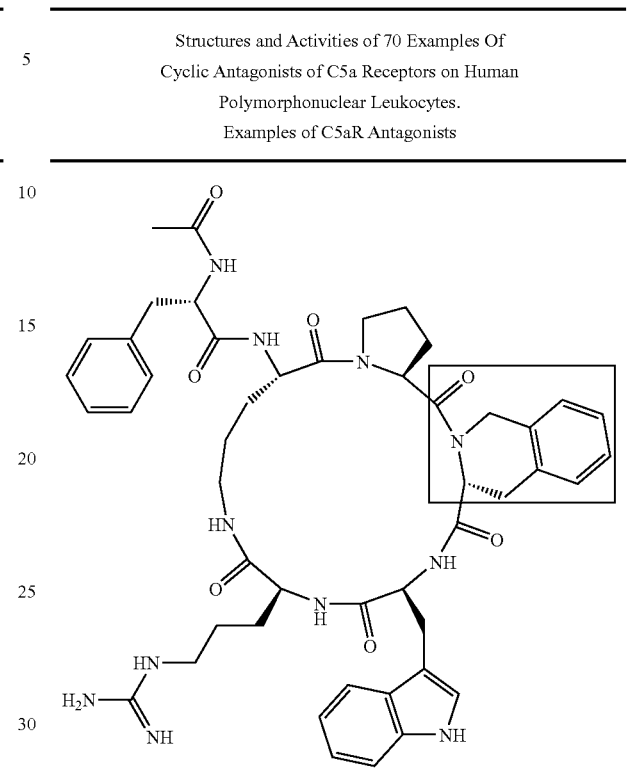
35
C5aR Binding IC50: 9.2 µM
C5aR Antagonist IC50: 15 nM
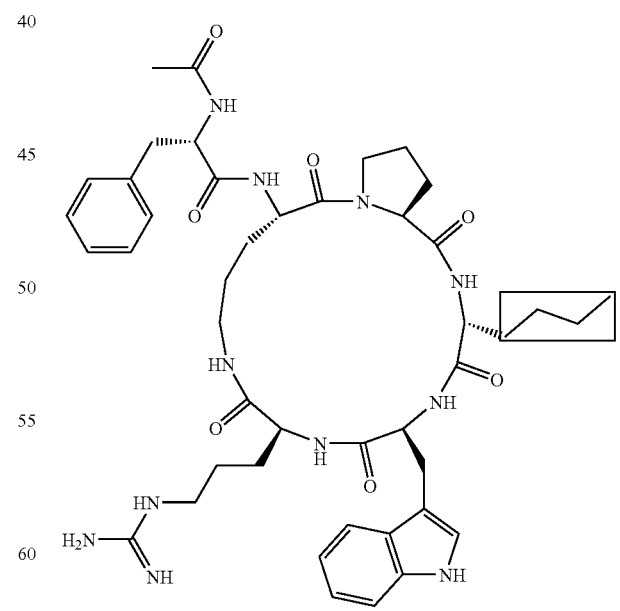
36
C5aR Binding IC50: 0.53 µM
C5aR Antagonist IC50: 30 nM TABLE 2-continued
Structures and Activities of 70 Examples Of
Cyclic Antagonists of C5a Receptors on Human
Polymorphonuclear Leukocytes.
Examples of C5aR Antagonists
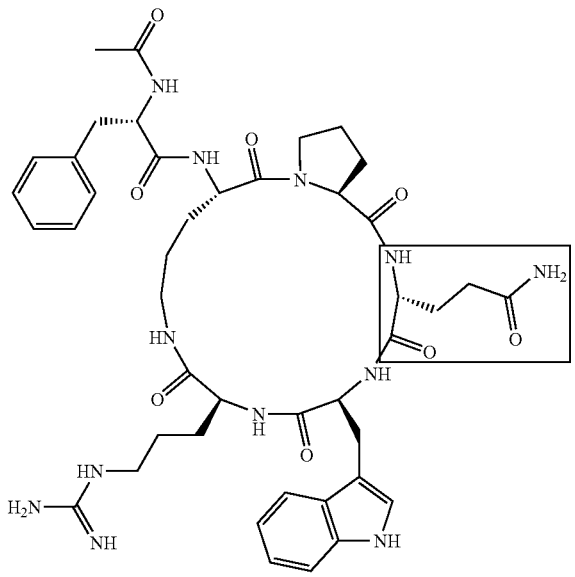
37
C5aR Binding IC50: 77 μM
C5aR Antagonist IC50: 71 nM
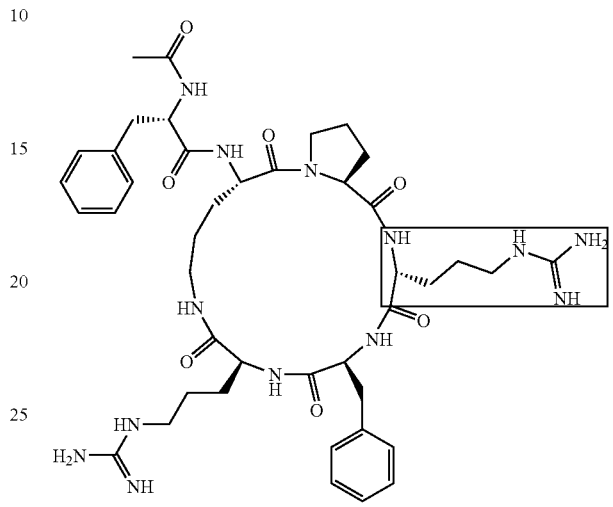
39
C5aR Binding IC50: >1000 μM
C5aR Antagonist IC50: ND
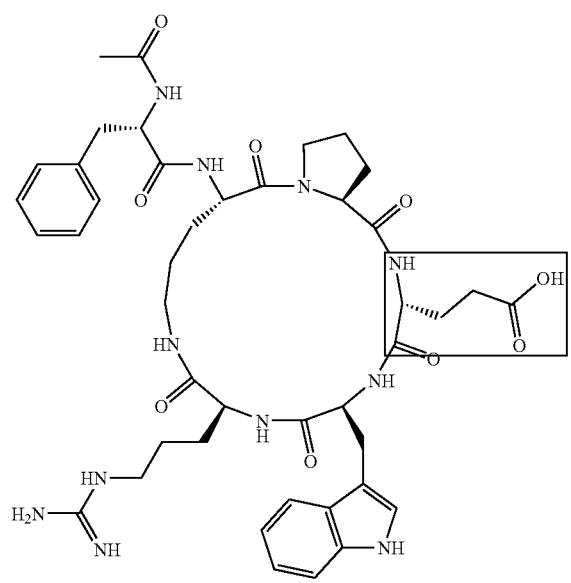
38
C5aR Binding IC50: 77 μM
C5aR Antagonist IC50: 71 nM
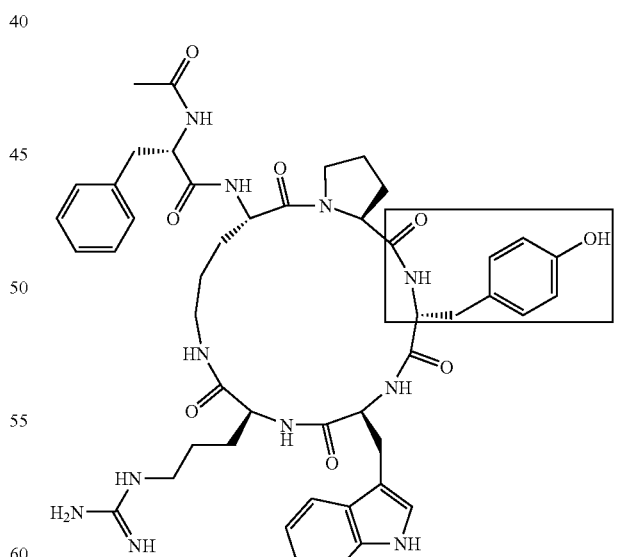
40
C5aR Binding IC50: 2.16 μM
C5aR Antagonist IC50: 300 nM TABLE 2-continued Structures and Activities of 70 Examples Of
Cyclic Antagonists of C5a Receptors on Human
Polymorphonuclear Leukocytes.
Examples of C5aR Antagonists

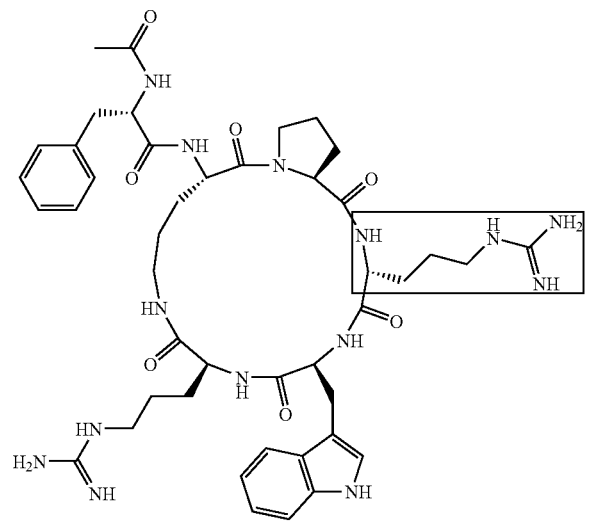

41
C5aR Binding IC50: >100 μM
C5aR Antagonist IC50: ND

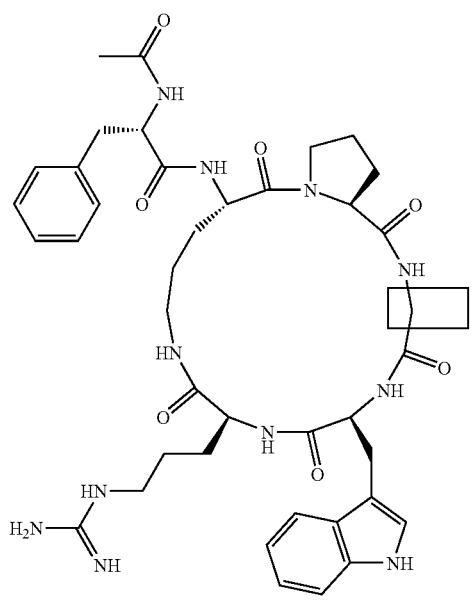

42
C5aR Binding IC50: 1082 μM
C5aR Antagonist IC50: ND

TABLE 2-continued

Structures and Activities of 70 Examples Of
Cyclic Antagonists of C5a Receptors on Human
Polymorphonuclear Leukocytes.
Examples of C5aR Antagonists

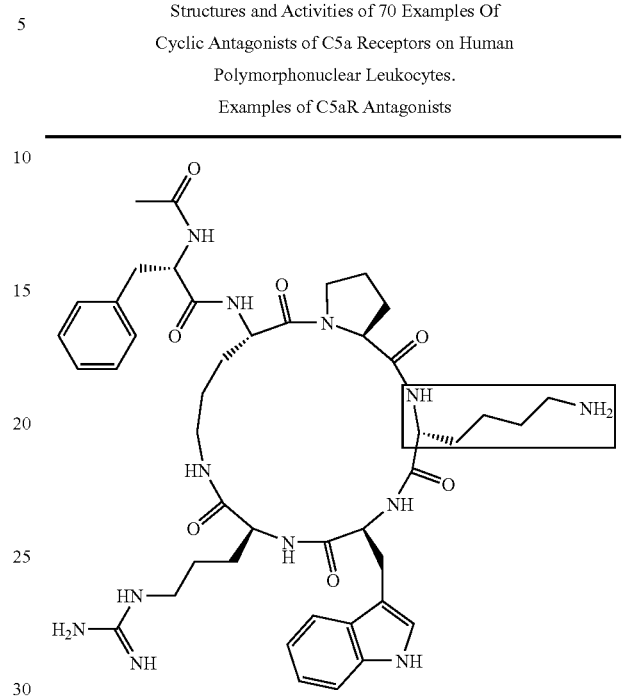

43
C5aR Binding IC50: 77 μM
C5aR Antagonist IC50: 77 nM

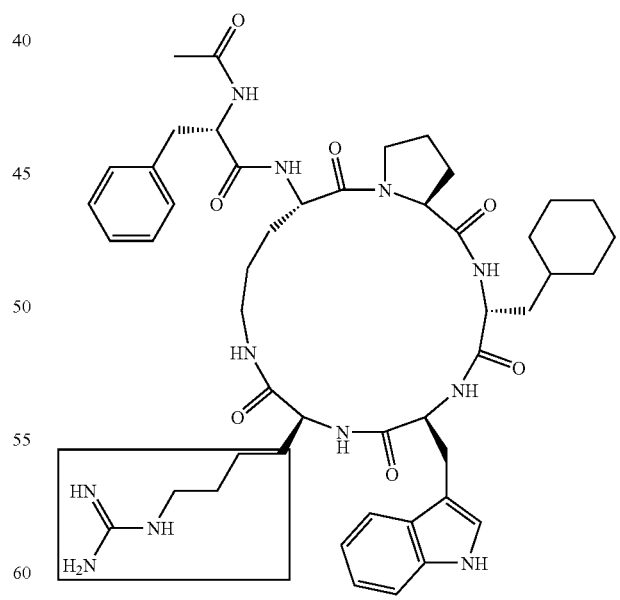

44
C5aR Binding IC50: 1.36 μM
C5aR Antagonist IC50: 160 nM

TABLE 2-continued

Structures and Activities of 70 Examples Of
Cyclic Antagonists of C5a Receptors on Human
Polymorphonuclear Leukocytes.
Examples of C5aR Antagonists

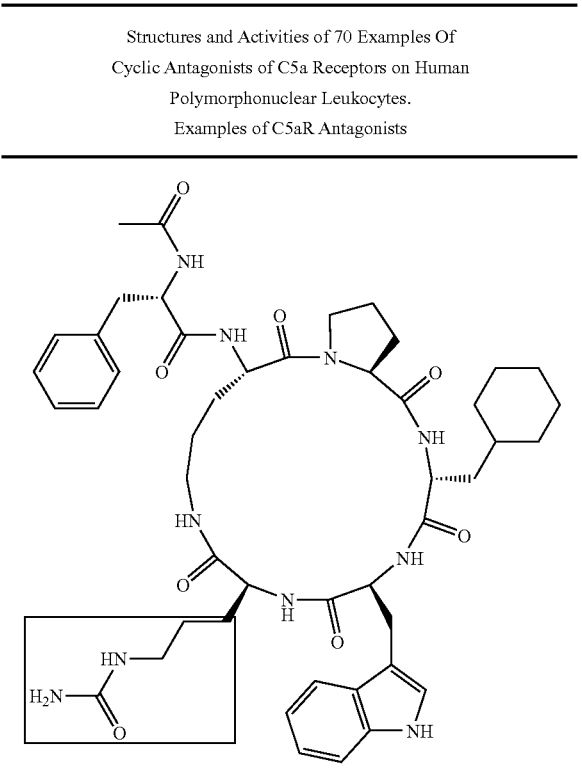

45
C5aR Binding IC50: 6.0 μM
C5aR Antagonist IC50: 69 nM

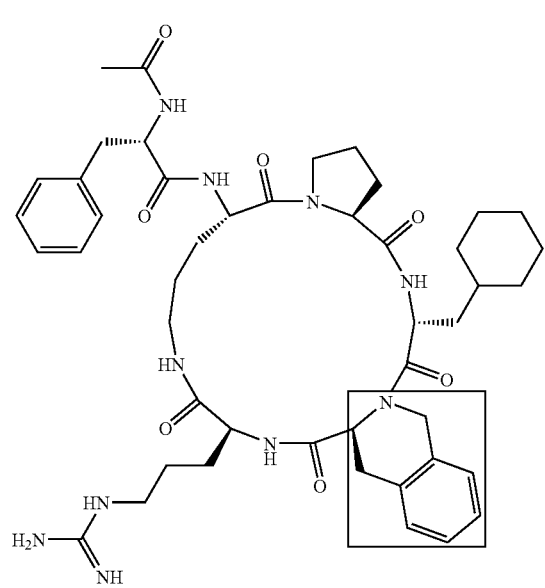

56
C5aR Binding IC50: 3.7 μM
C5aR Antagonist IC50: 10.9 nM

TABLE 2-continued

Structures and Activities of 70 Examples Of
Cyclic Antagonists of C5a Receptors on Human
Polymorphonuclear Leukocytes.
Examples of C5aR Antagonists

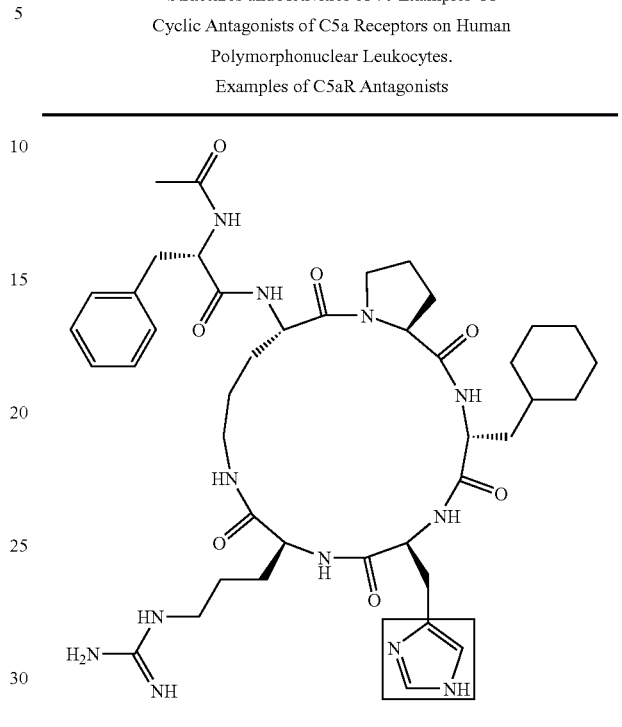

57
C5aR Binding IC50: 23.5 μM
C5aR Antagonist IC50: ND

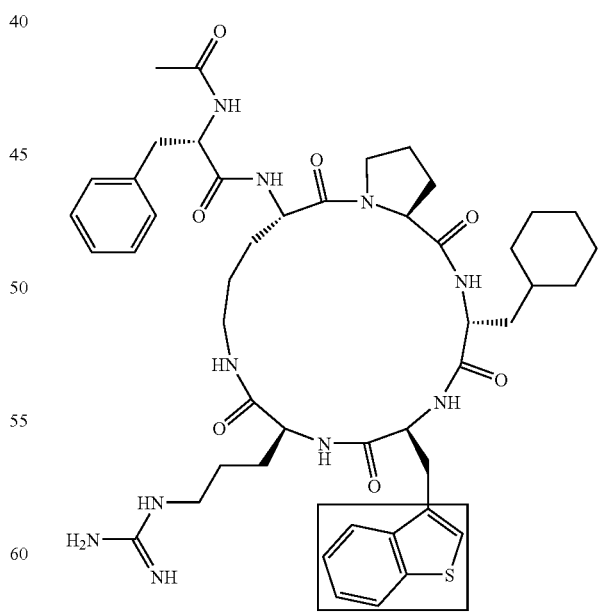

58
C5aR Binding IC50: 0.28 μM
C5aR Antagonist IC50: 172 nM

TABLE 2-continued
Structures and Activities of 70 Examples Of
Cyclic Antagonists of C5a Receptors on Human
Polymorphonuclear Leukocytes.
Examples of C5aR Antagonists
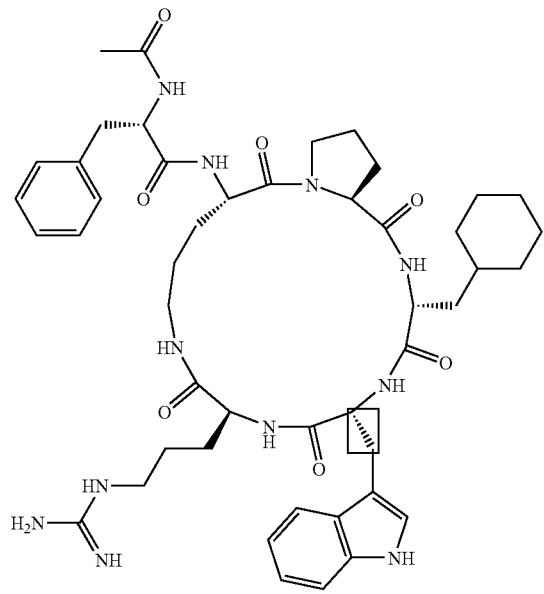
59
C5aR Binding IC50: 30.4 μM
C5aR Antagonist IC50: ND
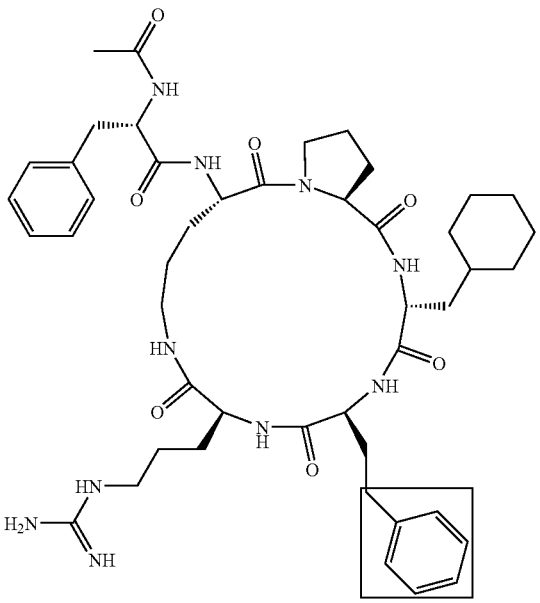
61
C5aR Binding IC50: 11.5 μM
C5aR Antagonist IC50: ND
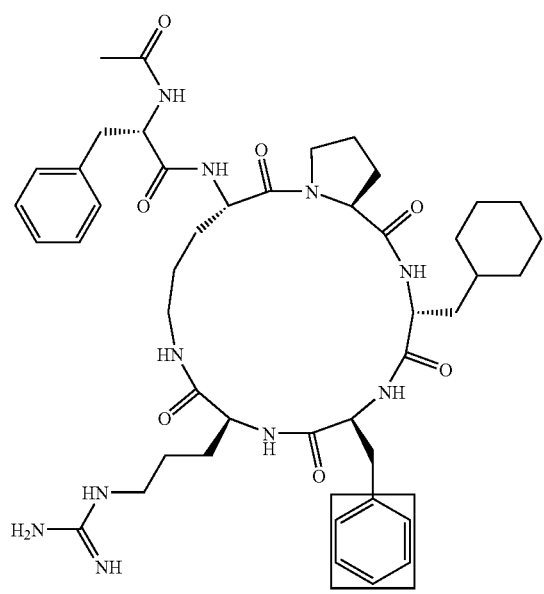
60
C5aR Binding IC50: 0.25 μM
C5aR Antagonist IC50: 32 nM
62
C5aR Binding IC50: 5.2 μM
C5aR Antagonist IC50: 4.6 μM

TABLE 2-continued

Structures and Activities of 70 Examples Of Cyclic Antagonists of C5a Receptors on Human Polymorphonuclear Leukocytes.
Examples of C5aR Antagonists

63
C5aR Binding IC50: 3.1 μM
C5aR Antagonist IC50: ND

64
C5aR Binding IC50: 27 μM
C5aR Antagonist IC50: 2 μM

"C5a Binding 1C50" refers to the concentration of compound required to achieve 50% maximum binding to human PMNs. "C5a Antagonist IC50" refers to the concentration of compound required to achieve 50% antagonism of myeloperoxidase release from C5a-stimulated human PMNs. Boxed regions indicate the location of relative changes between structures. Compound 1 is the lead compound from our previous application PCT/AU98/00490, and is included for purposes of comparison.

EXAMPLE 3

Cyclic Antagonists of C5a

Some examples of these cyclic antagonists and their apparent receptor-binding affinities and antagonist potencies are given in Table 3, in which the single letter code for amino acids is used. "d" indicates the dextro (D) form of an amino acid. "ND" indicates not determined.

TABLE 3

NEW COMPOUNDS AS C5a ANTAGONISTS

| AcPhe Replacements | Compound Number | n | Binding IC50 (μM) | Antagonist IC50 (nM) |
|---|---|---|---|---|
| MsF[OP-dCha-WR] | 10 | 3 | 0.47 | 34 |
| TsF[OP-dCha-WR] | 11 | 3 | 0.96 | 291 |
| AcPhg[Opd-Cha-WR] | 12 | 3 | 0.76 | 151 |
| AcG[OP-dCha-WR] | 13 | 3 | 37.2 | ND |
| Ac(o-fluoro)F[OP-dCha-WR] | 14 | 3 | 0.52 | 38 |
| Ac(m-fluoro)F[OP-dCha-WR] | 15 | 1 | 0.39 | ND |
| HC[OP-dCha-WR] | 17 | 3 | 0.22 | 31 |
| Hydrogen[OP-dCha-WR] | 19 | 3 | >1000 | ND |

Ms = Mesyl, Ts = Tosyl, MeSuc = Methylsuccinate, Suc = Succinate, Ahx = 6-Aminohexanoate, HPhe = Homophenylalanine, Phg = Phenylglycine, HC = Hydrocinnamate ND = not done

| Pro Replacements | Compound Number | n | Binding (μM) | Antagonist (nM) |
|---|---|---|---|---|
| AcF[O-Hyp-dCha-WR] | 25 | 3 | 0.27 | ND |
| AcF[O-Thp-dCha-WR] | 26 | 1 | 75.5 | ND |
| AcF[O-Phe-dCha-WR] | 22 | 3 | 2.43 | ND |

Hyp = trans-Hydroxyproline, Thp = cis-Thioproline

| D-Cha Replacements | Lab Code | n | Binding (μM) | Antagonist (nM) |
|---|---|---|---|---|
| AcF[OP-dCha-WR] | 3D53, 1 | 13 | 0.45 | 28 |
| AcF[OP-dLeu-WR] | 31 | 3 | 1.13 | 35 |
| AcF[OPGWR] | 42 | 3 | 1082 | ND |
| AcF[OP-dVal-WR] | 29 | 3 | 13.0 | ND |
| AcF[OP-dNle-WR] | 36 | 3 | 0.53 | 30 |
| AcF[OP-dTic-WR] | 35 | 3 | 9.18 | 15,000 |
| AcF[OP-aic-WR] | 34 | 3 | 22.71 | ND |
| AcF[OP-dTyr-WR] | 40 | 3 | 2.16 | 300 |
| AcF[OP-dArg-WR] | 41 | 3 | >100 | ND |
| AcF[OP-dPhe-WR] | 33 | 3 | 0.26 | 22 |
| AcF[OP-dhCha-WR] | 28 | 3 | 0.39 | 40.5 |

Aic—aminoindanecarboxylic acid
Tic—tetrahydroisoquinoline
dhCha—D-homocyclohexylalanine

| Trp Replacements | Lab Code | n | Binding (μM) | Antagonist (nM) |
|---|---|---|---|---|
| AcF[OP-dCha-HR] | 57 | 3 | 23.5 | ND |
| AcF[OP-dCha-FR] | 60 | 3 | 0.25 | 32 |
| AcF[OP-dCha-LR] | 51 | 3 | 18.9 | 3,000 |
| AcF[OP-dCha-Cha-R] | 50 | 3 | 11.9 | 4,500 |
| AcF[OP-dCha-hPhe-R] | 61 | 3 | 11.5 | ND |
| AcF[OP-dCha-2Nal-R] | 53 | 3 | 15.8 | ND |
| AcF[OP-dCha-Bta-R] | 58 | 3 | 0.28 | 172 |
| AcF[OP-dCha-Flu-R] | 54 | 3 | 28.9 | ND |
| AcF[OP-dCha-1Nal-R] | 52 | 3 | 0.71 | 46.6 |
| AcF[OPdCha-Tic-R] | 56 | 3 | 3.73 | 10,900 |
| AcF[OP-dCha-G-R] | 55 | 3 | >1000 | ND |
| AcF[OPdCha-dTrp-R] | 59 | 3 | 30.4 | ND | hPhe = Homophenylalanine, 2Nal = 2-Naphthylalanine,
1Nal = 1-Naphthylalanine, Bta = Benzothienylalanine,
Flu = Fluorenylalanine, Tyr-O-alkyl = O-alkylated analogue of tyrosine.
Tic = tetrahydroisoquinoline TABLE 3-continued NEW COMPOUNDS AS C5a ANTAGONISTS

| Arg Replacements | Lab Code | n | Binding (μM) | Antagonist (nM) |
|---|---|---|---|---|
| AcF[OPdChaW-Cit] | 45 | 3 | 6.00 | 690 |
| AcF[OpdChaW-K] | 47 | 3 | 24.15 | ND |
| AcF[OpdChaW-hArg] | 44 | 3 | 1.36 | ND |

Can = L-canavanine, Cit = Citrulline, hArg = homoarginine

| Multiple Replacements | Lab Code | n | Binding (μM) | Antagonist (nM) |
|---|---|---|---|---|
| AcF[OP-dPhe-dleu-Nal-R] | 105 | 3 | 3.1 | ND |
| AcF[OP-dPhe-FR] | 62 | 3 | 5.2 | 5,210 |
| AcF[DapOPdChaWRC] | 151 | 3 | 1.84 | 100 |
| AcF[OP-dPhe-1Nal-R] | 63 | 3 | 3.1 | ND |
| AcF[OP-dPhe-Y-R] | 150 | 3 | 69.2 | ND |

1Nal = 1-Naphthylalanine, Dap = 2'3-diaminoproprionic acid, dPhe = D-phenylalanine

EXAMPLE 4

Pharmacophore Refinement

On the basis of the results in Table 2, we can develop a refined pharmacophore for active antagonism of the C5a receptor on human polymorphonuclear leukocytes, as follows:

Position "A" can tolerate a very large number of groups, including H (e.g. compound 17,18), alkyl, aryl, $NH_2$, NEalkyl, $N(alkyl)_2$, NHaryl, NHacyl (e.g. compounds 1,3,4, 5,6,), NHbenzoyl (e.g. compound 2), OH, Oalkyl, Oaryl, $NHSO_2$alkyl (e.g. compound 10), $NHSO_2$aryl (e.g. compound 11), without an adverse effect on activity.

The wide tolerance to substitution at position "A" indicates that there is considerable space in the receptor for appendages to the cyclic peptide scaffold. This position can therefore be used for adding substituents in order to vary the water and lipid solubility of the antagonist, thereby enhancing oral or transdermal absorption of the antagonist. This position also allows attachment of labels such as fluorescent tags, agonists or polypeptide sequences which confer high affinity for target cells, such as sequences similar to amino acids 1-69 of C5a.

Position "B" can be alkyl, aryl, phenyl, benzyl, naphthyl or indole, or the side chain of a D- or L-amino acid such as L-phenylalanine (compound 1), or L-phenylglycine (compound 12). It should not be the side chain of D-phenylalanine (compound 8), L-homophenylalanine (compound 7), L-tyrosine (compound 9), L-homotyrosine, glycine (compound 13), L-tryptophan (compound 16), or L-homotryptophan.

Position "B" does not tolerate a wide range of substitutents. It appears that the benzyl group of L-phenylalanine cannot tolerate much substitution, and cannot be made much bulkier. This position seems to be required for receptor binding, rather than being important for antagonism per se, since the greatest effects on modification were on receptor affinity, as measured by IC50.

Position "C" should be a small substituent, such as the side chain of a D- or L-amino acid such as proline (compound 1), L-valine (compound 20), alanine, trans-hydroxyproline (compound 25), or cis-thioproline (compound 26). It should not be a bulky substituent such as the side chains of L-isoleucine (compound 21), D- or L-phenylalanine (compounds 22, 23), L-cyclohexylalanine (compound 24).

Position "D" should be a bulky substituent, such as the side chain of a D-amino acid like D-Leucine (compound 31), D-homoleucine, D-cyclohexylalanine (compound 1), D-homocyclohexylalanine (compound 28), D-valine (compound 29), D-norleucine (compound 36), D-homo-norleucine, D-phenylalanine (compound 33), D-tetrahydroisoquinoline (compound 35), D-glutamine (compound 37), D-glutamate (compound 38), or D-tyrosine (compound 40). It should not be a smaller substituent, such as the side chain of glycine, D-alanine (compound 30), a bulky planar side chain like D-tryptophan (compound 32), a bulky charged side chain like D-arginine (compound 39) or D-Lysine (compound 43), or an L-amino acid like L-cyclohexylalanine (compound 27). Small D-amino acids and small or large L-amino acids at position "D" on the scaffold lead to greatly reduced affinity for the C5a receptor.

Position "E" is chosen from among the bulky side chains of L-Tryptophan (compound 1) and L-homotryptophan, but not D-tryptophan (compound 59) or L-N-methyltryptophan (compound 47); L-phenylalanine (compound 60) but not L-homophenylalanine (compound 61); L-naphthyl (compound 52) but not L-2-naphthyl (compound 53); L-3-benzothienylalanine (compound 58). It should not be the side chain of L-cyclohexylalanine (compound 50), D-leucine (compound 51), L-fluorenylalanine (compound 54), glycine (compound 55), L-tetrahydroisoquinoline (compound 56), or L-histidine (compound 57).

Substituents at position "E" on the cyclic peptide scaffold are crucial for antagonism of the C5a receptor. Substituents at this position may limit the conformational changes usually associated with agonist responses. This may be a "blocking" residue, which fixes the antagonist in the receptor and prevents the conformational reorganization in the receptor which is necessary for agonism.

Position "F" may be the side chain of L-arginine (compound 1), L-homoarginine (compound 44), L-citrulline (compound 45); or L-canavinine (compound 48). It should not be D- or L-lysine (compound 47), D- or L-homolysine, or glycine (compound 49). The size of the substitutent at this position is important for conferring high receptor affinity. The citrulline compound has no charged side chain, yet still possesses appreciable antagonist potency compared to arginine at this position.

Position "X" may be —$(CH2)_n$NH— or —$(CH2)_n$—S—, where n is an integer from 1 to 4, preferably 2 or 3, —$(CH_2)_2$O—, —$(CH_2)_3$O—, —$(CH_2)_3$—, —$(CH_2)_4$—, —$CH_2$COCHRNH—, or —$CH_2$—NHCOCHRNH— where R is the side chain of any common or uncommon L- or D-amino acid. This group provides the cyclisation link, for example between the Arg and Phe residues of compound 1, and thus influences the structure of the cyclic backbone. In addition, substituents such as R on this linker could potentially interact with receptor residues to increase affinity of the antagonists.

N-methylation of the amino acid components of the cycles tends to reduce the receptor binding affinity and antagonist potency of the compounds (e.g. 64, 65), although N-methylation of the delta nitrogen of ornithine has virtually no effect on antagonist potency.

Multiple changes on the scaffold can be detrimental to obtaining increased antagonist potency relative to 1. Thus although L-Phe was a suitable replacement (e.g. 60) for L-Trp in 1, with little change in antagonist potency, a combination of changes to 1, such as L-Phe for Trp and either L-HomoPhe for Arg (e.g. 67) or p-chloro-phenylalanine for Arg (e.g. 68), led to reduced affinity for the receptor and reduced antagonist potency. Similarly when L-Trp in 1 was replaced by L-Phe and D-Cha was also replaced by D-Phe, the compound lost substantial potency (e.g. 62) While a change from D-Cha in 1 to D-Phe led to retention of the antagonist potency (e.g. 33), this change is detrimental when coupled with replacement of L-Trp by L-Phe (62).

Clearly there is cooperativity in the binding of these residues to the receptor, since either of the single changes (e.g. 33, 60) results in substantially higher potency than when the changes are made together (e.g. 62). When the Arg was replaced by an aromatic group still containing a charged amine (69), there was a significant loss in activity, as was observed when Phe of 60 was replaced by a substituted tyrosine (70).

All these changes are indicative of what can and cannot be tolerated On the cyclic scaffold used to engender affinity for the human PMN C5a receptor and antagonist potency. It is recognised that C5a receptors on other types of cells may have different tolerances for side chains, but the cyclic scaffold will still form the basis of active compounds.

EXAMPLE 5

Reverse Passive Arthus Reaction in the Rat

A reverse passive peritoneal Arthus reaction was induced as previously described (Strachan et al., 2000), and a group of rats were pretreated prior to peritoneal deposition of antibody with AcF-[OPdChaWR] (1) by oral gavage (10 mg kg$^{-1}$ dissolved in 10% ethanol/90% saline solution to a final volume of 200 μl) or an appropriate oral vehicle control 30 min prior to deposition of antibody. Female Wistar rats (150-250 g) were anaesthetised with ketamine (80 mg kg$^{-1}$ i.p.) and xylazine (12 mg kg$^{-1}$ i.p.).

Figure 1:
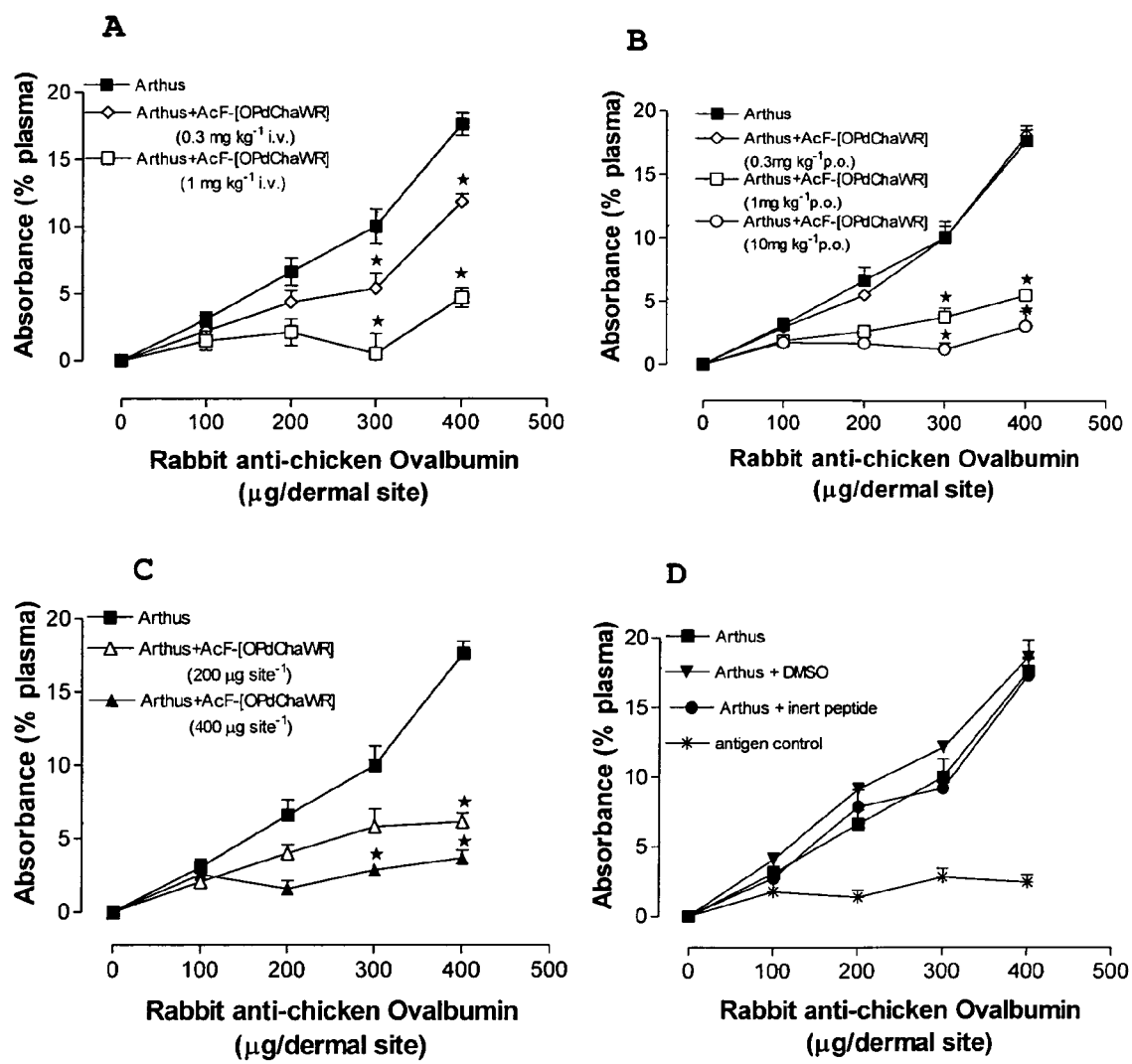
FIG. 1 shows the inhibition of the vascular leakage associated with a dermal Arthus reaction by intravenous (A), oral (B) and topical (C) AcF-[OPdChaWR], and appropriate controls (D).

The lateral surfaces of the rat were carefully shaved and 5 distinct sites on each lateral surface clearly delineated. A reverse passive Arthus reaction was induced in each dermal site by injecting Evans blue (15 mg kg$^{-1}$ i.v.), chicken ovalbumin (20 mg kg$^{-1}$ i.v.) into the femoral vein 10 min prior to the injection of antibody. Rabbit anti-chicken ovalbumin (saline only, 100, 200, 300 or 400 kg antibody in a final injection volume of 30 μL) was injected in duplicate at two separate dermal sites on each lateral surface of the rat, giving a total of 10 injection sites per rat. Rats were placed on a heating pad, and anaesthetic was maintained over a 4 h-treatment period with periodic collection of blood samples. Blood was allowed to spontaneously clot on ice, and serum samples were collected and stored at –20° C. Four hours after induction of the dermal Arthus reaction, the anaesthetised rat was euthanased and a 10 mm$^2$ area of skin was collected from the site of each Arthus reaction. Skin samples were stored in 10% buffered formalin for at least 10 days before histological analysis using haematoxylin and eosin stain. Additionally, a second set of skin samples were placed in 1 mL of formamide overnight, and the absorbance of Evans blue extraction measured at 650 nm, as an indicator of serum leakage into the dermis. FIG. 1 shows the optical density of dermal punch extracts following intradermal injection of rabbit anti-chicken ovalbumin at 0-400 μg site$^{-1}$ following pretreatment with AcF-[OPdChaWR] intravenously, orally or topically. Data are shown as absorbance at 650 nm as a percentage of the plasma absorbance, as mean values±SEM (n=3-6). *indicates a P value≦0.05 when compared to Arthus control values.

Rats were pretreated with the C5aR antagonist, AcF-[OPdChaWR] (1) as the TFA salt, either intravenously (0.3-1 mg kg$^{-1}$ in 200 μL saline containing 10% ethanol, 10 min prior to initiation of dermal Arthus), orally (0.3-10 mg kg$^{-1}$ in 200 μL saline containing 10% ethanol by oral gavage, 30 min prior to initiation of dermal Arthus in rats denied food access for the preceding 18 hours) or topically (200-400 μg site$^{-1}$ 10 min prior to initiation of dermal Arthus reaction), or with the appropriate vehicle control. Topical application of the antagonist involved application of 20 μl of a 10-20 mg mL-1 solution in 10% dimethyl sulphoxide (DMSO), which was then smeared directly onto the skin at each site, 10 min prior to induction of the Arthus reaction.

The saline-only injection site from rats treated with Evans blue only served as antigen controls, the saline-only injection site from rats treated with Evans blue plus topical DMSO only served as a vehicle control, the saline-only injection site from rats treated with Evans blue plus either intravenous, oral or topical antagonist only served as antagonist controls, and Evans blue plus dermal rabbit anti-chicken ovalbumin served as antibody controls. Topical application of the peptide AcF-[OPGWR] which has similar chemical composition and solubility to that of AcF-[OPdChaWR] (1), but with an IC$_{50}$ binding affinity of >1 mM in isolated human PMNs, served as an inactive peptide control. AcF-[OPGWR] was also dissolved in 10% DMSO and applied topically at 400 μg site$^{-1}$ 10 min prior to initiation of the Arthus reaction.

TNFα Measurement

Figure 2:
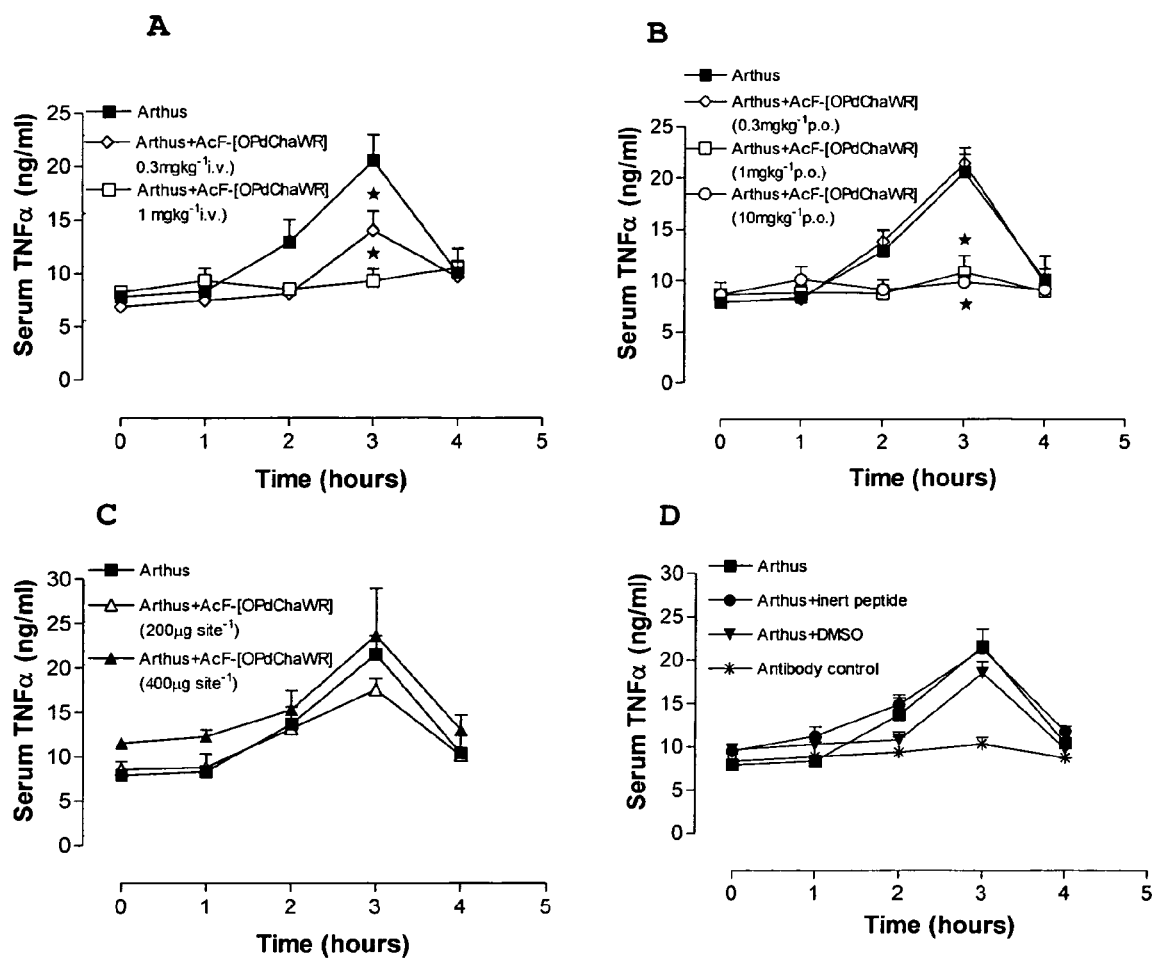
FIG. 2 shows the inhibition of the rise in circulating TNFα associated with a dermal Arthus reaction by intravenous (A), oral (B) and topical (C) AcF-[OPdChaWR], and appropriate topical controls (D).

Serum TNFα concentrations were measured using an enzyme-linked immunosorbent assay (ELISA) kit. Antibody pairs used were a rabbit anti-rat TNFα antibody coupled with a biotinylated murine anti-rat TNFα antibody. FIG. 2 shows the serum TNFα concentrations at regular intervals after initiation of a dermal Arthus reaction, with group of rats pretreated with AcF-[OPdChaWR] intravenously, orally or topically. Data are shown as mean values±SEM (n=3-6). *indicates a P value of≦0.05 when compared to Arthus control values.

Interleukin-6 Measurement

An ELISA method as described previously was used to measure serum and peritoneal lavage fluid interleukin-6 (IL-6) concentrations (Strachan et al., 2000).

Pathology Assessment

Figure 3:
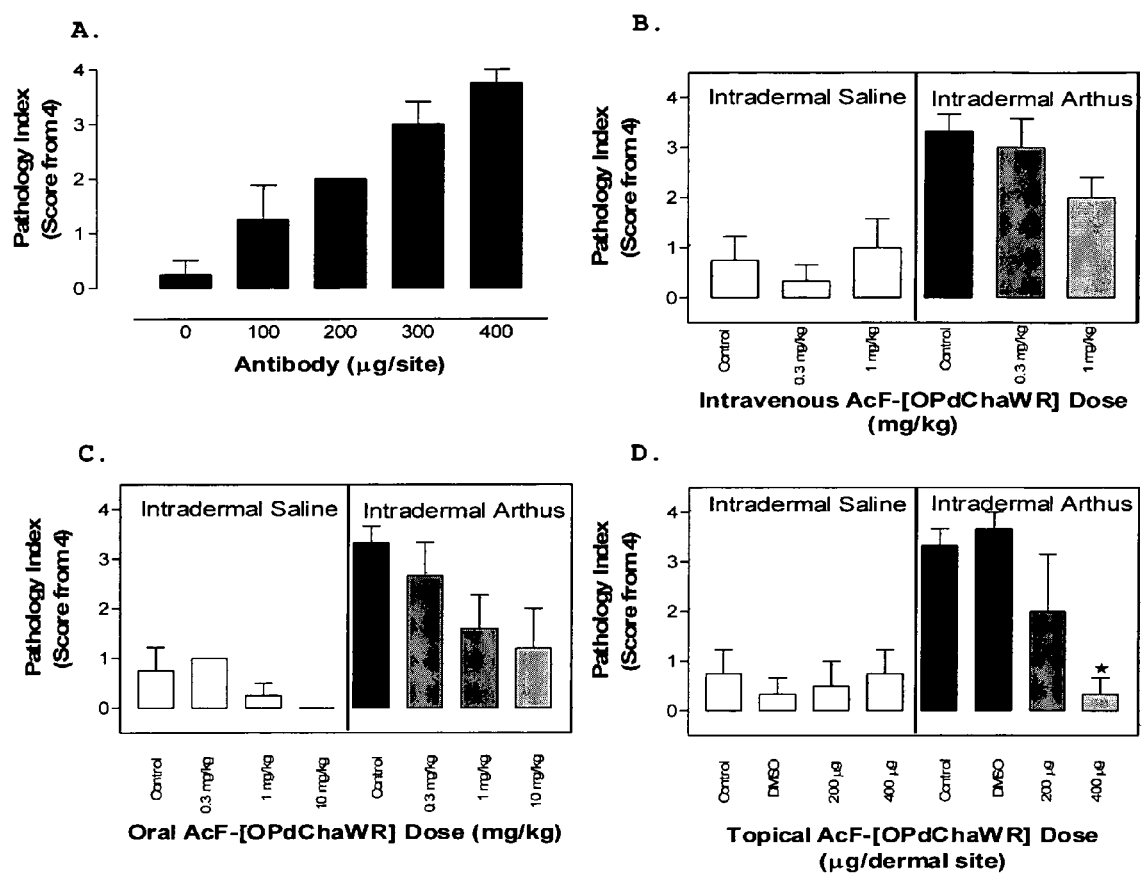
FIG. 3 shows the reduction of the pathology index associated with a dermal Arthus reaction by intravenous, oral and topical AcF-[OPdChaWR].

Rat skin samples were fixed in 10% buffered formalin for at least 10 days, and stained with haematoxylin and eosin using standard histological techniques. Dermal samples were analysed in a blind fashion for evidence of pathology, and the degree of rat PMN infiltration was scored on a scale of 0-4. Initiation of a dermal Arthus reaction resulted in an increase in interstitial neutrophils, which was quantified in the following manner. Sections were given a score of 0 if no abnormalities were detected. A score of 1 indicated the appearance of increased PMNs in blood vessels, but no migration of inflammatory cells out of the lumen. A score of 2 and 3 indicated the appearance of increasing numbers of PMNs in the interstitial tissue and more prominent accumulations of inflammatory cells around blood vessels. A maximal score of 4 indicated severe pathological abnormalities were present in dermal sections, with excessive infiltration of PMNs into the tissues and migration of these cells away from blood vessels. FIG. 3 shows the intradermal injection of increasing amounts of antibody leads to a dose-responsive increase in the pathology index scored by dermal samples (A). Data are shown for dermal samples intradermally injected with saline or 400 μg site$^{-1}$ antibody (n=5) in rats pretreated with AcF-[OPdChaWR] intravenously (B) (n=3), orally (C) (n=3) and topically (D) (n=3). Data are shown as mean values±SEM. * P≦0.05 when compared to Arthus values using a non-parametric t-test.

EXAMPLE 6

Effect of C5a Antagonist on Model of Intestinal Ischemia-Reperfusion Injury in Rats Female Wistar rats (250-300 g, n=132) were fasted and given only water for 12 h prior to all experiments. Animals were anaesthetised by the intraperitoneal injection of 80 mg kg$^{-1}$ ketamine and 10 mg kg$^{-1}$ xylazine and throughout the procedure rats were placed on a heating pad to maintain normal body temperature. The abdomen was opened through a midline incision to expose the superior mesenteric artery (SMA). A non-traumatic occlusive device for the artery was fashioned from a silk suture looped though a length of polyethylene tubing. The SMA was occluded by applying traction to the ends of the loop. A polyethylene catheter was inserted in the femoral vein to allow the infusion of either 1 mg kg-1 AcF-[OPdChaWR] (1) in 5% ethanol or sterile, pyrogen-free saline in 0-2 ml volume. Infusions were made over a 2 min period. Oral dosing of AcF-[OPdChaWR] (1) (0.3, 1, 10 mg kg$^{-1}$) was achieved by gavage (0.2 ml saline in 25% ethanol) 60 min prior to SMA occlusion. Intestinal ischemia was induced by clamping the SMA for 30 min, after which the occlusive suture was removed, then reperfusion was monitored for another 120 min. Sham-operated rats were treated in an identical fashion, with the omission of vascular occlusion, and were infused with 0.2 ml of sterile, pyrogen-free saline or gavaged with 0.2 ml of saline in 25% ethanol. Blood samples (50 μL) were collected into heparinised Eppendorf tubes at regular intervals over the 180 min duration of the experiments for the estimation of PMN numbers. In a different series of identical experiments, whole blood was collected at regular intervals over the 180 min and allowed to clot on ice, and serum or plasma samples collected and stored at −20° C. for later measurement of tumour necrosis factor-α (TNF-α), haptoglobin (Hp) and aspartate aminotransferase (AST) concentrations. At the end of the 120 min reperfusion period, the animals were euthanased with an overdose of pentobarbital A section of the occluded ileum was removed, the lumen rinsed with saline, and the intestine was blotted dry, then weighed. Specimens were dried in an oven for 24 hours at 80° C. to obtain the tissue dry weight. Intestinal oedema was determined by assessing the wet and dry tissue weight ratio. Additionally, segments of both ischaemic and normal intestine were harvested and rinsed with saline and immediately fixed in 10% buffered formaldehyde-saline for histological studies.

Figure 4:
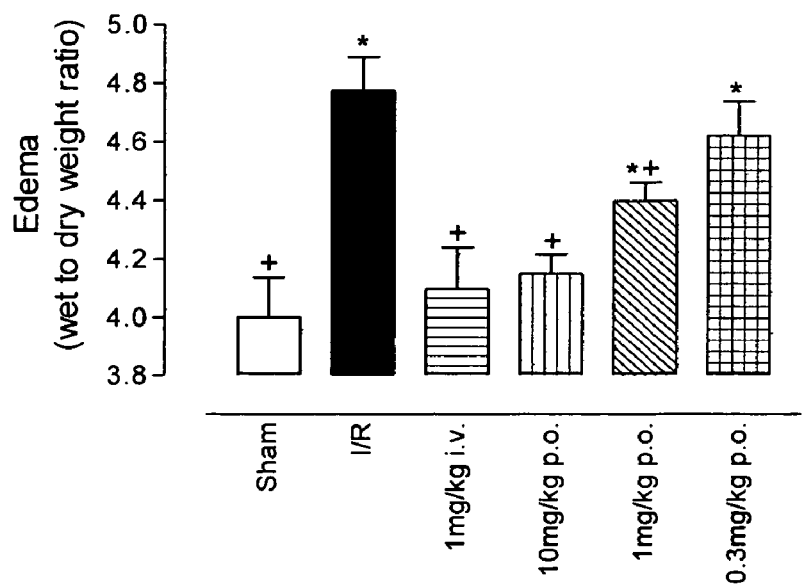
FIG. 4 shows the effect of a C5a antagonist on gut ischemia-reperfusion induced intestinal edema.

FIG. 4 shows that the wet-to-dry weight ratio of the small intestine is significantly elevated after ischemia-reperfusion compared to sham-operated animals. Treatment with the C5a receptor antagonist AcF-[OPdChaWR] 1 mg/kg i.v. and 10 mg/kg p.o. significantly reduced tissue edema compared to untreated ischemia-reperfusion (I/R) animals. Data are shown as means±SEM (n=4-6 in each group). *, P<0.05 vs. sham-operated animals. +, P<0.05 vs. I/R animals.

Neutropenia Assay

Blood (50 μL) for PMN counts was placed into heparinised tubes and then layered over an equal volume of Histopaque 1083 (Sigma, U.S.A.), PMNs were isolated and cell number counted on a haemocytometer. Concentrations of PMN's values are presented as mean percentage±SEM of the values obtained immediately prior to SMA occlusion.

Figure 5:
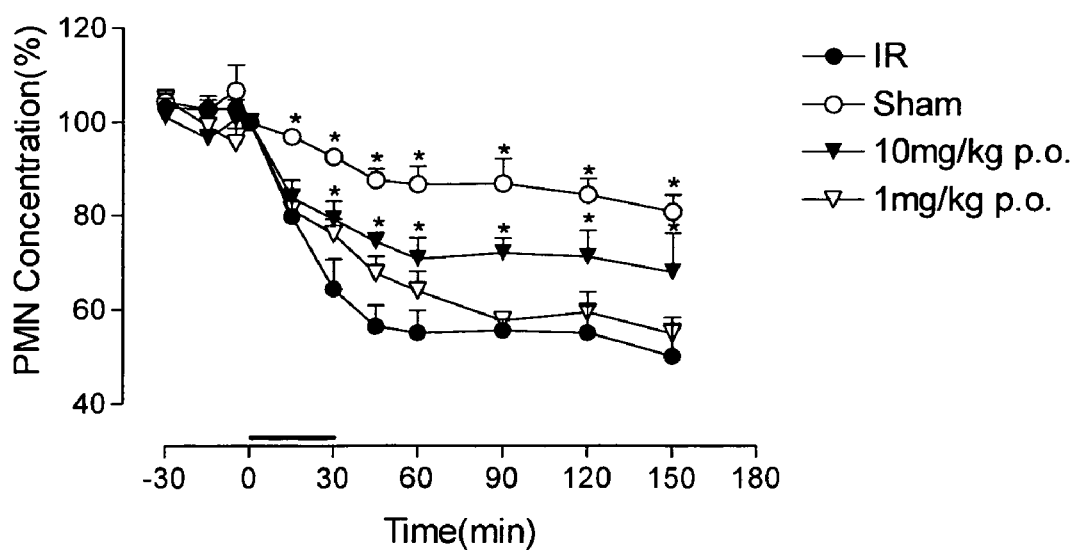
FIG. 5 shows the effect of a C5a antagonist on gut ischemia-reperfusion induced neutropenia.

FIG. 5 shows that the gut ischemia-reperfusion caused significant reduction in circulating PMN concentrations compared with sham-operated animals (A, B). Pretreatment of rats with C5a receptor antagonist AcF-[OPdChaWR] 1 mg/kg i.v. (A) and 10 mg/kg p.o. (B) significantly inhibited ischemia-reperfusion induced neutropenia. 1 mg/kg p.o. (B) treated animals showed no inhibition of neutropenia. Data are shown as means±SEM (n=6 in each group). *equals P<0.05 vs. Control animals. Bar shows 30 min period of ischemia.

Tumor Necrosis Factor-α Measurement

Serum TNF-α concentrations were measured using an enzyme-linked immunosorbent assay, (OptEIA, Pharmingen, USA), according to the manufacturers instructions. Concentrations of TNF-α in serum samples were determined by linear regression analysis from the standard curve.

FIG. 6 shows that the gut ischemia-reperfusion resulted in significant elevation in serum TNF-α compared with sham operated animals. Pre-treatment of rats with the C5a receptor antagonist AcF-[OPdChaWR] 1 mg/kg i.v. and 1-10 mg/kg p.o. completely inhibited the change in serum. TNF-α levels. Data are shown as means±SEW (n=6 in each group). *, P<0.05 vs. sham-operated animals. The bar shows 30 min period of ischemia.

Haptoglobin Assay

Serum Hp was measured by using an Hp assay kit (Tridelta Development Ltd. U.K), according to the manufacturers' instructions. Concentrations of Hp in the serum samples were determined by linear regression analysis from the standard curve.

FIG. 7 shows that gut ischemia-reperfusion resulted in a significant increase in serum haptoglobin compared to sham-operated animals. Pretreatment of rats with C5a receptor antagonist AcF-[OPdChaWR] 1 mg/kg i.v. and 1,10 mg/kg p.o. significantly inhibited the increase in serum haptoglobin levels. Data are shown as means±SEM (n=4-6 in each group). *, P<0.05 vs. sham-operated animals. +, P<0.05 vs. I/R animals.

Aspartate Aminotransferase Assay

Plasma AST (AST/GOT; Sigma, USA) concentrations were measured according to manufacturers instructions within 48 h of collecting plasma. Plasma AST concentrations were derived from calibration curve. Results are expressed in Sigma-Franke (SF) units/ml.

Figure 8:
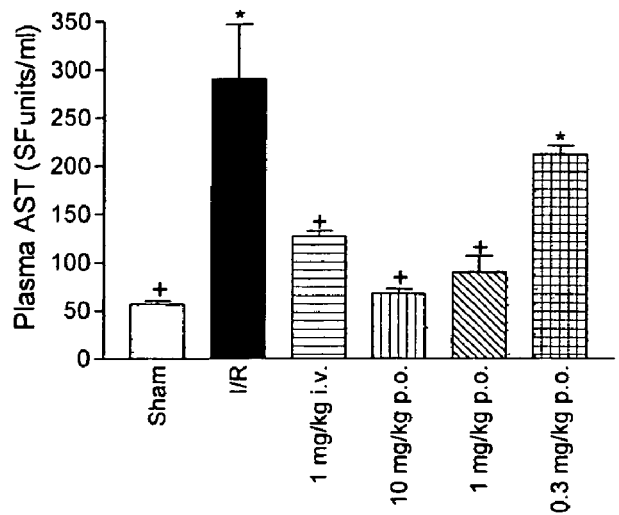
FIG. 8 shows the effect of a Ca antagonist on gut ischemia-reperfusion induced aspartate aminotransferase.

FIG. 8 shows that the gut ischemia-reperfusion resulted in a significant increase in plasma aspartate aminotransferase compared to sham-operated animals. Treatment with the C5a receptor antagonist AcF-[OPdChaWR] 1 mg/kg i.v. and 1,10 mg/kg significantly reduced gut ischemia-reperfusion induced aspartate aminotransferase compared to untreated I/R animals. Data are shown as means±SEM (n=6 in each group). *, P<0.05 vs. sham-operated animals. +, P<0.05 vs. I/R animals.

Histopathology

Specimens were fixed in 10% formaldehyde-saline, embedded in paraffin wax, sectioned serially, and stained with haematoxylin and eosin. Tissues were read and scored by a trained observer in a blinded fashion. The degree of intestinal tissue injury was determined using a previously described graded scale ranging from 0-8 (Chiu et al., 1970).

Figure 9:
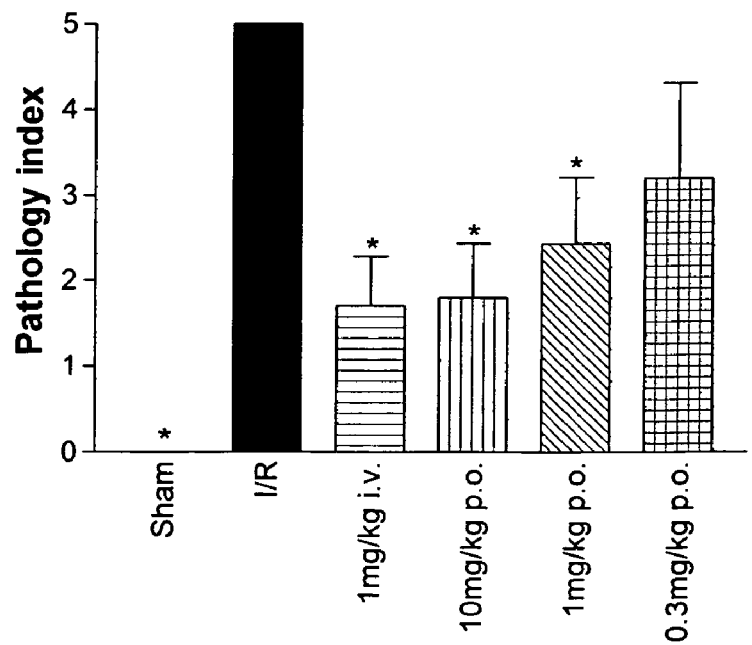
FIG. 9 shows the effect of a C5a antagonist on histopathology of gut ischemia-reperfusion.

FIG. 9 shows that gut ischemia-reperfusion resulted in significant damage to the intestine compared to sham-operated animals. Treatment with C5a receptor antagonist AcF-[OPdChaWR] 1 mg/kg i.v. and 1,10 mg/kg significantly reduced gut ischemia-reperfusion induced tissue damage compared to untreated I/R animals. Data are shown as mean±SEM (n=6 in each group). *, P<0.05 vs. I/R animals.

EXAMPLE 7

Rat Monoarticular Antigen-Induced Arthritis

Female Wistar rats (150-250 g) were obtained from the Central Animal Breeding House, University of Queensland. Methylated bovine serum albumin (mBSA) (0.5 mg) was dissolved in Freund's complete adjuvant (0.5 mg) and sonicated to produce a homogenous suspension. Each rat received a subcutaneous injection of this suspension (0.5 mL) on days 1 and 7. On day 12-28, rats were separated into separate cages, and body weight and food and water intake monitored daily. Rats received either ordinary tap water or drinking water containing AcF-[OPdChaWR] (1). Body weight and water intake were monitored daily, and rats received a daily dose of 1 mg/kg/day of the C5aR antagonist AcF-[OPdChaWR] (1) for days 12-28 of the trial. On day 14, rats were anaesthetised and their hind limbs shaved Each rat received an intra-articular (100 µl) injection of mBSA (0.5 mg) in the left knee, and saline in the right knee. The saline-only knee from rats receiving normal drinking water served as a saline control, the saline only knee from rats receiving AcF-[OPdChaWR] (1) in the drinking water served as an antagonist control.

Rats were euthanased on day 28, and whole blood collected into an Eppendorf tube and allowed to clot on ice. Blood samples were centrifuges (11,000 rpm×3 min) and serum collected and stored at −20° C. until analysis of serum cytokines using an ELISA. Each knee capsule was lavaged with 100 µL saline, and the total cell count determined using a haemocytometer. In addition, an aliquot of the knee joint lavage fluid was dropped onto a glass slide, and allowed to air dry. Once dry, cells were stained with a differential stain (Diff Quick) and a differential cell count was performed using a 40× dry lens microscope. The remaining lavage fluids from each joint were stored at −20° C. until later analysis of intra-articular cytokine levels using an ELISA. Each knee joint was removed and the skin was split with a scalpel blade to allow fixation. Knee samples were stored in 10% buffered formalin for $\geq$10 d. Knees were then rinsed with distilled water and placed in a saturated solution of EDTA solution for 21 d for decalcification before being embedded in paraffin wax.

Knee tissue samples were prepared using standard histological techniques as described above in Example 6 and stained using an heamotoxylin and eosin stain. Histological slides were analysed in a blinded fashion. Tissue sections were scored from 0-4, with a score of 0 indicating no abnormalities, and increasing scores with the appearance of synovial cell proliferation, inflammatory cell infiltration, cartilage destruction and haemorrhage. In no samples was there evidence of significant bone erosion. Samples of serum and synovial fluid were thawed on the day of ELISA analysis for TNFα and IL-6 levels. Concentrations were determined from a standard curve, using an ELISA as described previously in Example 6.

Figure 10:
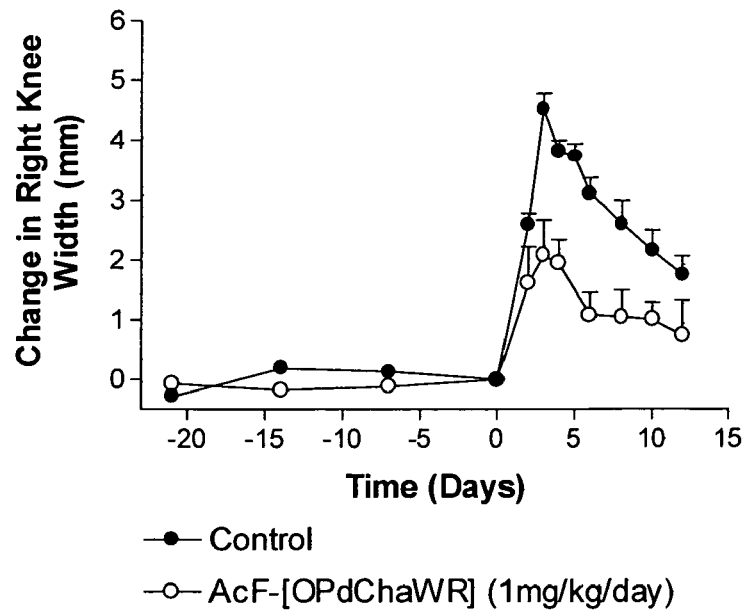
FIG. 10 shows the inhibition of arthritic right knee joint swelling by AcF-[OPdChaWR] given orally on Days 2 to +14.
Figure 11:
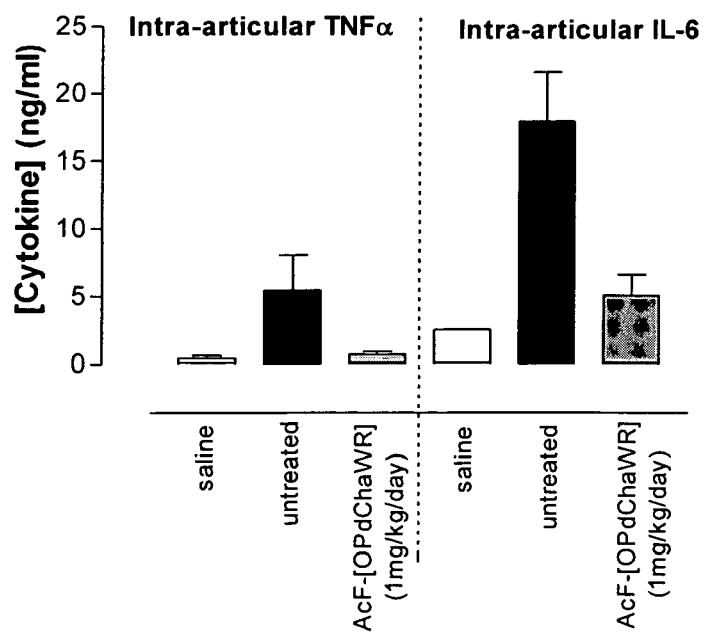
FIG. 11 shows the inhibition of right knee joint TNF-α and IL-6 levels in joint lavage. "Untreated" refers to animals not treated with AcF-[OPdChaWR] but with the right knee challenged with antigen following sensitisation.

FIG. 10 shows the inhibition of arthritic right knee joint swelling by AcF-[OPdChaWR] given orally on Days −2 to +14, while FIG. 11 shows the inhibition of right knee joint TNF-α and IL-6 levels in joint lavage. Untreated refers to animal not treated with AcF-[OPdChaWR] but with right knee challenged with antigen following sensitisation.

EXAMPLE 8

Topical Dermal Administration of C5a Antagonists

The invention teaches that topical administration of C5a antagonists may be used for the treatment of topical inflammatory disorders involving activation of the complement system. In this example we demonstrate that topical application of C5a antagonists can also result in systemic pharmacological actions and the appearance of pharmacologically relevant concentrations of C5a antagonists in the circulation.

The in vivo pharmacological properties of cyclic antagonists were examined following topical dermal administration. A model of endotoxaemia was used, in which 1 mg/kg *Escherichia coli* liposaccharide (LPS; serotype 55:B5, Sigma, USA, stored at 100 mg ml$^{-1}$ in dH$_2$O, 4° C.), was injected i.v into a rat, resulting in acute changes in circulating PMN levels and blood pressure. These parameters were measured in the presence and absence of C5aR antagonists (1 mg/kg i.v or 50 mg/kg/rat topically). This study shows that topical administration of C5a receptor antagonists is an effective method of delivery of these compounds, with systemic pharmacological activity being observed.

Female Wistar rats weighing between 200-250 g were used for in vivo testing of all C5a receptor antagonists. Rats were anaesthetized using the procedure described above, and transferred on to a heating pad to ensure that body temperature was maintained throughout the experiment. A catheter was inserted in the femoral vein, secured with a suture and flushed with 100 µL of heparinised saline. Rats were dosed with either the antagonist or vehicle, intravenously (1 mg kg$^{-1}$ in 200 µL saline containing 10% ethanol, 10 min prior to LPS challenge) or topically (10 mg site$^{-1}$ in 50% dimethyl sulphoxide/H$_2$O 60 min prior to complement challenge) Rats were infused i.v via the femoral catheter with either LPS (1 mg kg$^{-1}$ i.v in 100 µL saline), recombinant human C5a (2 µgkg$^{-1}$ in 100 µL), or vehicle control 10 minutes after the iv administration or 60 min after topical administration, of antagonist or vehicle control. All agents infused i.v were injected over a 2 min period, and were followed with a subsequent injection of 100 µL of saline to ensure complete delivery of the drug.

Whole blood samples (0.1 mL) were collected from the tail vein at the time of drug and LPS or C5a administration. Samples were collected at −15, 0, 5, 10, 15, 30, 60, 90, 120 and 150 min relative to the injection of LPS (zero time), and placed in tubes containing heparin (500 Units/mL). To isolate PMNs, 100 µL of blood was layered on to 200 µL of Histopaque 1077 (Sigma U.S.A.) solution and centrifuged at 400×g for 30 min min at room temperature (25° C.). The supernatant layer of platelet-rich plasma, the monocyte and lymphocyte interface and the separation layer of Histopaque were removed and discarded, leaving the PMN and red blood-cell rich layer. 9 mL of cold distilled water (4° C.) was added to the remaining pellet and shaken for 40 sec to lyse the red blood cells. Dulbecco's Phosphate-buffered saline (10× concentration), was added to restore isotonicity. The cells were then centrifuged at 400×g for 15 min at 10° C. The resulting supernatant was discarded, leaving a pellet of PMNs. The PMNs were further washed in 9 mL of saline, and centrifuged again at 400×g for 10 min at 10° C. Again the resulting supernatant was discarded, and the remaining pellet was resuspended in 100 µL of saline and mixed well. The number of PMNs was counted on a haemocytometer. The number of cells at each time point was calculated as a percentage of the total number of cells at time zero, prior to complement challenge or LPS.

The female Wistar rats chosen for this study were divided into the following treatment groups:

(a) LPS alone, in which 100 µL 5% ethanol (−15 min)+1 mg/kg LPS (0 min) were infused;

(b) ethanol control, in which 100 µL 5% ethanol was infused at −15 min to examine the influence of ethanol on the parameters measured in the rat;

(c) antagonist control, in which 1 mg/kg of cyclic antagonist was infused i.v. at −15 min;
(d) i.v antagonist+LPS, in which 1 mg/kg cyclic antagonists (−15 min) and 1 mg/kg LPS (0 min) were infused; and
(e) topically-applied antagonist+LPS, in which 10 mg/rat of antagonist was smeared on the abdominal-area of the rat, followed by iv infusion of LPS at 0 min.

Figure 12:
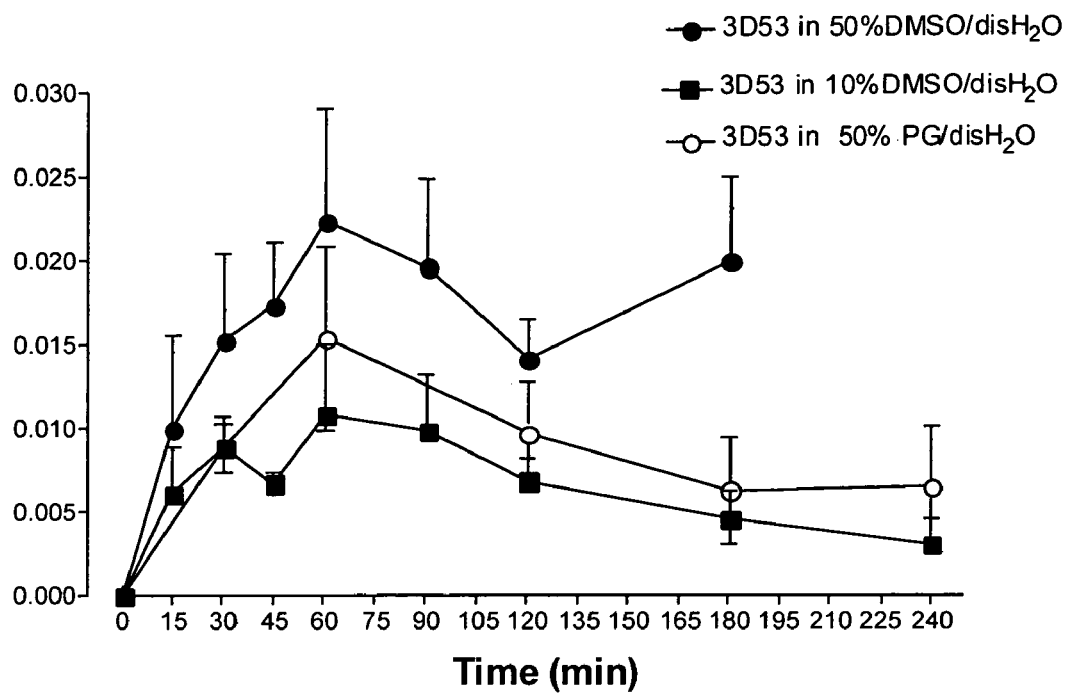
FIG. 12 shows that dermal application of 3D53 in DMSO/ distilled $H_2O$ or PG/$H_2O$ results in the appearance of the C5a antagonist in the circulating plasma within 15 minutes, and that significant levels persist for at least four hours. Points represent the mean±SEM in each group (n=6-8).

Administration of C5a antagonists such as 3D53 (PMX53) to the dermis of rats in an applied dose of 50 mg/kg results in the detection of pharmacologically significant levels of the drug in the circulating plasma. The application of the drug in a variety of solvents, such as dimethyl sulphoxide (DMSO), propylene glycol (PG) and water, in various combinations leads to the appearance of pharmacologically-relevant concentrations of the drug in the circulation, as illustrated in FIG. 12. This shows that dermal application of 3D53 in DMSO/distilled $H_2O$ or propylene glycol(PG)/$H_2O$ results in the appearance of the C5a antagonist in the circulating plasma within 15 min, and that significant levels persist for at least 4 hr.

EXAMPLE 9

Systemic Effects of C5a Antagonists Following Dermal Application

As described in Example 8, topical application of C5a antagonist to the dermis of an animal results in pharmacologically-relevant levels of the drug in the circulation. To show that these levels have systemic activity, the ability of these circulating levels of C5a antagonist to inhibit the neutropenic effects of C5a administered i.v. was determined.

Figure 13:
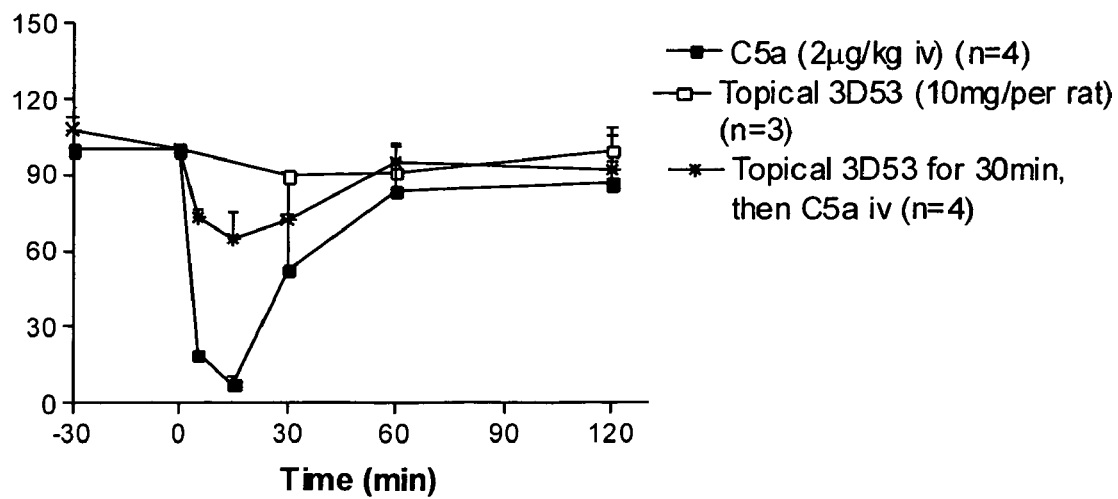
FIG. 13 shows the inhibition of C5a-induced neutropenia by topical administration of C5a antagonists. The results are expressed as percentage change from a zero time baseline.

The C5a receptor antagonist 3D53 was administered (10 mg/per rat) in 50% propylene glycol and 50% distilled $H_2O$. The composition was smeared evenly over the abdominal skin (4×8 $cm^2$) for 30 minutes, then C5a was administered i.v. in a dose of 2 µg/kg in 200 µl saline solution. Blood samples were taken at time points: −30 (before drug administration), 0 (before injection of C5a) and 5, 15, 30, 60, and 120 minutes for determination of circulating PMNs. As shown in FIG. 13, topical administration of compound 3D53 did indeed prevent the neutropaenic effects of C5a.

EXAMPLE 10

Topical Administration of C5a Antagonists Inhibits the Systemic Effects of LPS

Figure 14:
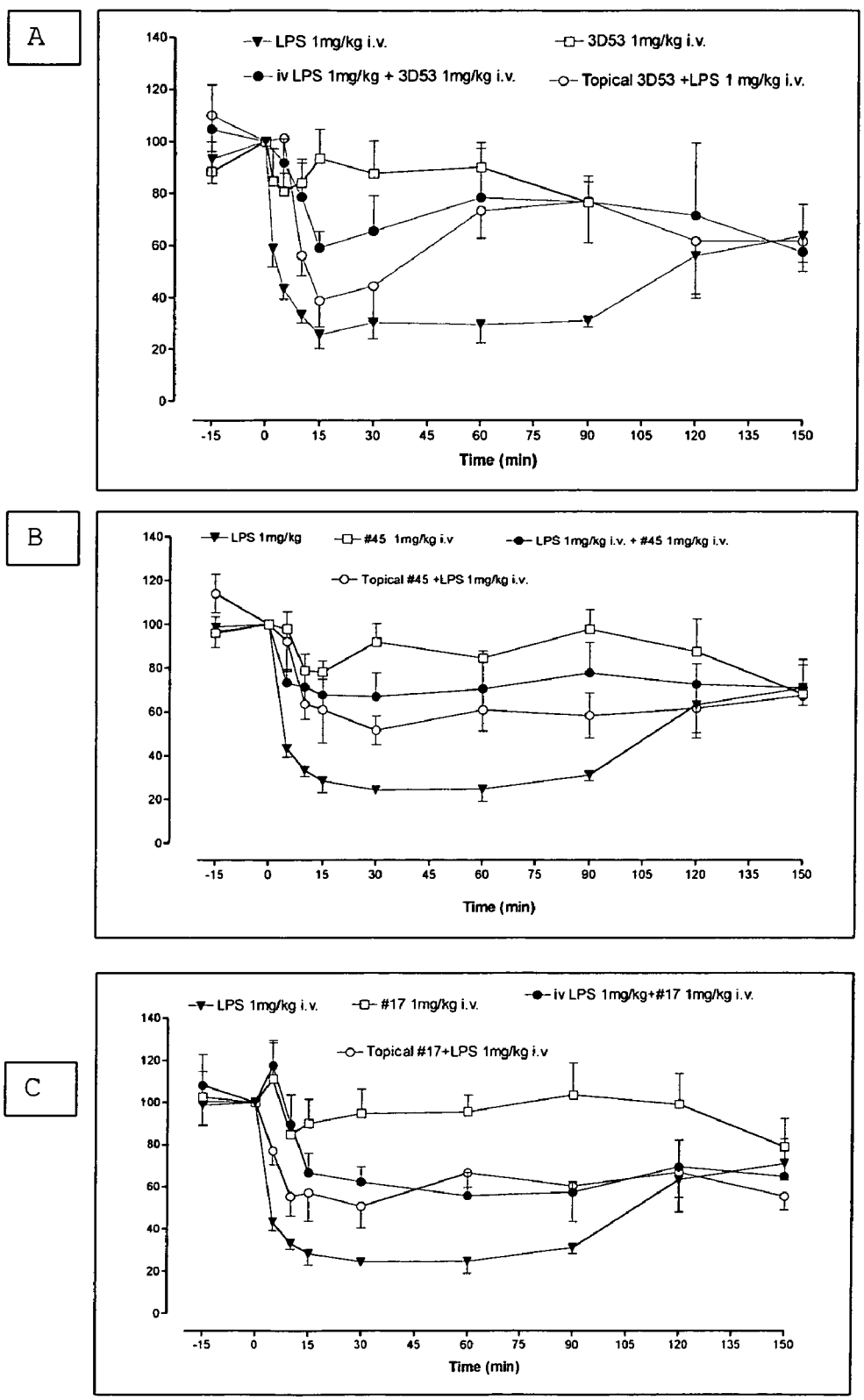
FIG. 14 shows that topical administration of C5a antagonists inhibits systemic effects of intravenously administered LPS in rats. The data show that administration of various C5a antagonists, either i.v. (1 mg/kg), or topically by dermal application (50 mg/kg total applied dose: solvent vehicle 50% DMSO/50% $H_2O$), inhibits the neutropenia caused by i.v. LPS (1 mg/kg).

The C5a antagonists, 3D53 (compound 1), as well as compound 17 and compound 45 were applied topically at a dose of to mg/rat in 50% DMSO/50% $H_2O$, as described above. LPS was injected 1 mg/kg i.v. 60 min after dermal application of the antagonists. Circulating PMN levels were monitored for 150 min following LPS injection, and the percentage change in PMN levels from zero time, when LPS was injected, was calculated. The results, illustrated in FIG. 14, show that each C5a antagonist applied topically inhibited the neutropenia response to i.v. LPS, and that the inhibition was comparable to that observed following i.v. administration of the drugs.

EXAMPLE 11

Effect of C5a Antagonist on Ischemia-Reperfusion Injury

Lower limb ischemia-reperfusion (I/R) injury is a serious problem following the surgical repair of abdominal aortic aneurysm, as well as following traumatic crush injuries (Kerrigan and Stotland, 1993). Ischemia and the subsequent reperfusion of the skeletal muscle tissue stimulates an inflammatory response in the affected muscle, as well as inducing injury in other tissues (Gute et al, 1998). In severe cases of limb ischemia, the resulting reperfusion is associated with high mortality, resulting from multiple system organ failure (Defraigne and Pincemail, 1997). In order to investigate the capacity of a potent C5a receptor antagonist to inhibit various parameters of local and remote organ injury following lower limb ischemia-reperfusion (I/R) in rats, rat hindlimbs were subjected to 2 hours ischemia and 4 hours reperfusion. This tourniquet shock model has been widely used as a model of lower limb I/R injury.

Rats were subjected to 2 hours bilateral hindlimb ischemia and 4 hours reperfusion. Drug-treated rats received AcF-[OPdChaWR] (1 mg/kg) i.v., either 10 min before ischemia or 10 min prior to reperfusion, or orally (10 mg/kg) 30 min prior to ischemia. Levels of circulating creatine kinase (CK), lactate dehydrogenase (LDH), alanine and aspartate aminotransferase (ALT/AST), creatinine, blood urea nitrogen (BUN), polymorphonuclear leukocytes (PMNs) and calcium ($Ca^{++}$) and potassium ($K^+$) ions were determined. These biochemical indices are known to reflect tissue or organ injury following I/R events. Other parameters measured included urinary protein levels, muscle edema and myeloperoxidase (MPO) concentrations in the lung, liver and muscle along with liver homogenate TNF-α concentrations. No significant changes were observed in any of these markers compared to sham-operated animals, indicating that the drug alone had no adverse effects as defined by changes in these markers. Limb I/R injury was characterized by significant elevations of CK, LDH, ALT, AST, creatinine, BUN, proteinuria, PMNs, serum $K^+$, muscle edema, organ MPO and liver homogenate TNF-α concentrations, but a significant reduction in serum $Ca^{++}$ concentrations. When rats were treated with AcF-[OPdChaWR], there were significant improvements in all these parameters.

The study was performed in accordance with guidelines from the National Health & Medical Research Council of Australia, and the experimental protocol approved by the University of Queensland Animal Ethics Committee. Female Wistar rats weighing 250-300 g were fasted overnight before being anaesthetized with the i.p. injection of 6 mg/kg xylazine and 120 mg/kg ketamine. Anesthesia was maintained throughout the study by additional injections of ketamine. Rats were placed on a heating pad to maintain normal body temperature, and a polyethylene catheter was inserted into the right jugular vein for the infusion of the C5a antagonist or 7% ethanol/saline. Bilateral hindlimb ischemia was then induced through the application of latex o-rings (marking rings; Hayes Veterinary Supplies, Brisbane, Australia) above the greater trochanter of each hind limb. Following 2 hours of ischemia, the latex rings were cut and removed and limbs allowed to reperfuse for 4 hours. Six experimental groups were used:

(a) sham-operated,
(b) ischemia-only,
(c) I/R-only,
(d) I/R+C5a antagonist (1 mg/kg, i.v.) administered 10 min prior to ischemia,
(e) I/R+C5a antagonist (10 mg/kg, p.o.) administered 30 min prior to ischemia, and
(f) I/R+C5a antagonist (1 mg/kg, i.v.) administered 10 min prior to reperfusion.

Sham-operated animals did not undergo any ischemia or reperfusion, and ischemia-only animals had tourniquets applied for 2 hours without subsequent reperfusion. All other groups underwent 2 hours of ischemia and 4 hours of reperfusion. Sham-operated, ischemia-only and I/R groups were infused with 7% ethanol/saline 10 min prior to ischemia, instead of drug. Blood was collected throughout the study from the tail vein, and serum or plasma was stored at either 4° C. or −20° C. for later biochemical assays. Urine was collected over the last hour of the study for the determination of urinary protein levels. At the completion of the experiment, rats were euthanased, and sections of the lungs, liver and gastrocnemius muscle removed and weighed for edema, neutrophil accumulation and liver TNF-α studies.

All experimental results are expressed as means±standard error of the mean (SEM). Data analysis was performed using GraphPad Prism 3.0 software (GraphPad Software, Inc. USA). Statistical comparisons were made to sham-operated and I/R-only groups, using a one-way analysis of variance followed by a Dunnett comparison post-test analysis. Statistical significance was assessed at $P<0.05$.

(a) Inhibition of Creatine Kinase and Lactate Dehydrogenase

Circulating levels of creatine kinase (CK) were measured in serum samples taken immediately after ischemia, following 1, 2 and 3 hours reperfusion, and at the completion of the study using a OK kit (Sigma, St. Louis, USA) according to the manufacturer's instructions. Serum was also taken 10 min after tourniquet release for CK measurement in I/R-only animals. A 1:5 dilution was used for samples taken after 2 hours reperfusion.

Circulating levels of lactacte dehydrogenase (LDH) were measured in serum samples taken immediately after ischemia, following 1, 2 and 3 hours reperfusion, and at the completion of the study Serum was also taken 10 min after tourniquet release for LDH measurement in I/R-only animals. Concentrations of LDH were determined with a LDH kit (Sigma), according to the manufacturer's instructions, with a 1:4 dilution of samples taken after 2 hours reperfusion. For both enzymes, all samples were stored at 4° C. and analyzed within 24 hours of collection. Results were expressed as Sigma-Franke (SF) units/mL.

As illustrated in FIG. 15, bilateral hindlimb I/R resulted in elevation of circulating levels of both CK and LDH after 1, 2, 3 and 4 hours of reperfusion, with peaks of both enzymes reached after 4 hours. Ischemia-only rats showed no significant elevation of either CK or LDH levels (CK, 58.3±23.5 units/mL; LDH, 269.5±72.8 units/mL; $P>0.05$; n=4) compared to sham-operated rats. In I/R-only rats there was no significant increase in the levels of these enzymes 10 min after tourniquet release (CK, 73.9±28.1 units/mL; LDH, 395.3±123.2 units/mL; $P>0.05$; n=4), compared to sham-operated rats, indicating a reperfusion-dependent elevation over the 4 hour time period. Reperfusion significantly elevated the plasma levels of both CK and LDH ($P<0.05$). Rats treated prior to ischemia with the C5a antagonist, either i.v. (1 mg/kg) or orally (10 mg/kg), had similar significantly decreased levels of both CK and LDH compared to I/R-only rats ($P<0.05$). In addition, rats treated i.v. with the C5a antagonist (1 mg/kg) just prior to reperfusion also displayed significant inhibition of CK and LDH levels, of similar magnitude to pre-ischemia treated rats ($P<0.05$). Levels of these enzymes during reperfusion in all the drug-treated rats were significantly higher than in sham-operated rats, indicating partial inhibition by the C5a antagonist ($P<0.05$).

(b) Inhibition of Alamine Transaminase and Aspartate Aminotransferase

Circulating levels of alanine aminotransferase (ALT) and aspartate aminotransferase (AST) were measured in plasma samples taken at the completion of the study and following 2 and 3 hours reperfusion. Serum was also taken 10 min after tourniquet release for measurement of ALT and AST in I/R-only animals. Concentrations of ALT and AST were determined with an ALT/AST kit (GPT/GOT; Sigma), according to the manufacturer's instructions, within 24 hours of collecting plasma, which was stored at 4° C. Results were expressed as SF units/ml.

Figure 16A:
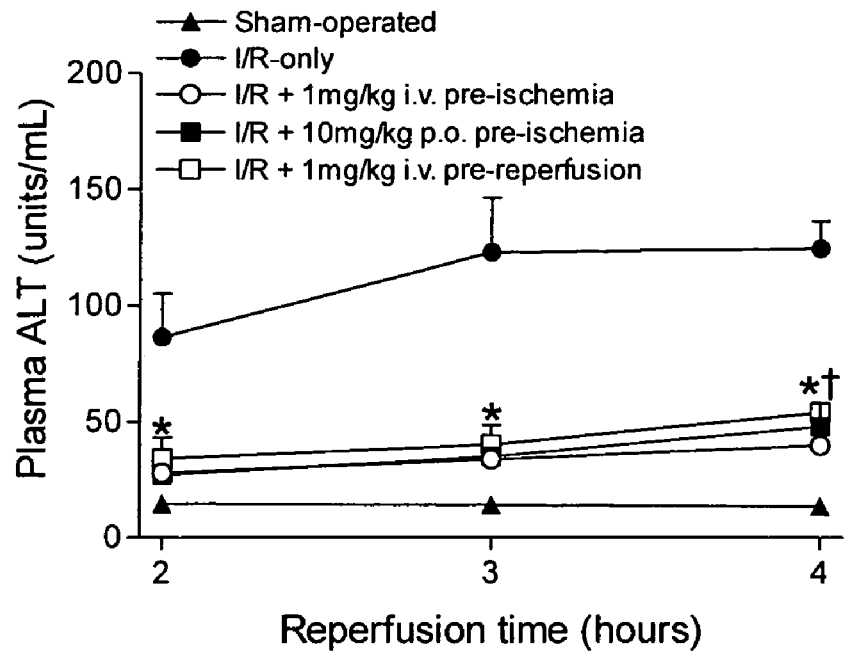
Figure 16B:
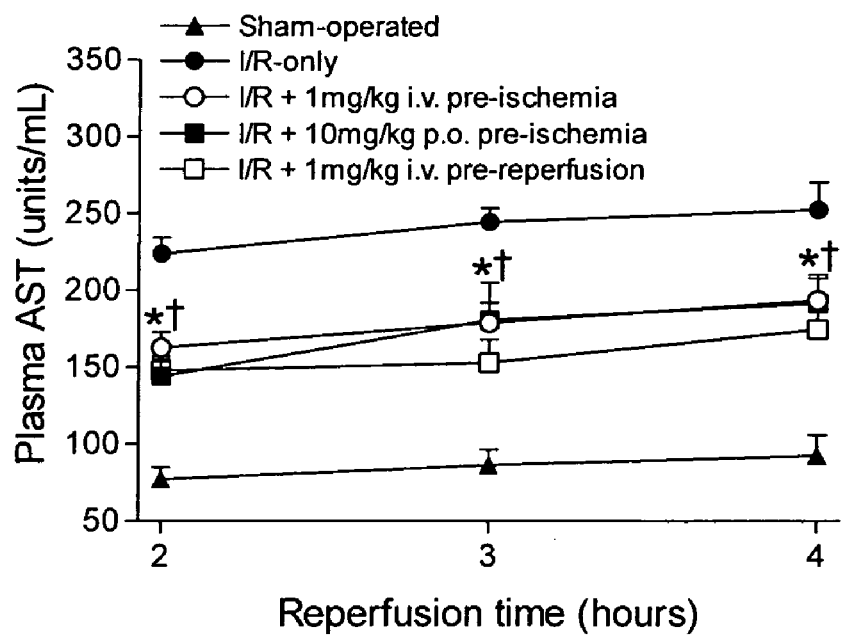

As shown in FIG. 16, limb I/R resulted in elevation of ALT and AST in the plasma after 2, 3 or 4 hours of reperfusion, with peaks of both enzymes reached after 4 hours. Rats receiving 2 hours of ischemia alone showed no significant elevation of either ALT or AST levels (ALT, 12.9±4.6 units/mL; AST, 91.4±10.4 units/mL; $P>0.05$; n=4) compared to sham-operated rats. In I/R-only rats, 10 min after tourniquet release, there was no significant increase in levels of these enzymes (ALT, 18.1±4.4 units/mL; AST, 105.9±21.3 units/mL; $P>0.05$; n=4), compared to sham-operated rats, again indicating a reperfusion-dependent elevation. C5a antagonist-treated rats in all 3 groups were found to have similar significant decreases in ALT and AST levels compared to I/R-only rats ($P<0.05$). After 4 hours of reperfusion, but not at 2 or 3 hours, drug-treated rats had significantly increased levels of ALT compared to sham-operated rats ($P<0.05$; FIG. 16A). In contrast, these drug-treated rats had increased AST levels compared to sham-operated rats at all time points measured, indicating the differential inhibition of the C5a antagonist for ALT and AST ($P<0.05$; FIG. 16B).

(c) Inhibition of Changes in Serum Levels of Potassium and Calcium Ions

Serum levels of potassium ion (K+) were measured with a flame photometer (Corning 435; Corning, U.S.A.) after the completion of each experiment, and 10 min after tourniquet release for I/R-only animals. Serum calcium ion (Ca++) concentrations were also measured at the completion of the study and 10 min after tourniquet release for I/R-only animals, using a calcium kit (Sigma). Samples were stored at −20° C. and analyzed for $K^+$ and $Ca^{++}$ levels within 2 weeks of collection. Results were expressed as mmol/L, and are summarized in Table 1.

TABLE 1

Alterations in serum cation levels following ischemia and 4 hours reperfusion in rats

| Experimental Group | $n^a$ | Serum $K^+$ (mmol/L) | Serum $Ca^{++}$ (mmol/L) |
|---|---|---|---|
| Sham-operated | 8 | 4.84 ± 0.29* | 2.66 ± 0.06* |
| Ischemia-only | 4 | 4.70 ± 0.17* | 2.52 ± 0.10* |
| I/R$^b$-only | 10 | 7.53 ± 0.34† | 2.23 ± 0.09† |
| I/R + 1 mg/kg i.v. pre-ischemia | 8 | 6.13 ± 0.18* | 2.46 ± 0.04* |
| I/R + 10 mg/kg p.o. pre-ischemia | 6 | 5.57 ± 0.58* | 2.49 ± 0.04* |
| I/R + 1 mg/kg i.v. pre-reperfusion | 6 | 5.02 ± 0.32* | 2.45 ± 0.10* |

Data represent the mean ± SEM.
$^a$Number of rats
$^b$Ischemia/reperfusion
*$P < 0.05$ vs I/R-only
†$P < 0.05$ vs sham-operated Inhibition of Blood Urea Nitrogen, Creatinine and Urinary Protein Circulating levels of blood urea nitrogen (BUN) were measured in serum samples taken at the completion of the study using a urea nitrogen kit (Sigma) according to the manufacturer's instructions. Samples were stored at −20° C. and were analyzed within 2 weeks of collection. Circulating levels of creatinine were measured in serum samples taken at the completion of the study using a creatinine kit (Sigma) according to the manufacturer's instructions. Protein concentrations in urine samples collected over a 1 hour period prior to the completion of the study were determined with a protein kit (Sigma) according to the manufacturer's instructions. Samples were stored at 4° C. and analyzed within 24 hours of collection. Results for all three parameters, expressed as mg/dL, are shown in Table 2.

TABLE 2

Alterations in kidney injury markers following ischemia and 4 hours reperfusion in rats

| Experimental Group | n[a] | Serum BUN[b] (mg/dL) | Plasma Creatinine (mg/dL) | Proteinuria (mg/dL) |
| --- | --- | --- | --- | --- |
| Sham-operated | 8 | 21.9 ± 1.2* | 0.79 ± 0.12* | 10.7 ± 2.2* |
| Ischemia-only | 4 | 22.8 ± 2.5* | 0.62 ± 0.26* | 13.3 ± 7.0* |
| I/R[c]-only | 10 | 41.9 ± 3.1[†] | 1.66 ± 0.09[†] | 120.3 ± 18.9[†] |
| I/R + 1 mg/kg i.v. pre-ischemia | 8 | 23.6 ± 1.6* | 1.07 ± 0.07* | 36.4 ± 11.4* |
| I/R + 10 mg/kg p.o. pre-ischemia | 6 | 21.8 ± 2.1* | 1.14 ± 0.14* | 45.8 ± 9.8* |
| I/R + 1 mg/kg i.v. pre-reperfusion | 6 | 22.0 ± 2.2* | 1.22 ± 0.05* | 41.2 ± 11.4* |

Data represent the mean ± SEM.
[a]Number of rats
[b]Blood urea nitrogen
[c]Ischemia/reperfusion
[d]Not detectable
*P < 0.05 vs I/R-only
[†]P < 0.05 vs sham-operated Hyperkalaemia was observed in I/R-only rats compared to sham-operated rats after 4 hours of reperfusion (P<0.05). Rats in all 3 drug-treatment groups had significantly lower K$^+$ levels than I/R-only rats, with rats treated just prior to reperfusion showing near-normal levels (P<0.05). Following ischemia and 4 hours of reperfusion, I/R-only rats had significantly decreased serum concentrations of Ca$^{++}$ compared to sham-operated animals (P<0.05). Rats in all 3 drug-treatment groups showed a similar inhibition of the I/R-induced decrease in Ca$^{++}$ levels (P<0.05). Levels of both K$^+$ and Ca$^{++}$ in drug-treated I/R rats, as well as ischemia-only rats, were not significantly different from those in sham-operated rats (P>0.05). Levels of these ions 10 min after the release of the tourniquet in I/R-only rats (K$^+$, 5.27±0.49 mmol/L; Ca$^{++}$, 2.50±0.17 mmol/L; P>0.05; n=4) were also not significantly different from those in sham-operated rats.

Following ischemia and 4 hours reperfusion, I/R-only rats had significantly elevated serum BUN and creatinine levels, as well as increased urinary protein concentrations, compared to sham-operated rats (P<0.05). Two hours of ischemia alone caused no increase in any of these parameters compared to sham-operated rats (P>0.05). Rats treated with the C5a antagonist in all 3 groups had significantly lower levels of these parameters compared to I/R-only rats (P<0.05), and these levels were not significantly different from those in sham-operated rats (P>0.05).

Inhibition of Polymorphonuclear Leukocyte Numbers and Neutrophil Accumulation

Figure 17A:
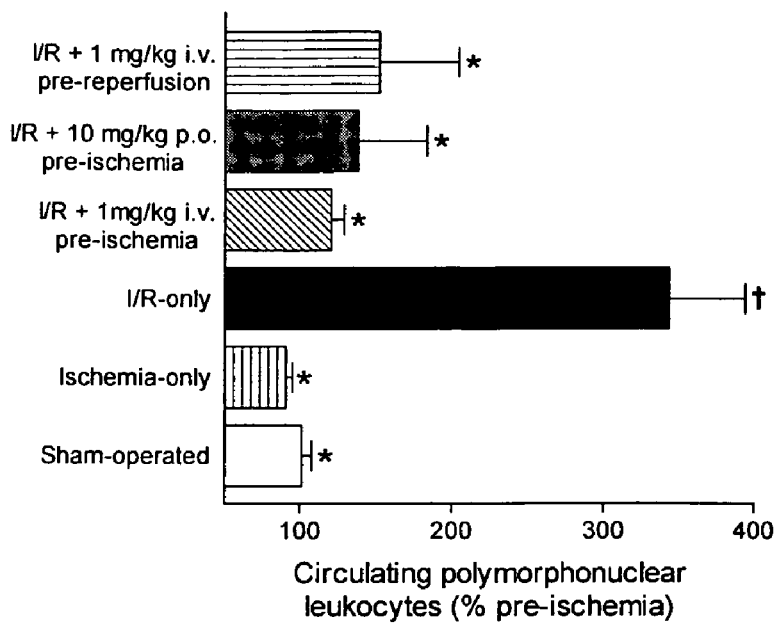
Figure 17B:
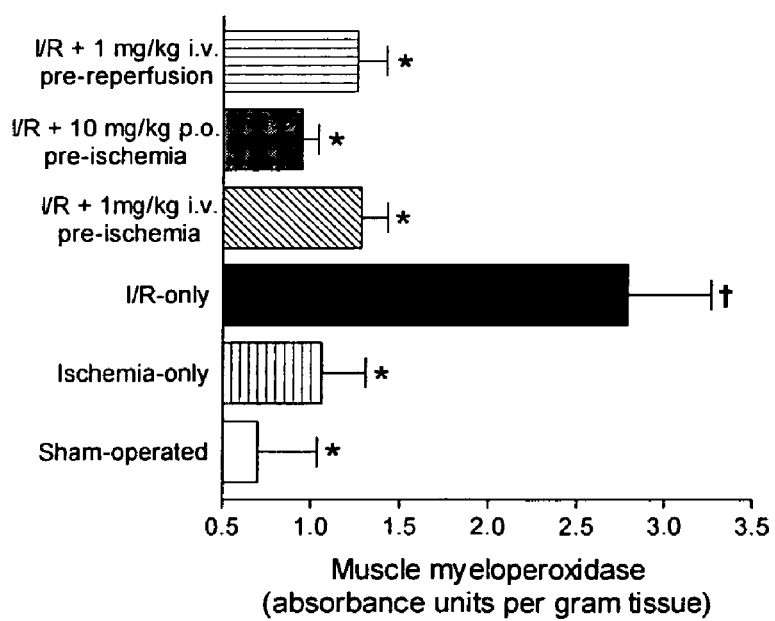
Figure 17C:
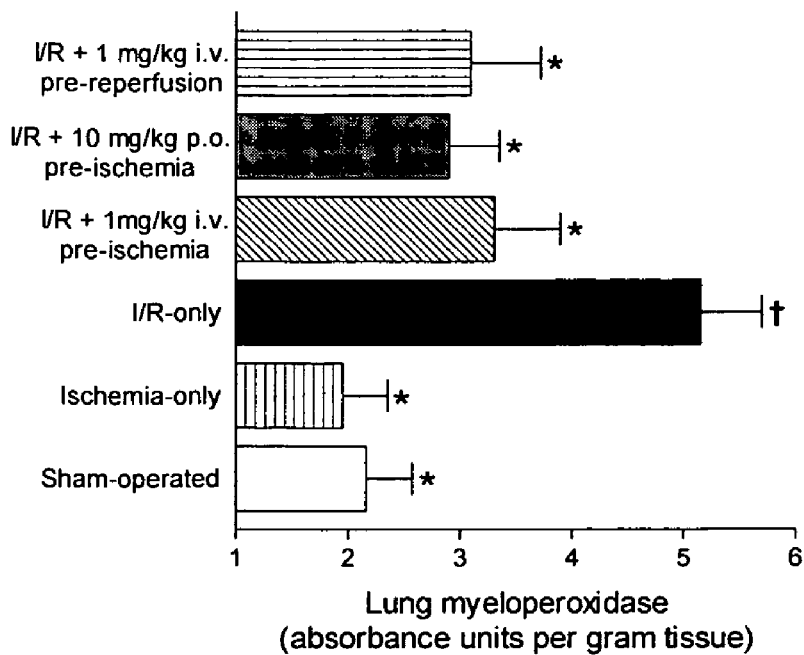
Figure 17D:
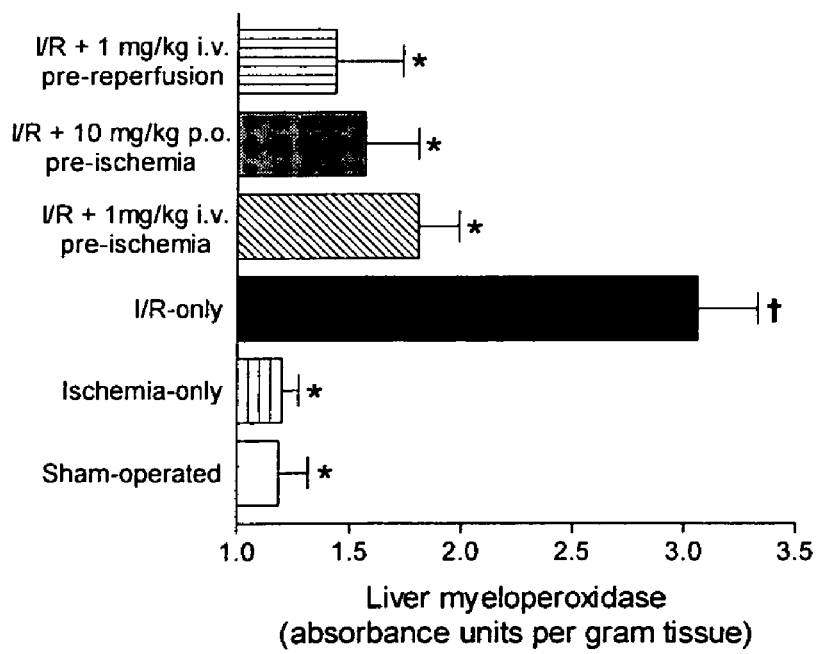

The numbers of circulating PMNs were measured in heparinised blood samples taken just prior to ischemia and at the completion of the study, as described by Strachan et al., (2000). Numbers of PMNs in the final samples were expressed as a mean percentage±SEM of pre-ischemia As shown in FIG. 17A, the number of circulating PMNs was found to be significantly elevated in I/R-only rats following 4 hours of reperfusion, compared to sham-operated rats (P<0.05). Ischemia-only rats had no significant elevation of PMs compared to sham-operated rats (P>0.05). PMN numbers in rats from all 3 drug-treated groups were not significantly different from those in sham-operated rats (P>0.05), and were significantly decreased compared to those in I/R-only rats (P<0.05), with rats treated i.v. (1 mg/kg) pre-ischemia displaying the greatest inhibitory effect.

The infiltration of neutrophils into the liver, lung and muscles of rats was determined by measuring the level of myeloperoxidase (MPO) activity. Sections of lung (~0.5 g), liver (~1 g) and the left lower limb muscle (~1 g) obtained at the completion of the study were weighed and then homogenized with 1 mL phosphate-buffered saline (PBS). Samples were then sonicated for 20 seconds for liver and lung samples or 60 seconds for muscle samples. Following centrifugation (14,000×g, 10 min, 22° C.), the resulting supernatants were tested immediately for MPO levels. The assay mixture consisted of o-dianasidine (2.85 mg/mL; Sigma), hydrogen peroxidase (0.85%) and a 1:40 dilution of samples in PBS. Absorbances were read at 450 nM, 5 min after substrate addition, and results expressed as absorbance units/g tissue.

The level of MPO activity in the hindlimb muscles, lungs and liver of rats were taken as a measurement of neutrophil sequestration into the tissue (Kyriakides et al., 2000). As shown in FIGS. 17 B,C and D, there were significant elevations in MPO activity in the hindlimb muscles, lungs and liver of I/R-only rats compared to those in sham-operated rats (P<0.05;), whereas sham-operated rats, ischemia-only rats had no significant increase in MPO activity in any of these tissues (P>0.05). Drug-treated rats in all 3 groups had significant decreases in MPO activity in all tissues compared to I/R-only rats (P<0.05), and the levels were not significantly different from those in sham-operated rats (P>0.05).

Inhibition of Liver Homogenate TNF-α

Levels of TNF-α were measured in liver homogenate supernatant samples, using an enzyme-linked immunosorbent assay kit (OptEIA, Pharmingen, USA) as previously described (Strachan et al., 2000). A 1:10 dilution of supernatant from liver homogenate samples was used in the assay. Supernatant was stored at −20° C., and samples were analyzed within 2 weeks of collection. Results were expressed as ng/g tissue. As shown in FIG. 18, liver homogenate samples from I/R-only rats had significantly increased TNF-α concentrations compared to those from sham-operated rats (P<0.05). Levels of TNF-α in ischemia-only rats were not significantly different from those from sham-operated rats (P>0.05). In drug-treated rats, all 3 groups had a similar decrease in TNF-α concentrations compared to I/R-only rats (P<0.05), which were not significantly different from those from sham-operated animals (P>0.05).

Inhibition of Muscle Edema

Sections of the right lower limb muscle (~1 g) obtained at the completion of the study were weighed and placed in an oven for 24 hours at 80° C. before weighing again. The wet-to-dry weight ratio was determined and taken as a measurement of muscle edema. As illustrated in FIG. 19, wet-to-dry weight ratios of the hindlimb muscle in I/R-only rats were significantly increased compared to those in sham-operated animals (P<0.05). Ratios in ischemia-only animals were not significantly different from sham-operated animals (P>0.05). In all 3 groups of drug-treated rats, there was a similar decrease in wet-to-dry ratios compared to those in I/R-only rats (P<0.05), and these values were not significantly different from those in sham-operated animals (P>0.05).

The results show that rats subjected to 2 hours of tourniquet-induced bilateral hindlimb ischemia and 4 hours reperfusion suffered both local injury and injury to the lungs, liver and kidney, as measured by various indices of tissue stress. Rats subjected to ischemia alone had no significant alterations in disease markers compared to sham-operated animals. Blood taken from I/R-only animals after only 10 min of reperfusion also had no significant changes in the plasma or serum levels of CK, LDH, AST, ALT, $K^+$ or $Ca^{++}$ compared to sham-operated animals. The severity of local skeletal muscle injury was assessed by measuring increases in muscle edema and neutrophil accumulation following 4 hours of reperfusion, as well as serum CK and LDH throughout the reperfusion period. The cytosolic enzyme CK is found predominantly in muscle, and is a reliable marker of muscle tissue damage (Tay et al., 2000). Lactate dehydrogenase is also a cytosolic enzyme found in the muscle, but is present in many other tissues as well (Carter et al., 1998). Consequently, LDH was a less specific measure of muscle injury, but still provided a measure of general tissue injury.

Indices of remote organ injury were detected in the lungs, liver and kidneys of animals subjected to ischemia and reperfusion episodes. The potential for lung injury was assessed by measuring increases in neutrophil accumulation in lung parenchyma. Hepatic injury was also quantified by measuring the increase in hepatic TNF-$\alpha$ and neutrophil accumulation, and by measuring increases in plasma levels of ALT and AST. Although increases in plasma levels of ALT and AST have typically been used as markers of liver pathology, both of these enzymes are also found within the muscle, and thus any increases may in part be attributed to muscle, rather than liver damage (Tay et al., 2000). Kidney dysfunction following skeletal muscle I/R is common (Tanaka et al., 1995). We found increases in serum BUN and plasma creatinine in I/R rats. However, creatinine, and in particular BUN, are also derived from the muscle, and the observed increases may also be attributed to muscle injury (Carter et al., 1998) We found a sizeable increase in proteinuria in I/R rats, indicating some degree of kidney injury.

The C5a antagonist AcF-[OPdChaWR] was found to inhibit a multitude of disease markers of local tissue and remote organ injury in this model. These results indicate a key role for C5a in the pathophysiology of skeletal muscle I/R injury. Given the high incidence of complications following lower limb ischemia and reperfusion in humans, the C5a receptor antagonists of the invention represent a possible future treatment of these complications, especially when I/R injury is anticipated, such as in surgical procedures. The ability of C5a antagonists to block both proinflammatory cytokine production and neutrophil trafficking may be key factors in their disease-modifying properties. The oral activity demonstrated here is a useful drug property for its widespread use in clinical situations.

Discussion

This invention describes a series of conformationally-constrained turn-containing cyclic molecules which are pre-organized for binding to cells which also bind human C5a. The principal feature of the compounds of the invention is the pre-organized turn conformation presented by the cyclic scaffold, which assembles at least three hydrophobic groups into neighbouring space, creating a hydrophobic surface 'patch'.

This turn conformation of the antagonist may permit the cyclic peptide to bind in the transmembrane region of the C5a receptor at, or close to, the location which is also bound by the C-terminal end of human C5a.

The results described herein enable the design and development of even more potent conformationally constrained small molecule antagonists of C5a. In principle the features of these cyclic antagonists are also useful for designing unrelated non-peptidic templates which similarly project substituents, corresponding to or similar to those attached to the cyclic peptide scaffolds described herein, into similar three-dimensional space as that occupied by these C5a receptor antagonists when bound to the receptor.

Cyclic peptides have several important advantages over acyclic peptides as drug candidates (Fairlie et al 1995, Fairlie et al, 1998, Tyndall and Fairlie, 2001). The cyclic compounds described in this specification are stable to proteolytic degradation for at least several hours at 37° C. in human blood or plasma, in human or rat gastric juices, or in the presence of digestive enzymes such as pepsin, trypsin and chymotrypsin. In contrast, short linear peptides composed of L-amino acids are rapidly degraded to their component amino acids within a few minutes under these conditions. A second advantage lies in the constrained single conformations adopted by the cyclic and non-peptidic molecules, in contrast to acyclic or linear peptides, which are flexible enough to adopt multiple structures in solution other than the one required for receptor-binding. Thirdly, cyclic compounds such as those described in this invention are usually more lipid-soluble and more pharmacologically bioavailable as drugs than acyclic peptides, which can rarely be administered orally. Fourthly, the plasma half-lives of cyclic molecules are usually longer than those of peptides.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Carter W O, Bull C, Bortolon E, et al. A murine skeletal muscle ischemia-reperfusion injury model: differential pathology in BALB/c and DBA/2N mice. J Appl Physiol 1998; 85:1676-1683.

Defraigne J O, Pincemail J. Local and systemic consequences of severe ischemia and reperfusion of the skeletal muscle. Physiopathology and prevention. Acta Chir Belg 1997; 97:176-186.

DeMartino, J. A., Konteatis, Z. D., Siciliano, S. J., Van Riper, G., Underwood, D. J., Fischer, P. A., Springer, M. S. J. Biol. Chem., 1995 270 15966-15969

DeMartino, J. A., Van Riper, G., Siciliano, S. J., Molineaux, C. J., Konteatis, Z. D., Rosen, H. Springer, M. S. J. Biol. Chem., 1994 269 14446-14450.

Ember, J. A., Sanderson, S. D., Taylor, S. M., Kawahara, M. and Hugli, T. E. J. Immunol., 1992 148 3165-3173.

Fairlie, D. P., Wong, A. K.; West, M. W. Curr. Med. Chem., 1998, 5, 29-62.

Fairlie, D. P., Abbenante, C. and March, D. Curr. Med. Chem., 1995 2 672-705.

Finch, A. M., Vogen, S. M., Sherman, S. A., Kirnarsky, L., Taylor, S. M., and Sanderson, S. D. J. Med Chem., 1997 40 877.

Gerard, C and Gerard, N. P. Ann. Rev. Immunol., 1994 12 775-808.

Gerard, N and Gerard, C. Nature, 1991 349 614-617.

Gute D C, Ishida T, Yarimizu K, Korthuis R J. Inflammatory responses to ischemia and reperfusion in skeletal muscle. Mol Cell Biochem 1998; 179:169-187.

Haviland, D. L., McCoy, R. L., Whitehead, W. T., Akama, H., Molmenti, E. P., Brown, A., Haviland, J. C., Parks, W. C., Perlmutter, D. H and Wetsel, R. A. J. Immunol., 1995 154 1861-1869.

Kawai, M., Quincy, D. A., Lane, B., Mollison, K. W., Luly, J. R., Carter, G. W. J. Med. Chem., 1991 34 2068-71.

Kawai, N., Quincy, D. A., Lane, B., Mollison, K. W., Or, Y.-S., Luly, J. R., and Carter, G. W. J. Med. Chem., 1992 35 220-223.

Kerrigan C L, Stotland M A. Ischemia reperfusion injury: a review. Microsurgery 1993; 14:165-175.

Kohl, J., Lubbers, B., Klos, A., et al. Eur. J. Immunol., 1993 23 646-652.

Konteatis, Z. D., Siciliano, S. J., Van Riper, G., Molineaux, C. J., Pandya, S., Fischer, P., Rosen, H., Mumford, R. A., and Springer, M. S. J. Immunol., 1994 153 4200-4204.

Kyriakides C, Austen W G, Jr., Wang Y, et al. Neutrophil mediated remote organ injury after lower torso ischemia and reperfusion is selectin and complement dependent. J Trauma 2000; 48:32-38.

Morgan, E. L., Sanderson, S. D., Scholz, W., Noonal, D. J., Weigle, W. O. and Hugli, T. E. J. Immunol., 1992 48 3937-3942.

Sanderson, S. D., Ember, J. A., Kirnarsky, L., Sherman, S. A., Finch, A. M., Taylor, S. M. J. Med. Chem., 1994 37 3171-3180.

Sanderson, S. D., Kirnarsky, L., Sherman, S. A., Vogen, S. M., Prakesh, O., Ember, J. A., Finch, A. M. and Taylor, S. M. J. Med. Chem., 1995 38 3669-3675.

Siciliano, S. J., Rollins, T. E., DeMartino, J., Konteatis, Z., Malkowitz, L., VanRiper, G., Bondy, S., Rosen, H. and Springer, M. S. Proc. Nat. Acad. Sci. USA, 1994 91 1214-1218.

Sim, E. The Natural Immune System. Humoral Factors, 1993, IRL Press, Oxford University Press, Oxford.

Strachan, A J, Haaima, G, Fairlie, D P and S M Taylor. Inhibition of the reverse passive Arthus reaction and endotoxic shock in rats by a small molecule C5a receptor antagonist. *J. Immunol.* 164: 6560-6565, 2000.

Strachan A J, Woodruff T M, Haaima G, et al. A new small molecule C5a receptor antagonist inhibits the reverse-passive Arthus reaction and endotoxic shock in rats. J Immunol 2000; 164:6560-6565.

Tanaka T, Kita T, Liu R, Tanaka N. Protective effect of peptide leukotriene antagonist on renal failure induced by a tourniquet in rabbits. Forensic Sci Int 1995; 71:57-64.

Tay S K, Ong H T, Low P S. Transaminitis in Duchenne's muscular dystrophy. Ann Acad Med Singapore 2000; 29:719-722.

Tempero, R. M., Hollingsworth, M. A., Burdick, M. D., Finch, A. M., Taylor S. M., Vogen, S. M., Morgan, E. L., and Sanderson, S. D. J. Immunol., 1997 158 1377-1382.

Tyndall, J. D. A.; Fairlie, D. P. *Curr. Med. Chem.* 2001, 8, 893-907.

Whaley, K. Complement in Health and Disease. Immunology and Medicine Series, Ed. Reeves, W. G., 1987, MTP Press Ltd, Lancaster.

The invention claimed is:

1. A compound of the formula:

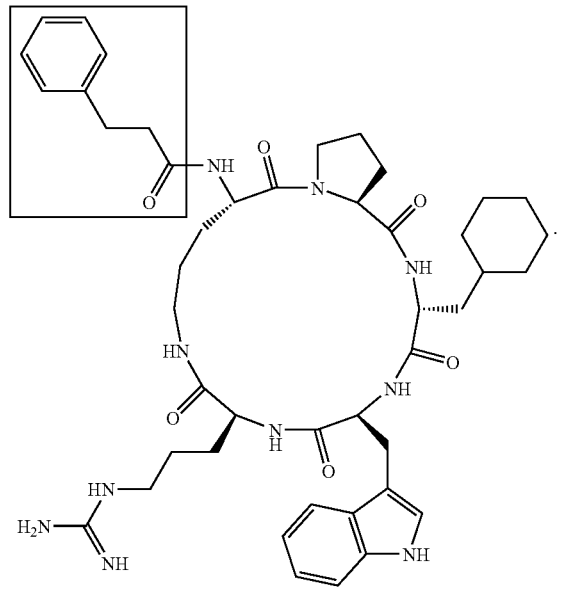

2. The compound of claim 1, wherein the compound is an antagonist of a C5a G protein-coupled receptor and has no C5a agonist activity.

3. The compound of claim 2, wherein the compound has antagonist activity against a C5a receptor, a vasopressin receptor, or a neurokinin receptor.

4. The compound of claim 3, wherein the compound has antagonist activity at submicromolar concentrations.

5. The compound of claim 4, wherein the compound has a receptor affinity $IC_{50}<25$ μM, and an antagonist potency $IC_{50}<1$ μM.

6. The compound of claim 1, together with a pharmaceutically-acceptable carrier or excipient.

7. A composition comprising the compound of claim 1, and a pharmaceutically-acceptable carrier or excipient.

* * * * *